US010918606B2

(12) United States Patent
Johnson et al.

(10) Patent No.: US 10,918,606 B2
(45) Date of Patent: *Feb. 16, 2021

(54) DELIVERY OF DRUG NANOPARTICLES AND METHODS OF USE THEREOF

(71) Applicant: DFB Soria, LLC, Fort Worth, TX (US)

(72) Inventors: Keith Johnson, Durham, NC (US); Robert Lathrop, Petaluma, CA (US); Meidong Yang, Petaluma, CA (US); Holly Maulhardt, San Luis Obispo, CA (US); Roland Franke, Delta (CA)

(73) Assignee: DFB Soria, LLC, Fort Worth, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/567,164

(22) Filed: Sep. 11, 2019

(65) Prior Publication Data

US 2020/0069600 A1   Mar. 5, 2020

Related U.S. Application Data

(63) Continuation of application No. 15/899,228, filed on Feb. 19, 2018, now Pat. No. 10,449,162, which is a continuation of application No. PCT/US2016/052133, filed on Sep. 16, 2016.

(60) Provisional application No. 62/219,453, filed on Sep. 16, 2015.

(51) Int. Cl.
*A61K 9/51* (2006.01)
*A61K 9/00* (2006.01)
*A61K 9/14* (2006.01)
*A61K 47/10* (2017.01)
*A61K 47/34* (2017.01)
*A61K 47/18* (2017.01)
*A61K 47/32* (2006.01)
*A61K 47/06* (2006.01)
*A61K 47/24* (2006.01)
*A61K 31/337* (2006.01)

(52) U.S. Cl.
CPC .......... *A61K 9/5146* (2013.01); *A61K 9/0014* (2013.01); *A61K 9/145* (2013.01); *A61K 9/146* (2013.01); *A61K 9/5176* (2013.01); *A61K 31/337* (2013.01); *A61K 47/06* (2013.01); *A61K 47/10* (2013.01); *A61K 47/186* (2013.01); *A61K 47/24* (2013.01); *A61K 47/32* (2013.01); *A61K 47/34* (2013.01)

(58) Field of Classification Search
None
See application file for complete search history.

(56) References Cited

U.S. PATENT DOCUMENTS

| | | |
|---|---|---|
| 5,399,363 A | 3/1995 | Liversidge et al. |
| 5,756,537 A | 5/1998 | Gill |
| 5,833,891 A | 11/1998 | Subramaniam et al. |
| 5,874,029 A | 2/1999 | Subramaniam et al. |
| 5,886,026 A | 3/1999 | Hunter et al. |
| 5,994,341 A | 11/1999 | Hunter et al. |
| 6,004,573 A | 12/1999 | Rathi et al. |
| 6,113,795 A | 9/2000 | Subramaniam et al. |
| 6,117,949 A | 9/2000 | Rathi et al. |
| 6,322,817 B1 | 11/2001 | Maitra et al. |
| 6,365,191 B1 | 4/2002 | Burman et al. |
| 6,406,722 B1 | 6/2002 | Gallaher |
| 6,515,016 B2 | 2/2003 | Hunter |
| 6,656,966 B2 | 12/2003 | Garvey et al. |
| 6,689,803 B2 | 2/2004 | Hunter |
| 6,749,868 B1 | 6/2004 | Desai et al. |
| 6,892,091 B1 | 5/2005 | Ben-Haim et al. |
| 7,217,735 B1 | 5/2007 | Au et al. |
| 7,361,683 B2 | 4/2008 | Lee et al. |
| RE40,493 E | 9/2008 | Straub et al. |
| 7,744,923 B2 | 6/2010 | Rajewski et al. |
| 7,807,369 B2 | 10/2010 | Van Der Burg et al. |
| 7,820,788 B2 | 10/2010 | Desai et al. |
| 7,879,360 B2 | 2/2011 | Cunningham et al. |
| 7,901,698 B2 | 3/2011 | Zanutto et al. |
| 8,034,765 B2 | 10/2011 | De et al. |
| 8,039,494 B1 | 10/2011 | Winckle et al. |
| 8,062,658 B2 | 11/2011 | Shalaby et al. |
| 8,178,123 B2 | 5/2012 | Pauletti et al. |
| 8,221,779 B2 | 7/2012 | Jonas et al. |

(Continued)

FOREIGN PATENT DOCUMENTS

| | | |
|---|---|---|
| CN | 101129338 | 2/2008 |
| CN | 101829061 | 9/2010 |

(Continued)

OTHER PUBLICATIONS

Utreja et al., "Localized delivery of paclitaxel using elastic liposomes: Formulation development and evaluation" *Drug Delivery* 2011, 18(5), 367-376.
Alcaraz et al., "Cutaneous metastases from Internal Malignancies: A clinicopathologic and immunohistochemical Review," *Am. J. Dermatopathol*, 2012, 34:347-393.
Ali et al., "Inflammation of actinic keratosis during paclitaxel chemotherapy," *BMJ. Case. Rep.*, 2015.
American College of Obstetricians and Gynecologists. "Management of vulvar intraepithelial neoplasia. Committee Opinion No. 675" *Obstet Gynecol.*, 2016, 128:e178-182.
Barua, et al. "Challenges associated with penetration of nanoparticles across cell and tissue barriers: A review of current status and future prospects." Nano Today (2014) 9, 223-243.

(Continued)

*Primary Examiner* — James W Rogers
(74) *Attorney, Agent, or Firm* — Norton Rose Fulbright US LLP

(57) ABSTRACT

Disclosed are compositions and methods useful for enhancing the skin penetration of drug nanoparticles. The compositions can be hydrophobic and include a hydrophobic carrier, a volatile silicone fluid, and drug nanoparticles. Also disclosed are methods for inhibiting crystal growth of drug nanoparticles in an aqueous carrier or a hydrophobic carrier. Further, methods to topically treat psoriasis using compositions containing nanoparticles of paclitaxel or other taxanes are disclosed.

25 Claims, 4 Drawing Sheets

(56) References Cited

U.S. PATENT DOCUMENTS

| | | | |
|---|---|---|---|
| 8,293,277 | B2 | 10/2012 | Swanson et al. |
| 8,299,088 | B2 | 10/2012 | Matteucci et al. |
| 8,343,962 | B2 | 1/2013 | Kisak et al. |
| 8,486,924 | B2 | 7/2013 | Ansell et al. |
| 8,486,978 | B2 | 7/2013 | Winckle et al. |
| 8,778,181 | B1 | 7/2014 | Johnson et al. |
| 8,846,110 | B2 | 9/2014 | Lee et al. |
| 8,846,771 | B2 | 9/2014 | Desai et al. |
| 8,865,194 | B1 | 10/2014 | Gans et al. |
| 8,906,392 | B2 | 12/2014 | Berkland et al. |
| 9,018,146 | B2 | 4/2015 | Wheeler et al. |
| 9,056,137 | B2 | 6/2015 | Hsu |
| 9,149,440 | B2 | 10/2015 | Turos et al. |
| 9,149,455 | B2 | 10/2015 | Desai et al. |
| 9,278,069 | B2 | 3/2016 | Berkland et al. |
| 9,283,284 | B2 | 3/2016 | Renier et al. |
| 9,339,548 | B2 | 5/2016 | Hsu |
| 9,572,790 | B2 | 2/2017 | Ye et al. |
| 9,724,323 | B2 | 8/2017 | Desai et al. |
| 9,763,946 | B2 | 9/2017 | Lin |
| 9,814,685 | B2 | 11/2017 | Baltezor et al. |
| 10,555,898 | B2 | 2/2020 | Dizerega |
| 2001/0029264 | A1 | 10/2001 | McChesney |
| 2002/0013298 | A1 | 1/2002 | Hunter |
| 2004/0033267 | A1 | 2/2004 | Merisko-Liversidge et al. |
| 2004/0220081 | A1 | 11/2004 | Kreitz |
| 2005/0129736 | A1 | 6/2005 | Hunter et al. |
| 2005/0281750 | A1 | 12/2005 | Willcox et al. |
| 2006/0104999 | A1 | 5/2006 | Hesson et al. |
| 2006/0147383 | A1 | 7/2006 | Mallard et al. |
| 2006/0188566 | A1 | 8/2006 | Liversidge et al. |
| 2007/0041910 | A1 | 2/2007 | Pitre et al. |
| 2008/0063699 | A1 | 3/2008 | Teifel et al. |
| 2008/0160095 | A1 | 7/2008 | Desai et al. |
| 2008/0220075 | A1 | 9/2008 | Merisko-Liversidge et al. |
| 2009/0042950 | A1 | 2/2009 | Pandya |
| 2009/0060870 | A1 | 3/2009 | Van Der Burg et al. |
| 2009/0202654 | A1 | 8/2009 | Nixon |
| 2009/0291925 | A1 | 11/2009 | Shalaby |
| 2010/0204175 | A1 | 8/2010 | Renier et al. |
| 2011/0105596 | A1* | 5/2011 | Hosen .................. C12Q 1/6886 514/44 R |
| 2012/0134951 | A1 | 5/2012 | Stasko |
| 2012/0237768 | A1 | 9/2012 | Hirokawa et al. |
| 2012/0252897 | A1 | 10/2012 | Mehta et al. |
| 2013/0211384 | A1 | 8/2013 | Raspagliesi |
| 2014/0073615 | A1 | 3/2014 | Carlsson et al. |
| 2014/0199244 | A1 | 7/2014 | Rijcken et al. |
| 2014/0294967 | A1 | 10/2014 | Borbely et al. |
| 2014/0296140 | A1 | 10/2014 | Johnson et al. |
| 2015/0342872 | A1 | 12/2015 | Williamson et al. |
| 2016/0184331 | A1 | 6/2016 | Kanemitsu et al. |
| 2016/0213757 | A1 | 7/2016 | Edelson et al. |
| 2016/0354336 | A1 | 12/2016 | Baltezor et al. |
| 2016/0374953 | A1 | 12/2016 | Baltezor et al. |
| 2017/0333384 | A1 | 11/2017 | Desai et al. |
| 2018/0177739 | A1 | 6/2018 | Johnson et al. |
| 2019/0022081 | A1 | 1/2019 | Baltezor et al. |

FOREIGN PATENT DOCUMENTS

| | | |
|---|---|---|
| CN | 101843582 | 9/2010 |
| GB | 2474930 | 5/2011 |
| JP | 2001503785 | 3/2001 |
| JP | 2010529025 | 8/2010 |
| JP | 2010533163 | 10/2010 |
| WO | WO 2016/071365 | 5/1916 |
| WO | WO 2017/049083 | 3/1917 |
| WO | WO 95/03036 | 2/1995 |
| WO | WO 98/24427 | 6/1998 |
| WO | WO 2000/072827 | 12/2000 |
| WO | WO 2003/032906 | 4/2003 |
| WO | WO 2006/133271 | 12/2006 |
| WO | WO 2008/150532 | 12/2008 |
| WO | WO 2009/007764 | 1/2009 |
| WO | WO 2011/151418 | 12/2011 |
| WO | WO 2012/130314 | 10/2012 |
| WO | WO 2014/091729 | 6/2014 |
| WO | WO 2014/210485 | 12/2014 |
| WO | WO 2016/197091 | 12/2016 |
| WO | WO 2017/049083 | 3/2017 |

OTHER PUBLICATIONS

Batheja, et al. optimization and in (2011). "Topical drug delivery by a polymeric nanosphere gel: Formulation vitro and in vivo skin distribution studies." J Control Release, 149(2):159-67.

Bharadwaj et al., "Topical delivery of paclitaxel for treatment of skin cancer", Drug Development and Industrial Pharmacy, vol. 6, No. 9, 2016, pp. 1482-1494.

Boehncke et al., "Leukocyte extravasation as a target for anti-inflammatory therapy—Which molecule to choose?", Experimental Dermatology, vol. 14, 2005, pp. 70-80.

Bos, et al. "The 500 Dalton rule for the skin penetration of chemical compounds and drugs." Exp Dermatol 2000: 9: 165-169.

Bubna et al., "Imiquimod—Its role in the treatment of cutaneous malignancies" *Indian J. Pharmacol.*, 2015, 47(4):354-359.

Cabula et al., "Electrochemotherapy in the treatment of cutaneous metastases from Breast Cancer: A multicenter Cohort Analysis," *Ann. Surg. Oncol.*, 2015, 22:S442-S450.

Campaña-Seoane et al., "Bioadhesive emulsions for control release of progesterone resistant to vaginal fluids clearance" *International Journal of Pharmaceutics*, 2014, 477:495-505.

Chambers et al., "Eruptive purpuric papules on the arms; a case of chemotherapy-induced inflammation of actinic keratosis and review of the literature," *Dermatology Online Journal*, 2014, 20(1).

De Giorgi et al., "Cutaneous manifestations of breast carcinoma," *Dermatol Therapy*, 2010, 23:581-589.

De Smet, et al. "Development of a Nanocrystalline Paclitaxel Formulation for Hipec Treatment." Pharmaceutical Research 29, 2398-2406 (2012).

DeWitte et al., "Imiquimod in cervical, vaginal and vulvar intraepithelial neoplasia: A review" *Gynecol Oncol.*, 2015, 139:377-384.

Deng, et al. "Understanding the Structure and Stability of Paclitaxel Nanocrystals." Int J Pharm May 10, 2010; 390(2): 242-249.

Desai et al. "Interaction of nanoparticles and cell-penetrating peptides with skin for transdermal drug delivery." 2010. Mol Membr Biol. 27:247-259.

Dodds et al., "Actinic Keratosis: Rationale and Management" *Dermatol Ther (Heidelb)*, 2014, 4:11-31.

Ehrlich et al., "Micellar paclitaxel improves severe psoriasis in a prospective phase II pilot study", Journal of the American Academy of Dermatology, vol. 50, 2004, pp. 533-540.

Elstad, et al. "OncoGel (ReGel/paclitaxel)—clinical applications for a novel paclitaxel delivery system." Advanced Drug Delivery Reviews 61 (2009) 785-794.

Feng, et al. "A critical review of lipid-based nanoparticles for taxane delivery." Cancer Letters 334 (2013) 157-175.

Fernandez-Anton Martinez et al., "Metastasis cutaneas de origen visceral," *Actas Dermosifiliogr.*, 2013, 104(10):841-853.

Forbes, et al. "Non-aqueous silicone elastomer gels as a vaginal microbicide delivery system for the HIV-1 entry inhibitor maraviroc." Journal of Controlled Release 156 (2011) 161-169.

Garrido et al., "Cutaneous metastates of lung cancer," *Clin. Transl. Oncol.*, 2006, 8(5):330-333.

Ghosh, et al. "Nano suspension for improving the bioavailability of a poorly soluble drug and screening of stabilizing agents to inhibit crystal growth." International Journal of Pharmaceutics 409 (2011) 260-268.

Gu, et al. (2013). "Nanoformulation of paclitaxel to enhance cancer therapy." J Biomater Appl, 28(2):298-307.

Gupta et al., "Possible role of nanocarriers in drug delivery against cervical cancer" *Nano Reviews & Experiments*, 2017, 8:1-25.

Halverstam., et al. (2008). "Nonstandard and off-label therapies for psoriasis." Clin Dermatol, 26(5):546-53.

(56) References Cited

OTHER PUBLICATIONS

Hasegawa et al., "The problems of cervical conization for postmenopausal patients" European Journal of Gynaccological Oncology, 2016, 37(3):327-331.
Heidenreich et al., "Angiogenesis drives psoriasis pathogenesis", Int. J. Exp. Path., vol. 90, 2009, pp. 232-248.
Henseler et al., "Disease concomitance in psoriasis", Journal of the American Academy of Dermatology, vol. 32, 1995, pp. 982-986.
Hosmer, et al. (2010). "Influence of internal structure and composition of liquid crystalline phases on topical delivery of paclitaxel." J Pharm Sci, 100(4):1444-1455.
Ilyas et al., "Inflammatory Actinic Keratoses Secondary to Systemic Chemotherapy," Cutis., 2005, 75:167-168.
Insinga et al., "Epidemiologic natural history and clinical management of human papillomavirus (HPV) disease: A critical and systematic review of the literature in the development of an HPV dynamic transmission model" BMC Infectious Disease, 2009, 9:119
International Preliminary Report on Patentability for PCT/US2016/052133, dated Feb. 1, 2018.
International Search Report & Written Opinion for PCT/US2016/052133, dated Mar. 24, 2017.
International Search Report and Written Opinion issued in International Patent Application No. PCT/US19/21751, dated Jun. 3, 2019.
Karande, et al. "Discovery of transdermal penetration enhancers by high-throughput screening." Nature Biotechnology vol. 22, No. 2, Feb. 2004, 192-197.
Khandavilli., et al. (2007). "Nanoemulsions as versatile formulations for paclitaxel delivery: peroral and dermal delivery studies in rats." J Invest Dermatol, 127(1):154-62.
Kilfoyle et al., "Development of paclitaxel-TyroSpheres for topical skin treatment", Journal of Controlled Release, vol. 163, No. 1, Jun. 23, 2012, pp. 18-24.
Koeneman et al., "TOPical Imiquimod treatment of high-grade Cervical intraepithelial neoplasia (TOPIC trial): study protocol for a randomized controlled trial" BMC Cancer, 2016, 16:132.
Lee et al. "Micellar delivery." 2010. Handbook nanoparticles: of non-invasive applications for topical and passive transdermal drug drug delivery. 2: 37-58.
Likes, et al., "Pilot study of sexual function and quality of life after excision of vulvar intraepithelial neoplasia," J. Reprod. Med., 2007, 52(1):23-27.
Liu, et al. (2011). "Enabling anticancer therapeutics by nanoparticle carriers: the delivery of Paclitaxel." Int J Mol Sci, 12(7):4395-413.
Lookingbill et al., "Cutaneous metastases in patients with metastatic carcinoma: A retrospective study of 4020 patients" J. Am. Acad. Dermatol., 1993, 29:228-236.
Ma et al., "Paclitaxel Nano-Delivery Systems: A Comprehensive Review", Journal of Nanomedicine and Nonotechnology, vol. 4, No. 2, 2013, pp. 1-35.
Major et al., "Vaginal drug delivery of the localized treatment of cervical cancer" Drug Delivery and Translational Research, 2017, 7:817-828.
Mak et al., "Progress in understanding the immunopathogenesis of psoriasis", Actas Dermosifiliogr, vol. 100, 2009, pp. 2-13.
Merisko-Liversidge, et al. "Formulation and Antitumor Activity Evaluation of Nanocrystalline Suspensions of Poorly Soluble Anticancer Drugs". Pharmaceutical Research, vol. 13, No. 2, 1996, 272-278.
Merisko-Liversidge, et al. "Nanosizing: a formulation approach for poorly-water-soluble compounds." European Journal of Pharmaceutical Sciences 18 (2003) 113-120.
Muller, et al. "Challenges and solutions for the delivery of biotech drugs—a review of drug nanociystal technology and lipid nanoparticles." Journal of Biotechnology 113 (2004) 151-170.
Munoz et al., "A phase II trial of the use of 4,4'-dihydroxybenzophenome-2-4-dinitrophenyl-hydrazone (A-007) topical gel in the treatment of high-grade squamous intraepithelial lesions (HSIL) of the cervix" Journal of Clinical Oncology, 2007 ASCO Annual Meeting Proceeds, 25(185):5593 (Abstract Only).

Narang et al. "Pharmaceutical development and regulatory considerations for nanoparticles and nanoparticulate drug delivery systems." 2013. Journal of Pharmaceutical Sciences.
Nickoloff et al., "Recent insights into the immunopathogenesis of psoriasis provide new therapeutic opportunities", The Journal of Clinical Investigation, vol. 113, No. 12, 2004, pp. 1164-1675.
Ojima et al., "Taxane anticancer agents: a patient perspective" Expert Opin. Ther. Patents, 2016, 26(1), 20 pages.
Okabe et al., "Percutaneous absorption enhancing effect and skin irritation of monocyclic monoterpenes" Drug Des. Deliv., 1990, 6(3):229-238.
Osborne, et al. "Skin Penetration Enhancers Cited in the Technical Literature." Pharmaceutical Technology Nov. 1997, 58-66.
Panchagnula, et al. (2004). "Effect of lipid bilayer alteration on transdermal delivery of a high-molecular-weight and lipophilic drug: studies with paclitaxel." J Pharm Sci, 93(9):2177-83.
Parisi et al., "Global Epidemiology of Psoriasis: A Systematic Review of Incidence and Prevalence", Journal of Investigative Dermatology, vol. 133, 2013, pp. 377-385.
Pepe, et al. (2013). "Protein transduction domain-containing microemulsions as cutaneous delivery systems for an anticancer agent." J Pharm Sci, 102(5): 1476-87.
Pepe, et al., "Transportan in nanocarriers improves skin localization and antitumor activity of paclitaxel" International Journal of Nanomedicine, 2016, 11:2009-2019.
Petry, "Management options for cervical intraepithelial neoplasia" Best Pract. Res. Clin. Obstet. Gynaecol., 2011, 25(5):641-651.
Prow, et al. (2011). "Nanoparticles and microparticles for skin drug delivery." Adv Drug Deliv Rev, 63(6):470-91.
Ranade, et al. (2013). paclitaxel (Nanoxel) "Clinical in India" Ann and economic implications of the use of nanoparticle Oncol, 24:v6-v12.
Reyes et al., "An update on vulvar intraepithelial neoplasia: terminology and practical approach to diagnosis" J. Clin. Pathol., 2014, 67:290-294.
Roberts, (1997). "Targeted drug delivery to the skin and deeper tissues: role of physiology, solute structure and disease." Clin Exp Pharmacol Physiol, 24(11):874-9.
Rowinsky et al., "Clinical toxicities encountered with paclitaxel (Taxol)", Seminars in Oncology, 1993, pp. 1-15.
Santesso et al., "Systematic reviews and meta-analyses of benefits and harms of cryotherapy, LEEP and cold knife conization to treat cervical intraepithelial neoplasia," Int. J. Gynecol. Obstet., 2016, 132:266-271
Second Written Opinion for PCT/US2016/052133, dated Oct. 27, 2017.
Sheihet, et al. "Tyrosine-derived nanospheres for enhanced topical skin penetration." Int J Pharm, 350(2008) 312-319.
Spratt et al., "Efficacy of Skin-Directed Therapy for Cutaneous Metastaes from Advanced Cancer: A Meta-Analysis," J. Clin. Oncol., 2014, 32:3144-3155.
Sun, et al. "Application of Nano- and Micro-Particles on the Topical Therapy of Skin-Related Immune Disorders." Current Pharmaceutical Design, 2015, 21, 2643-2667.
Surapaneni et al. "Designing Paclitaxel Drug Delivery Systems Aimed at Improved Patient Outcomes: Current Status and Challenges." ISRN Pharmacology. 2012:623139, 2012.
Van Eerdenbrugh et al., "Top-down production of drug, nanocrystals: Nanosuspension stabilization, miniaturization and transformation into solid products", International Journal of Pharmaceutics, vol. 364, No. 1, Nov. 19, 2008, pp. 64-75.
Van Seters et al., "Treatment of vulvar Intraepithelial Neoplasia with Topical Imiquimod" The New England Journal of Medicine, 2008, 358(14):1465-1473.
Varma,, et al. "Enhanced oral paclitaxel absorption with vitamin E-TPGS: effect on solubility and permeability in vitro, in situ and in vivo.." European Journal of Pharmaceutical Sciences 25(2005) 445-453.
Vaz Tosta et al., "Paclitaxel-loaded lipid nanoparticles for topical application: the influence of oil content on lipid dynamic behavior, stability, and drug skin penetration" J. Nanopart. Res., 2014, 16:2782

(56) References Cited

OTHER PUBLICATIONS

Williamson et al., "A Phase I study of Intraperitoneal nanoparticulate paclitaxel (Nanotax®) in patients with peritoneal malignancies" *Cancer Chemotherapy and Pharmacology*, 2015, 15 pages.

Wong et al., "The Presentation, Pathology, and Current Management Strategies of Cutaneous Metastasis" *North American Journal of Medical Science*, 2013, 5(9):499-504.

Worley et al., "Docetaxel Accumulates in Lymphatic Circulation Following Subcutaneous Delivery Compared to Intravenous Delivery in Rats" *Anticancer Research*, 2016, 36:5071-5078.

Wu, et al. "Physical and chemical stability of drug nanoparticles." Advanced Drug Delivery Reviews 63 (2011) 456-469.

Yang, et al. "Vaginal Delivery of Paclitaxel via Nanoparticles with Non-mucoadhesive Surfaces Suppresses Cervical Tumor Growth." Adv. Healthcare Mater. 2014, 3, 1044-1052.

Zentner, et al. "Biodegradable block copolymers for delivery of proteins and water-insoluble drugs." Journal of Controlled Release 72 (2001)203-215.

Alvarez-Roman et al., "Skin penetration and distribution of polymeric nanoparticles", *Journal of Controlled Release*, 99:53-62, 2004.

Baroli, "Penetration of Nanoparticles and Nanomaterials in the Skin: Fiction or Reality?" Journal of Pharmaceutical Sciences 2010 99(1):21-50 (Year: 2010).

International Search Report and Written Opinion issued in International Patent Application No. PCT/US2018/022540, dated Jun. 18, 2018.

International Search Report and Written Opinion issued in International Patent Application No. PCT/US2018/022553, dated Jun. 18, 2018.

International Search Report and Written Opinion issued in International Patent Application No. PCT/US2018/022557, dated Jun. 18, 2018.

Search Report and Written Opinion issued in Corresponding Singapore Patent Application No. 11201801822T, dated Jul. 1, 2019.

Patlolla et al., "Translocation of cell penetrating peptide engrafted nanoparticles across skin layers" *Biomaterials*, 31:5598-5607, 2010.

Rancan et al. "Skin Penetration and Cellular Uptake of Amorphous Silica Nanoparticles with Variable Size, Surface Functionalization, and Colloidal Stability" ACS Nano 2012 6(8):6829-6842, 2012.

Watkinson et al., "Nanoparticles Do Not Penetrate Human Skin—A Theoretical Perspective" *Pharmaceutical Research*,30:1943-1946, 2013.

Notice of Reasons for Rejection from the Japanese Patent Office issued in corresponding Patent Application No. 2018-515121 dated Jul. 30, 2020.

Doge et al., "Identification of polystyrene nanoparticle penetration across intact skin barrier as rare event at sites of focal particle aggregations" *J. Biophotonics.*, 11:e201700169, 2018.

\* cited by examiner

DELIVERY OF DRUG NANOPARTICLES AND METHODS OF USE THEREOF

CROSS-REFERENCE TO RELATED APPLICATION

This application is a continuation of U.S. patent application Ser. No. 15/899,228 filed Feb. 19, 2018, which is a continuation of PCT Application No. PCT/US2016/052133, filed Sep. 16, 2016, which claims the benefit of U.S. Provisional Application No. 62/219,453, filed Sep. 16, 2015. The contents of the referenced applications are incorporated into the present application by reference.

FIELD OF THE INVENTION

The present invention generally relates to the field of drug delivery. In particular, the invention relates to the delivery of drug nanoparticles and includes skin penetration enhancement, inhibition of crystal growth in formulations, and/or the treatment of psoriasis. Additionally, the invention relates to delivery of drug nanoparticles to keratinous tissue, plus methods of treatment of keratinous tissue diseases and conditions.

BACKGROUND OF THE INVENTION

Delivery of therapeutic drugs into viable epidermis and dermis of the skin can be a challenge due to the barrier properties of the stratum corneum, the outermost layer of the epidermis. The delivery of poorly water soluble drugs into the skin can be even more of a challenge. Skin penetration enhancers have been employed in topical drug formulations to increase the penetration of drugs into the skin and have had some success. However, some penetration enhancers such as solvents and surfactants can be irritating to the skin. Volatile silicone fluids have been employed in topical formulations to increase the penetration of drugs into the skin; however, high concentrations of volatile silicone fluids, i.e., 25% and greater, and/or combinations of volatile silicone fluids with other potential skin irritating compounds such as alcohols, e.g., $C_1$ to $C_4$ aliphatic alcohols, surfactants, other penetration enhancers, and other volatile solvents have been needed to produce the penetration enhancement effect. Additionally, some penetration enhancers will cause the drug to penetrate transdermally and be systemically absorbed, which is not desirable when only treating a condition of the skin (e.g., epidermis and/or dermis). Other topical delivery systems have been employed where the drug is chemically modified with surfactants and other substances, but these materials can also be irritating to the skin.

Taxanes, including paclitaxel and docetaxel, have been used for the treatment of cancer for many years. The cancer treatment formulation initially developed for intravenous (IV) infusion injection, TAXOL® (BMS), is paclitaxel dissolved in a 50:50 v/v mixture of polyethoxylated castor oil (CREMOPHOR® EL) and dehydrated ethanol. However, the systemic use of this formulation results in significant clinical toxicity (Rowinsky et al. 1993). Substantial effort has been devoted to the development of CREMOPHOR EL-free formulations of paclitaxel (Ma and Mumper, 2013). One such formulation is disclosed in U.S. Pat. No. 8,221,779, herein incorporated by reference, which discloses injectable aqueous compositions of antimitotic drug microparticles, including paclitaxel, useful for the treatment of cancers by intraperitoneal and intravenous (IV) injection of the compositions.

However, problems of aqueous based compositions containing drug nanoparticle crystals, including taxanes, is that many times, the drug nanoparticle crystals will grow in the aqueous based compositions while in storage. This is especially problematic for injectable dosage forms, including compositions for (IV) infusion, where the presence of large crystals in the compositions could cause serious harm to the patient.

Psoriasis is a chronic, disfiguring, immune-mediated skin disease affecting approximately 2-4% of the population worldwide (Parisi et al. 2013). This disease is characterized by excessive growth of epidermal keratinocytes and angiogenesis, as well as accumulation of inflammatory cells (Heidenreich et al. 2009; Schon and Boehncke, 2005). Psoriasis can result in erythematous skin lesions (plaques), psoriatic arthritis, and nail dystrophy; furthermore, it is associated with Crohn's disease and other systemic diseases as well as depression, thus causing significant morbidity and contributing to early mortality (Henseler and Christophers, 1995; Mak et al. 2009; Nickoloff and Nestle, 2004).

Anecdotal observations of improvements in psoriasis-afflicted cancer patients receiving paclitaxel led to the hypothesis that taxanes (e.g., paclitaxel, docetaxel) may have the potential to be used as an alternative therapy to treat psoriasis. An open-label, prospective Phase II study conducted in 12 subjects with severe psoriasis concluded that intravenous (IV) infusions of micellar (non-Cremophor EL-containing) paclitaxel over weekly time periods resulted in therapeutic activity in these patients, while being generally well tolerated (Ehrlich et al. 2004). Nonclinical evaluations disclosed in U.S. Pat. No. 6,515,016 demonstrated reduced inflammation, swelling, and erythema in skin inflammation models following treatment with topical paclitaxel. However, topical treatment of psoriasis can be especially problematic because the psoriatic plaque buildup on the skin impedes the delivery of the drug into the skin. Currently, there are no FDA approved topical taxane formulations for the treatment of psoriasis.

Treatment of diseases and conditions of keratinous tissue, including nails, the nail bed, and hair, have been difficult because of the hard protective layer of keratin which inhibits penetration of drugs to the affected tissue. Although nails are a skin appendage, nail diseases are distinct from diseases of the skin. Common diseases of the nail include onychomycosis, a fungal disease, and nail psoriasis, which often affects patients with psoriasis of the skin.

SUMMARY OF THE INVENTION

The present invention provides solutions to the aforementioned limitations and deficiencies in the art relating to drug delivery, inhibition of crystals in aqueous formulations and anhydrous, hydrophobic compositions of drug nanoparticles, and/or the treatment of psoriasis.

It was found that hydrophobic compositions of the present invention having a volatile silicone fluid at concentrations less than 25% w/w in combination with an anhydrous hydrophobic carrier exhibited greater skin penetration (i.e., penetration into the epidermal and dermal portions of the skin) of drug nanoparticles as compared to the skin penetration of drug nanoparticles from the hydrophobic carrier alone. Surprisingly, it was also discovered that, other than the low amounts of volatile silicone fluid (less than 25 w/w %), the addition of other skin penetration enhancers to the hydrophobic compositions had little or no effect on the skin penetration of the compositions. Therefore, the compositions of the present invention can be free of (do not have to include) these additional skin penetration enhancers (e.g., surfactants, volatile solvents, alcohols, $C_1$-$C_5$ aliphatic alcohols), which can be helpful in reducing skin irritation when the compositions of the present invention are applied to the skin. Even more surprising is that the enhanced penetration was accomplished with low concentrations of cyclomethicone, i.e., less than 25% w/w. Additionally, the drug nanoparticles are not transdermally delivered with these compositions initially after administration, which is a favorable feature because transdermal delivery (systemic absorption) is not desired when treating the skin (epidermis and dermis). Furthermore, the skin penetration (i.e., penetration into the dermal or epidermal portions of the skin) of drug nanoparticles from the compositions of the present invention was far superior to the skin penetration of drug nanoparticles from aqueous based compositions, even though the aqueous based compositions contained a skin penetration enhancer. Additionally, it was found that the drug nanoparticles were stable and did not exhibit crystal grow over time in the hydrophobic compositions of the present invention.

Hydrophobic compositions which comprise drug nanoparticles of a taxane, e.g., paclitaxel, and a volatile silicone fluid in combination with a hydrophobic carrier, are especially suitable for the topical treatment of psoriasis because of the enhanced penetration properties of these compositions into the epidermis and dermis portions of the skin. Notably, however, these hydrophobic compositions have reduced to no penetration transdermally, thus reducing or avoiding systemic administration of paclitaxel. Rather, the compositions of the present invention can treat psoriasis locally rather than systemically.

It was also found that crystal growth of drug nanoparticles in aqueous carriers is inhibited by the inclusion of poloxamer 407, a quaternary ammonium compound, or a cross-linked acrylic acid polymer in the aqueous carrier.

The compositions of the present invention are also useful for topical delivery of drug nanoparticles to keratinous tissue, including nails and hair, and for the treatment of diseases and conditions of keratinous tissue. The compositions of the invention which include taxane nanoparticles or antifungal nanoparticles are especially useful for the treatment of certain diseases and conditions of the nail.

Also disclosed in the context of the present invention are the following embodiments 1 to 155:

Embodiment 1 is a method of enhancing penetration of drug nanoparticles into skin, the method comprising applying to the surface of skin a hydrophobic composition comprising a continuous hydrophobic carrier, 5-24% w/w of one or more volatile silicone fluids, and a plurality of drug nanoparticles, wherein the mean particle size (number) of the drug nanoparticles is from 0.1 microns to 1.5 microns, and wherein the composition does not contain $C_1$-$C_5$ aliphatic alcohols.

Embodiment 2 is the method of embodiment 1, wherein the volatile silicone fluid is cyclomethicone.

Embodiment 3 is the method of embodiment 2, wherein the cyclomethicone is cyclopentasiloxane.

Embodiment 4 is the method of any one of embodiments 1 to 3, wherein the composition does not contain additional penetration enhancers.

Embodiment 5 is the method of any one of embodiments 1 to 4, wherein the composition does not contain additional volatile solvents.

Embodiment 6 is the method of any one of embodiments 1 to 5, wherein the composition does not contain surfactants.

Embodiment 7 is the method of any one of embodiments 1 to 6, wherein the composition is anhydrous.

Embodiment 8 is the method of any one of embodiments 1 to 7, wherein the hydrophobic carrier is non-volatile.

Embodiment 9 is the method of any one of embodiments 1 to 8, wherein the hydrophobic carrier is non-polar.

Embodiment 10 is the method of any one of embodiments 1 to 9, wherein the hydrophobic carrier comprises a hydrocarbon.

Embodiment 11 is the method of embodiment 10, wherein the hydrocarbon is petrolatum, mineral oil, or paraffin wax; or mixtures thereof.

Embodiment 12 is the method of embodiment 11, wherein the petrolatum is white petrolatum.

Embodiment 13 is the method of embodiments 11 or 12, wherein the mineral oil is heavy mineral oil.

Embodiment 14 is the method of any one of embodiments 1 to 13, wherein the drug nanoparticles are crystalline nanoparticles.

Embodiment 15 is the method of any one of embodiments 1 to 13, wherein the drug nanoparticles are amorphous nanoparticles.

Embodiment 16 is the method of any one of embodiments 1 to 13, wherein the drug nanoparticles are a combination of amorphous and crystalline nanoparticles.

Embodiment 17 is the method of any one of embodiments 1 to 16, wherein the mean particle size of the drug nanoparticles does not grow larger than 20% of the initial mean particle size when the composition is stored at room temperature for at least 1 month.

Embodiment 18 is the method of any one of embodiments 1 to 16, wherein the mean particle size of the drug nanoparticles does not grow larger than 20% of the initial mean particle size when the composition is stored at room temperature for at least 3 months.

Embodiment 19 is the method of any one of embodiments 1 to 18, wherein the drug nanoparticles are water soluble.

Embodiment 20 is the method of any one of embodiments 1 to 18, wherein the drug nanoparticles are poorly water soluble.

Embodiment 21 is the method of embodiment 20, wherein the drug nanoparticles are taxane nanoparticles.

Embodiment 22 is the method of embodiment 21, wherein the taxane nanoparticles are paclitaxel nanoparticles, docetaxel nanoparticles, or cabazitaxel nanoparticles.

Embodiment 23 is the method of embodiment 21, wherein the taxane nanoparticles are paclitaxel nanoparticles.

Embodiment 24 is the method of any one of embodiments 1 to 23, wherein the skin is diseased skin.

Embodiment 25 is the method of embodiment 24, wherein the diseased skin is psoriatic skin.

Embodiment 26 is the method of any one of embodiments 1 to 25, wherein less than 0.01 $\mu g/cm^2$ of the drug nanoparticles penetrate through human cadaver skin when the composition is applied to the human cadaver skin as determined by an in vitro Franz diffusion cell system.

Embodiment 27 is the method of any one of embodiments 1 to 26, wherein the composition is a semi-solid composition.

Embodiment 28 is the method of embodiment 27, wherein the semi-solid composition is an ointment.

Embodiment 29 is the method of embodiment 27 or 28, wherein the viscosity of the composition is from 12,500 cps to 247,500 cps as measured at room temperature by a Brookfield RV viscometer using a small sample adapter with a $SC_4$-14 spindle and a 6R chamber at 5 rpm with an equilibration time of 2 minutes.

Embodiment 30 is a hydrophobic composition comprising a continuous hydrophobic carrier, 5-24% w/w of one or more volatile silicone fluids, and a plurality of drug nanoparticles, wherein the mean particle size (number) of the drug nanoparticles is from 0.1 microns to 1.5 microns, and wherein the composition does not contain $C_1$-$C_5$ aliphatic alcohols.

Embodiment 31 is the composition of embodiment 30, wherein the volatile silicone fluid is cyclomethicone.

Embodiment 32 is the composition of embodiment 31, wherein the cyclomethicone is cyclopentasiloxane.

Embodiment 33 is the composition of any one of embodiments 30 to 32, wherein the composition does not contain additional penetration enhancers.

Embodiment 34 is the composition of any one of embodiments 30 to 33, wherein the composition does not contain additional volatile solvents.

Embodiment 35 is the composition of any one of embodiments 30 to 34, wherein the composition does not contain surfactants.

Embodiment 36 the composition of any one of embodiments 30 to 35, wherein the composition is anhydrous.

Embodiment 37 is the composition of any one of embodiments 30 to 36, wherein the hydrophobic carrier is non-volatile.

Embodiment 38 is the composition of any one of embodiments 30 to 37, wherein the hydrophobic carrier is non-polar.

Embodiment 39 is the composition of any one of embodiments 30 to 38, wherein the hydrophobic carrier comprises a hydrocarbon.

Embodiment 40 is the composition of embodiment 39, wherein the hydrocarbon is petrolatum, mineral oil, or paraffin wax; or mixtures thereof.

Embodiment 41 is the composition of embodiment 40, wherein the petrolatum is white petrolatum.

Embodiment 42 is the composition of embodiment 40 or 41, wherein the mineral oil is heavy mineral oil.

Embodiment 43 is the composition of any one of embodiments 30 to 42, wherein the drug nanoparticles are crystalline nanoparticles.

Embodiment 44 is the composition of any one of embodiments 30 to 42, wherein the drug nanoparticles are amorphous nanoparticles.

Embodiment 45 is the composition of any one of embodiments 30 to 42, wherein the drug nanoparticles are a combination of amorphous and crystalline nanoparticles.

Embodiment 46 is the composition of any one of embodiments 30 to 45, wherein the mean particle size of the drug nanoparticles does not grow larger than 20% of the initial mean particle size when the composition is stored at room temperature for at least 1 month.

Embodiment 47 is the composition of any one of embodiments 30 to 45, wherein the mean particle size of the drug nanoparticles does not grow larger than 20% of the initial mean particle size when the composition is stored at room temperature for at least 3 months.

Embodiment 48 is the composition of any one of embodiments 30 to 47, wherein the drug nanoparticles are water soluble.

Embodiment 49 is the composition of any one of embodiments 30 to 47, wherein the drug nanoparticles are poorly water soluble.

Embodiment 50 is the composition of embodiment 49, wherein the drug nanoparticles are taxane nanoparticles.

Embodiment 51 is the composition of embodiment 50, wherein the taxane nanoparticles are paclitaxel nanoparticles, docetaxel nanoparticles, or cabazitaxel nanoparticles.

Embodiment 52 is the composition of embodiment 50, wherein the taxane nanoparticles are paclitaxel nanoparticles.

Embodiment 53 is the composition of any one of embodiments 30 to 52, wherein less than 0.01 μg/cm² of the drug nanoparticles penetrate through human cadaver skin when the composition is applied to the human cadaver skin as determined by an in vitro Franz diffusion cell system.

Embodiment 54 is the composition of any one of embodiments 30 to 53, wherein the composition is a semi-solid composition.

Embodiment 55 is the composition of embodiment 54, wherein the semi-solid composition is an ointment.

Embodiment 56 is the composition of embodiments 54 or 55, wherein the viscosity of the composition is from 12,500 cps to 247,500 cps as measured at room temperature by a Brookfield RV viscometer using a small sample adapter with a $SC_4$-14 spindle and a 6R chamber at 5 rpm with an equilibration time of 2 minutes.

Embodiment 57 is a method of treating psoriasis in a patient, the method comprising topically administering to the affected area of the patient a continuous hydrophobic composition comprising a hydrophobic carrier, 5-24% w/w of one or more volatile silicone fluids, and a plurality of taxane nanoparticles, wherein the mean particle size (number) of the taxane nanoparticles is from 0.1 microns to 1.5 microns, wherein the composition does not contain $C_1$-$C_5$ aliphatic alcohols, and wherein the concentration of the taxane nanoparticles is at a concentration effective to provide a therapeutic improvement in the psoriatic condition.

Embodiment 58 is the method of embodiment 57, wherein the taxane nanoparticles are paclitaxel nanoparticles, docetaxel nanoparticles, or cabazitaxel nanoparticles.

Embodiment 59 is the method of embodiment 57, wherein the taxane nanoparticles are paclitaxel nanoparticles.

Embodiment 60 is the method of any one of embodiments 57 to 59, wherein the volatile silicone fluid is cyclomethicone.

Embodiment 61 is the method of embodiment 60, wherein the cyclomethicone is cyclopentasiloxane.

Embodiment 62 is the method of any one of embodiments 57 to 61, wherein the composition does not contain additional penetration enhancers.

Embodiment 63 is the method of any one of embodiments 57 to 62, wherein the composition does not contain additional volatile solvents.

Embodiment 64 is the method of any one of embodiments 57 to 63, wherein the composition does not contain surfactants.

Embodiment 65 is the method of any one of embodiments 57 to 64, wherein the composition is anhydrous.

Embodiment 66 is the method of any one of embodiments 57 to 65, wherein the hydrophobic carrier is non-volatile.

Embodiment 67 is the method of any one of embodiments 57 to 66, wherein the hydrophobic carrier is non-polar.

Embodiment 68 is the method of any one of embodiments 57 to 67, wherein the hydrophobic carrier comprises a hydrocarbon.

Embodiment 69 is the method of embodiment 68, wherein the hydrocarbon is petrolatum, mineral oil, or paraffin wax; or mixtures thereof.

Embodiment 70 is the method of embodiment 69, wherein the petrolatum is white petrolatum.

Embodiment 71 is the method of embodiment 69 or 70, wherein the mineral oil is heavy mineral oil.

Embodiment 72 is the method of any one of embodiments 57 to 71, wherein the taxane nanoparticles are crystalline nanoparticles.

Embodiment 73 is the method of any one of embodiments 57 to 71, wherein the taxane nanoparticles are amorphous nanoparticles.

Embodiment 74 is the method of any one of embodiments 57 to 71, wherein the taxane nanoparticles are a combination of amorphous and crystalline nanoparticles.

Embodiment 75 is the method of any one of embodiments 57 to 74, wherein the mean particle size of the taxane nanoparticles does not grow larger than 20% of the initial mean particle size when the composition is stored at room temperature for at least 3 months.

Embodiment 76 is the method of any one of embodiments 57 to 75, wherein less than 0.01 µg/cm² of the taxane nanoparticles penetrate through human cadaver skin when the composition is applied to the human cadaver skin as determined by an in vitro Franz diffusion cell system.

Embodiment 77 is the method of any one of embodiments 57 to 76, wherein the composition is a semi-solid composition.

Embodiment 78 is the method of embodiment 77, wherein the semi-solid composition is an ointment.

Embodiment 79 is the method of embodiments 77 or 78, wherein the viscosity of the composition is from 12,500 cps to 247,500 cps as measured at room temperature by a Brookfield RV viscometer using a small sample adapter with a $SC_4$-14 spindle and a 6R chamber at 5 rpm with an equilibration time of 2 minutes.

Embodiment 80 is a method of inhibiting the growth of crystalline drug nanoparticles, the method comprising contacting drug nanoparticles with a hydrophobic carrier, wherein the mean particle size (number) of the drug nanoparticles is from 0.1 microns to 1.5 microns.

Embodiment 81 is the method of embodiment 80, wherein the drug nanoparticles are water soluble.

Embodiment 82 is the method of embodiment 80, wherein the drug nanoparticles are poorly water soluble.

Embodiment 83 is the method of embodiment 82, wherein the drug nanoparticles are taxane nanoparticles.

Embodiment 84 is the method of embodiment 83, wherein the taxane nanoparticles are paclitaxel nanoparticles, docetaxel nanoparticles, or cabazitaxel nanoparticles.

Embodiment 85 is the method of embodiment 83, wherein the taxane nanoparticles are paclitaxel particles.

Embodiment 86 is the method of any one of embodiments 80 to 85, wherein the hydrophobic carrier is anhydrous.

Embodiment 87 is the method of any one of embodiments 80 to 85, wherein the hydrophobic carrier comprises a hydrocarbon.

Embodiment 88 is the method of embodiment 87, wherein the hydrocarbon is petrolatum, mineral oil, or paraffin wax; or mixtures thereof.

Embodiment 89 is the method of any of embodiments 80 to 88, wherein the compositions further comprises one or more volatile silicone fluid.

Embodiment 90 is the method of embodiment 89, wherein the volatile silicone fluid is a cyclomethicone.

Embodiment 91 is the method of embodiment 90, wherein the cyclomethicone is cyclopentasiloxane.

Embodiment 92 is a method of inhibiting the growth of a dispersion of poorly water soluble crystalline drug nanoparticles in an aqueous based carrier, the method comprising adding poloxamer 407, a quaternary ammonium compound, or a cross-linked acrylic acid polymer, or mixtures thereof, to the aqueous based carrier during processing, wherein the mean particle size (number) of the drug nanoparticles is from 0.1 microns to 1.5 microns.

Embodiment 93 is the method of embodiment 92, wherein the quaternary ammonium compound is benzalkonium chloride or benzethonium chloride.

Embodiment 94 is the method of embodiment 92, wherein the cross-linked acrylic acid polymer is carbomer.

Embodiment 95 is the method of any of embodiments 92 to 94, wherein the drug nanoparticles are taxane nanoparticles.

Embodiment 96 is the method of embodiment 95, wherein the taxane nanoparticles are paclitaxel nanoparticles, docetaxel nanoparticles, or cabazitaxel nanoparticles.

Embodiment 97 is the method of embodiment 95, wherein the taxane nanoparticle are paclitaxel nanoparticles.

Embodiment 98 is a method of topically treating a disease or condition of keratinous tissue, the method comprising topically administering to the keratinous tissue a hydrophobic composition comprising a continuous hydrophobic carrier, 5-24% w/w of one or more volatile silicone fluids, and a plurality of drug nanoparticles, wherein the mean particle size (number) of the drug nanoparticles is from 0.1 microns to 1.5 microns, wherein the concentration of the drug nanoparticles is at a concentration effective to provide a therapeutic improvement in the disease or condition, and wherein the composition does not contain $C_1$-$C_5$ aliphatic alcohols.

Embodiment 99 is the method of embodiment 98, wherein the volatile silicone fluid is a cyclomethicone.

Embodiment 100 is the method of embodiment 99, wherein the cyclomethicone is cyclopentasiloxane.

Embodiment 101 is the method of any one of embodiments 98 to 100, wherein the composition does not contain additional penetration enhancers.

Embodiment 102 is the method of any one of embodiments 98 to 101, wherein the composition does not contain additional volatile solvents.

Embodiment 103 is the method of any one of embodiments 98 to 102, wherein the composition does not contain surfactants.

Embodiment 104 is the method of any one of embodiments 98 to 103, wherein the composition is anhydrous.

Embodiment 105 is the method of any one of embodiments 98 to 104, wherein the hydrophobic carrier is non-volatile.

Embodiment 106 is the method of any one of embodiments 98 to 105, wherein the hydrophobic carrier is non-polar.

Embodiment 107 is the method of any one of embodiments 98 to 106, wherein the hydrophobic carrier comprises a hydrocarbon.

Embodiment 108 is the method of embodiment 107, wherein the hydrocarbon is petrolatum, mineral oil, or paraffin wax; or mixtures thereof.

Embodiment 109 is the method of embodiment 107, wherein the petrolatum is white petrolatum.

Embodiment 110 is the method of embodiments 108 or 109, wherein the mineral oil is heavy mineral oil.

Embodiment 111 is the method of any one of embodiments 98 to 110, wherein the drug nanoparticles are crystalline nanoparticles.

Embodiment 112 is the method of any one of embodiments 98 to 110, wherein the drug nanoparticles are amorphous nanoparticles.

Embodiment 113 is the method of any one of embodiments 98 to 110, wherein the drug nanoparticles are a combination of amorphous and crystalline nanoparticles.

Embodiment 114 is the method of any one of embodiments 98 to 113, wherein the mean particle size of the drug nanoparticles does not grow larger than 20% of the initial mean particle size when the composition is stored at room temperature for at least 1 month.

Embodiment 115 is the method of any one of embodiments 98 to 113, wherein the mean particle size of the drug nanoparticles does not grow larger than 20% of the initial mean particle size when the composition is stored at room temperature for 3 months.

Embodiment 116 is the method of any one of embodiments 98 to 115, wherein the drug nanoparticles are water soluble.
Embodiment 117 is the method of any one of embodiments 98 to 115, wherein the drug nanoparticles are poorly water soluble.
Embodiment 118 is the method of embodiment 117, wherein the drug nanoparticles are taxane nanoparticles.
Embodiment 119 is the method of embodiment 118, wherein the taxane nanoparticles are paclitaxel nanoparticles, docetaxel nanoparticles, or cabazitaxel nanoparticles.
Embodiment 120 is the method of embodiment 118, wherein the taxane nanoparticles are paclitaxel nanoparticles.
Embodiment 121 is the method of any one of embodiments 98 to 117, wherein the drug nanoparticles are nanoparticles of antifungal agents.
Embodiment 122 is the method of any one of embodiments 98 to 121, wherein the composition is a semi-solid composition.
Embodiment 123 is the method of embodiment 122, wherein the semi-solid composition is an ointment.
Embodiment 124 is the method of embodiment 122 or 123, wherein the viscosity of the composition is from 12,500 cps to 247,500 cps as measured at room temperature by a Brookfield RV viscometer using a small sample adapter with a $SC_4$-14 spindle and a 6R chamber at 5 rpm with an equilibration time of 2 minutes.
Embodiment 125 is the method of any one of embodiments 98 to 124, wherein the disease or condition of the keratinous tissue is nail psoriasis.
Embodiment 126 is the method of any one of embodiments 98 to 124, wherein the disease or condition of the keratinous tissue is a fungal infection.
Embodiment 127 is the method of embodiment 126, wherein the fungal infection is onychomycosis.
Embodiment 128 is the method of any one of embodiments 98 to 127, wherein the keratinous tissue is the nails or the nail bed, or both.
Embodiment 129 is the method of any one of embodiments 98 to 124, or 126, wherein the keratinous tissue is hair.
Embodiment 130 is an aqueous based composition comprising an aqueous carrier; a plurality of poorly water soluble drug nanoparticles; and a quaternary ammonium compound, or a cross-linked acrylic acid polymer, or mixtures thereof; wherein the mean particle size (number) of the drug nanoparticles is from 0.1 microns to 1.5 microns, and wherein the mean particle size of the drug nanoparticles does not grow larger than 20% of the initial mean particle size when the composition is stored at room temperature for at least 6 months.
Embodiment 131 is the composition of embodiment 130, wherein the composition further comprises poloxamer 407.
Embodiment 132 is the method of any one of embodiments 1 to 29, 57 to 79, or 98 to 129, wherein the hydrophobic carrier is greater than 50% w/w of the composition.
Embodiment 133 is the composition of any one of embodiments 30 to 56, wherein the hydrophobic carrier is greater than 50% w/w of the composition.
Embodiment 134 is the method of any one of embodiments 27, 28, 77, 78, 122, or 123, wherein the viscosity of the composition is 25,000 cps to 500,000 cps as measured with a Brookfield RV viscometer on a helipath stand with the helipath on, with a T-E spindle at 10 RPM at room temperature for 45 seconds.
Embodiment 135 is the composition of any one of embodiments 54 or 55, wherein the viscosity of the composition is 25,000 cps to 500,000 cps as measured with a Brookfield RV viscometer on a helipath stand with the helipath on, with a T-E spindle at 10 RPM at room temperature for 45 seconds.
Embodiment 136 is the method of any one of embodiments 23, 59, 85, 97, or 120, wherein the paclitaxel nanoparticles have a specific surface area (SSA) of at least 18 $m^2$/g.
Embodiment 137 is the composition of embodiment 52, wherein the paclitaxel nanoparticles have a specific surface area (SSA) of at least 18 $m^2$/g.
Embodiment 138 is the method of embodiment 59, wherein the concentration of the paclitaxel nanoparticles is about 0.1 to about 2% w/w.
Embodiment 139 is the composition of embodiment 52, wherein the concentration of the paclitaxel nanoparticles is about 0.1 to about 2% w/w.
Embodiment 140 is the method of any one of embodiments 1 to 29, 57 to 79, 80 to 91, 92 to 97, or 98 to 129, wherein the composition does not contain a protein or albumin.
Embodiment 141 is the composition of any one of embodiments 30 to 56, or 130 to 131, wherein the composition does not contain a protein or albumin.
Embodiment 142 is the composition of embodiment 130 or 131, wherein the drug nanoparticles are taxane nanoparticles.
Embodiment 143 is the composition of embodiment 142, wherein the taxane nanoparticles are paclitaxel nanoparticles, docetaxel nanoparticles, or cabazitaxel nanoparticles.
Embodiment 144 is the composition of embodiment 142, wherein the taxane nanoparticles are paclitaxel nanoparticles.
Embodiment 145 is the composition of any of embodiments 142 to 144, wherein the composition does not contain a protein or albumin.
Embodiments 146 is a method of enhancing penetration of drug nanoparticles into skin, the method comprising applying to the surface of skin a hydrophobic composition consisting essentially of a continuous hydrophobic carrier, 5-24% w/w of one or more volatile silicone fluids, and a plurality of drug nanoparticles,
wherein the mean particle size (number) of the drug nanoparticles is from 0.1 microns to 1.5 microns;
wherein the volatile silicone fluid is cyclopentasiloxane;
wherein the continuous hydrophobic carrier is non-volatile and non-polar, greater than 50% w/w of the composition, and consists essentially of petrolatum, heavy mineral oil, and paraffin wax;
wherein the composition is an anhydrous, non-polar semi-solid ointment; and
wherein the composition does not contain $C_1$-$C_5$ aliphatic alcohols.
Embodiment 147 is the method of embodiment 146, wherein:
other than cyclopentasiloxane, the hydrophobic composition does not contain an additional skin penetration enhancer nor an additional volatile solvent; and
the hydrophobic composition does not contain a surfactant.
Embodiment 148 is the method any one of embodiments 146 or 147, wherein the drug nanoparticles are paclitaxel nanoparticles, wherein the paclitaxel nanoparticles are at a concentration of about 0.1 to about 2% w/w, and wherein the composition does not contain a protein or albumin.
Embodiment 149 is a hydrophobic composition consisting essentially of a continuous hydrophobic carrier, 5-24% w/w of one or more volatile silicone fluids, and a plurality of drug nanoparticles,
wherein the mean particle size (number) of the drug nanoparticles is from 0.1 microns to 1.5 microns;
wherein the volatile silicone fluid is cyclopentasiloxane;

wherein the continuous hydrophobic carrier is non-volatile and non-polar, greater than 50% w/w of the composition, and consists essentially of petrolatum, heavy mineral oil, and paraffin wax;

wherein the composition is an anhydrous semi-solid ointment; and wherein the composition does not contain $C_1$-$C_5$ aliphatic alcohols.

Embodiment 150 is the hydrophobic composition of embodiment 149, wherein:

other than cyclopentasiloxane, the hydrophobic composition does not contain an additional skin penetration enhancer nor an additional volatile solvent; and the hydrophobic composition does not contain a surfactant.

Embodiment 151 is the composition of any one of embodiments 149 or 150, wherein the drug nanoparticles are paclitaxel nanoparticles, wherein the paclitaxel nanoparticles are at a concentration of about 0.1 to about 2% w/w, and wherein the composition does not contain a protein or albumin.

Embodiment 152 is a method of treating psoriasis in a patient, the method comprising topically administering to the affected area of the patient a hydrophobic composition comprising a continuous hydrophobic carrier, 5-24% w/w of one or more volatile silicone fluids, and a plurality of paclitaxel nanoparticles, wherein the mean particle size (number) of the paclitaxel nanoparticles is from 0.1 microns to 1.5 microns;

wherein the volatile silicone fluid is cyclopentasiloxane;

wherein the continuous hydrophobic carrier is non-volatile and non-polar, greater than 50% w/w of the composition, and consists essentially of petrolatum, heavy mineral oil, and paraffin wax;

wherein the composition is an anhydrous semi-solid ointment:wherein the composition does not contain $C_1$-$C_5$ aliphatic alcohols;

wherein the composition does not contain a protein or albumin;

wherein the concentration of the paclitaxel nanoparticles is about 0.1 to about 2% w/w; and wherein a therapeutic improvement in the psoriatic condition is achieved.

Embodiment 153 is the method of embodiment 152, wherein the concentration of the paclitaxel nanoparticles is about 0.1 to about 0.2% w/w.

Embodiment 154 is the method of any one of embodiments 152 or 153, wherein other than cyclopentasiloxane, the hydrophobic composition does not contain an additional skin penetration enhancer nor an additional volatile solvent; and the hydrophobic composition does not contain a surfactant.

Embodiment 155 is the method of embodiment 138, wherein the concentration of the paclitaxel nanoparticles is about 0.1 to about 0.2% w/w.

The terms "nanoparticle," nanoparticles," and nanoparticulate", as used herein with regard to drug particles, represent the mean particle size (based on the number-weighted differential distribution, designated as "number") of the drug particles which is from 0.01 microns to 1.5 microns (10 nm to 1500 nm) or preferably from 0.1 microns to 1.5 microns (100 nm to 1500 nm).

The term "water soluble," as used herein, describes compounds that have a solubility in water of greater than 10 mg/mL or greater at room temperature.

The term "poorly water soluble," as used herein, describes compounds that have a solubility in water of less than or equal to 10 mg/mL at room temperature.

The term "hydrophobic," as used herein, describes compounds, compositions, or carriers that have a solubility in water of less than or equal to 10 mg/mL at room temperature.

The term "volatile," as used herein, describes compounds, compositions, or carriers that have a vapor pressure greater than or equal to 10 Pa at room temperature.

The term "non-volatile," as used herein, describes compounds, compositions, or carriers that have a vapor pressure less than 10 Pa at room temperature.

The term "anhydrous," as used herein with regard to the compositions or carriers of the invention, means that less than 3% w/w/, preferably less than 2% w/w/, more preferably less than 1% w/w, or most preferably 0% w/w/is present in the compositions or carries. This can account for small amounts of water being present (e.g., water inherently contained in any of the ingredients of the compositions or carriers, water contracted from the atmosphere, etc.).

The term "skin" as used herein means the epidermis and the dermis.

The term "room temperature" (RT) as used herein, means 20-25° C.

The term "penetration enhancer" or "skin penetration enhancer" as used herein, means a compound or a material or a substance that facilitates drug absorption into the skin (epidermis and dermis).

The term "surfactant" or "surface active agent" as used herein, means a compound or a material or a substance that exhibits the ability to lower the surface tension of water or to reduce the interfacial tension between two immiscible substances.

Unless otherwise specified, the percent values expressed herein are weight by weight and are in relation to the weight of the total composition.

The term "about" or "approximately" are defined as being close to as understood by one of ordinary skill in the art. In one non-limiting embodiment the terms are defined to be within 10%, preferably within 5%, more preferably within 1%, and most preferably within 0.5%.

For this application, a number value with one or more decimal places can be rounded to the nearest whole number using standard rounding guidelines, i.e. round up if the number being rounded is 5, 6, 7, 8, or 9; and round down if the number being rounded is 0, 1, 2, 3, or 4. For example, 3.7 can be rounded to 4.

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The use of the word "a" or "an" when used in conjunction with the terms "comprising," "having," "including," or "containing" (or any variations of these words) may mean "one," but it is also consistent with the meaning of "one or more," "at least one," and "one or more than one."

The compositions and methods for their use can "comprise," "consist essentially of," or "consist of" any of the ingredients or steps disclosed throughout the specification. With respect to the phrase "consisting essentially of," a basic and novel property of the hydrophobic compositions of the present invention are their ability to penetrate into the epidermal and dermal layers of the skin with limited to no penetration transdermally. This can be achieved without the use of $C_1$-$C_5$ aliphatic alcohols, surfactants, and additional skin penetration enhancers and additional volatile solvents other than a volatile silicone fluid(s) (e.g., cyclomethicone or cyclopentasiloxane, or a combination thereof).

"Limited," "reduced," or "minimal" when modifying the phrase "penetration transdermally" means wherein less than 0.01 µg/cm$^2$ of the drug nanoparticles penetrate through human cadaver skin when the composition is applied to the human cadaver skin as determined by an in vitro Franz diffusion cell system.

It is contemplated that any embodiment discussed in this specification can be implemented with respect to any method or composition of the invention, and vice versa. Furthermore, compositions of the invention can be used to achieve methods of the invention.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DETAILED DESCRIPTION OF THE INVENTION

Figure 1:
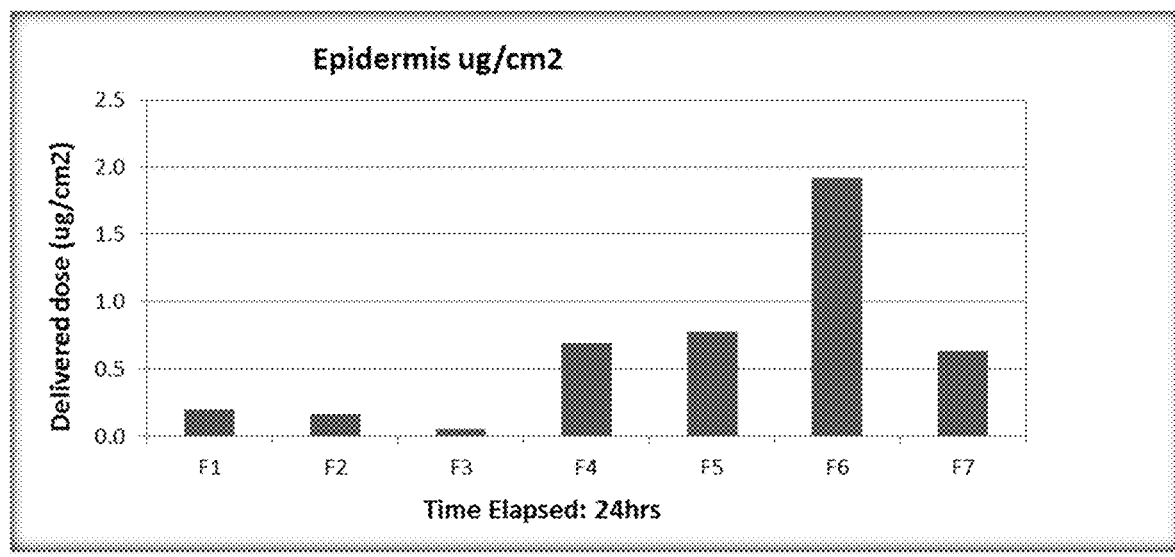
FIG. 1 graphically shows the concentration of paclitaxel (µg/cm2) delivered in vitro into the epidermis for formulas F1 through F7.

In one aspect, the invention relates to compositions and methods useful for enhancing skin penetration of drug nanoparticles into the epidermal and dermal portions of the skin. In another aspect, the invention relates to the inhibition of crystal growth of drug nanoparticles in carriers. In another aspect, the invention relates to compositions and methods useful for the topical treatment of immune-mediated diseases such as psoriasis. In another aspect, the invention relates to compositions and methods for delivery of drug nanoparticles to keratinous tissue, including nail and hair. In another aspect, the invention relates to compositions and methods for the topical treatment of keratinous tissue, including nail and hair. The compositions of the invention comprise a plurality of drug nanoparticles in a carrier. The carrier can be hydrophobic based or aqueous based.

I. Compositions

In one aspect of the invention, the compositions of the present invention are hydrophobic and comprise a continuous hydrophobic carrier, one or more volatile silicone fluids (such as cyclomethicone), and drug nanoparticles. The compositions are suspensions of a plurality of the drug nanoparticles within a mixture of the hydrophobic carrier and the volatile silicone fluid. The drug nanoparticles can be completely dispersed, or partially dispersed and partially dissolved in the compositions, but are not completely dissolved in the compositions. The hydrophobic compositions can be anhydrous. The hydrophobic carrier is the continuous phase of the compositions. Therefore, the compositions of the present invention can include at least two phases, a continuous hydrophobic carrier phase and a suspended drug nanoparticle phase. The volatile silicone fluid can be solubilized within the continuous phase.

Surprisingly, the hydrophobic compositions of the invention that include volatile silicone fluids at low concentrations, i.e., less than 25% w/w, in combination with a continuous, anhydrous hydrophobic carrier, exhibited greater skin penetration (i.e., penetration into the epidermal and/or dermal portions of the skin) of drug nanoparticles as compared to the skin penetration of drug nanoparticles from the hydrophobic carrier alone. In fact, and even more surprising, the addition of other skin penetration enhancers had little or no effect on the skin penetration of these compositions. Notably, however, the drug nanoparticles did not penetrate through the skin (i.e., transdermal penetration) or only a negligible amount penetrated transdermally through the skin, i.e. less than 0.01 µg/cm$^2$. Furthermore, the skin penetration (i.e., epidermal or dermal penetration) of drug nanoparticles from the anhydrous hydrophobic compositions was far superior to the skin penetration of drug nanoparticles from aqueous based compositions even though the aqueous based compositions contained a skin penetration enhancer. Additionally, and also surprisingly, the hydrophobic compositions of the invention that include less than 25% of a volatile silicone fluid in combination with a hydrophobic carrier, do not need to contain alcohols, additional volatile solvents, additional penetration enhancers, or surfactants to provide enhanced skin penetration, thereby allowing for a most cost-efficient and simplified composition that can have reduced skin irritancy when topically applied. If desired, however, such components can be included in the compositions of the present invention. In some embodiments, the hydrophobic compositions are free of/do not include or contain additional penetration enhancers. In other embodiments, the hydrophobic compositions are free of/do not include or contain additional volatile solvents or compounds. In some embodiments, the hydrophobic compositions are free of/do not include or contain alcohol or $C_1$-$C_5$ aliphatic alcohols. In other embodiments, the hydrophobic compositions are free of/do not include or contain surfactants. In various embodiments, the volatile silicone fluid is a cyclomethicone. In other embodiments, the cyclomethicone is cyclopentasiloxane. In some embodiments, the hydrophobic compositions are semi-solid compositions. In other embodiments the hydrophobic compositions are ointments. In some embodiments, the hydrophobic compositions are not sprays and are not sprayable.

In some embodiments, the hydrophobic compositions are semi-solid compositions, including ointments, and have a viscosity of from 12,500 cps to 247,500 cps, or from 25,000 cps to 150,000 cps as measured at room temperature by a Brookfield RV viscometer using a small sample adapter with a $SC_4$-14 spindle and a 6R chamber at 5 rpm with an equilibration time of 2 minutes. An alternative method for performing viscosity measurements of the hydrophobic, semi-solid compositions is using a Brookfield RV viscometer on a helipath stand with the helipath on, with a T-E spindle at 10 RPM at room temperature for 45 seconds. In some embodiments, the hydrophobic compositions are semi-solid compositions, including ointments, and have a viscosity of from 25,000 cps to 500,000 cps, or from 25,00 cps to 400,000 cps, or from 25,000 cps to 350,000 cps, or from 25,000 cps to 300,000 cps, or from 50,000 cps to 500,000 cps, or from 50,000 cps to 400,000 cps, or from 50,000 cps to 350,000 cps, or from 50,000 cps to 300,000 cps, or from 75,000 cps to 500,000 cps, or from 75,000 cps to 400,000 cps, or from 75,000 cps to 350,000 cps, or from 75,000 cps to 300,000 cps, or from 100,000 cps to 500,000 cps, or from 100,000 cps to 400,000 cps, or from 100,000 cps to 350,000 cps, or from 100,000 cps to 300,000 cps using a Brookfield RV viscometer on a helipath stand with the helipath on, with a T-E spindle at 10 RPM at room temperature for 45 seconds.

In another aspect, the invention relates to compositions that inhibit crystal growth of drug nanoparticles in carriers. In some embodiments, inhibition of crystal growth of drug nanoparticles in carriers is accomplished by inclusion of the nanoparticles in a hydrophobic carrier. In some embodiments, the hydrophobic carriers comprise a hydrocarbon. In some embodiments, the hydrophobic carriers comprise petrolatum, mineral oil, and/or paraffin. In some embodiments, the mineral oil is heavy mineral oil. In other embodiments, the hydrophobic carriers further comprise one or more volatile silicone fluids. In still other embodiments, the volatile silicone fluid is cyclomethicone. In other embodiments, the cyclomethicone is cyclopentasiloxane. In other embodiments, inhibition of crystal growth of drug nanoparticles in aqueous carriers is accomplished by inclusion of the nanoparticles in an aqueous carrier comprising poloxamer 407, a quaternary ammonium compound, or a cross-linked acrylic acid polymer, or mixtures thereof.

The compositions of the present invention can be formulated in various forms suitable for pharmaceutical and topical delivery. Non-limiting examples include semi-solid compositions, lotions, liquid suspensions, emulsions, creams, gels, ointments, pastes, aerosol sprays, aerosol foams, non-aerosol sprays, non-aerosol foams, films, and sheets. Semi-solid compositions include ointments, pastes, and creams. For purposes of this invention, semi-solid compositions are not sprayable. The compositions can be impregnated in gauzes, bandages, or other skin dressing materials. In some embodiments, the compositions are semi-solid compositions. In some embodiments, the compositions are ointments. In other embodiments, the compositions are gels. In still other embodiments, the compositions are liquid suspensions. In some embodiments, the compositions are not sprays and are not sprayable.

The compositions of the present invention can be packaged in any package configuration suitable for topical products. Non-limiting examples include bottles, bottles with pumps, toddles, tubes (aluminum, plastic or laminated), jars, non-aerosol pump sprayers, aerosol containers, pouches, and packets. The packages can be configured for single-dose or multiple-dose administration.

In various embodiments, the compositions of the invention are hydrophobic. In other embodiments, the hydrophobic compositions are anhydrous. In various embodiments, the hydrophobic carriers are non-polar and/or non-volatile. In still other embodiments, the compositions are aqueous based. In other embodiments, the compositions of the invention are sterile. In other embodiments, the hydrophobic compositions are non-sterile. In other embodiments, the hydrophobic compositions have a low bioburden. In various embodiments, the hydrophobic compositions of the invention do not contain additional skin penetration enhancers. In other embodiments, the hydrophobic compositions of the invention do not contain additional volatile solvents. In still other embodiments, the hydrophobic compositions of the invention do not contain surfactants. In other embodiments, the hydrophobic compositions of the invention do not contain alcohols or $C_1$-$C_5$ aliphatic alcohols.

A. Drug Nanoparticles

The drug nanoparticles of the present invention are particles of physiologically active pharmaceutical ingredients (APIs) that have a mean particle size (number) of from 0.1 microns to 1.5 microns (100 nanometers to 1500 nanometers), or from 0.01 microns to 1.5 microns as determined by a particle size analyzer instrument such as one discussed below. In some embodiments, the drug nanoparticles have a mean particle size (number) of from 0.01 microns to 1.5 microns. In other embodiments, the drug nanoparticles have a mean particle size (number) of from 0.01 microns to 1.2 microns, or from 0.01 microns to less than 1 micron, or from 0.01 microns to 1 micron. In still other embodiments, the drug nanoparticles have a mean particle size (number) of from 0.05 microns to 1.5 microns, or from 0.05 microns to 1.2 microns, or from 0.05 microns to less than 1 micron, or from 0.05 microns to 1 micron. In various embodiments, the drug nanoparticles have a mean particle size (number) of from 0.1 microns to 1.5 microns, or from 0.1 microns to 1.2 microns, or from 0.1 microns to less than 1 micron, or from 0.1 microns to 1 micron, or from 0.4 microns to 1.5 microns, or from 0.4 microns to 1.2 microns, or from 0.4 microns to less than 1 micron, or from 0.4 microns to 1 micron, or from 0.6 microns to 1.5 microns, or from 0.6 microns to 1.2 microns, or from 0.6 to less than 1 micron, or from 0.6 microns to 1 micron. In some embodiments, the drug nanoparticles of the present invention are uncoated (neat) individual particles and are not bound to any substance. In particular embodiments, no substances are absorbed or adsorbed onto the surface of the drug nanoparticle. In particular embodiments, the drug nanoparticles are not encapsulated in any substance. In particular embodiments, the drug nanoparticles are not coated with any substance. In particular embodiments, the drug nanoparticles are not microemulsions or nanoemulsions of a drug in particular embodiments.

The particle size of the drug when incorporated in a composition is determined by a particle size analyzer instrument and the measurement is expressed as the mean diameter based on a number distribution. A suitable particle size analyzer instrument is one which employs the analytical technique of light obscuration, also referred to as photozone or single particle optical sensing (SPOS). A suitable light obscuration particle size analyzer instrument is the ACCU-SIZER available from Particle Sizing Systems, Port Richey, Fla.

In various embodiments, the mean particle size of the drug nanoparticles incorporated in a composition does not grow larger than 20% of the initial mean particle size when the composition is stored at room temperature for at least 1 month, or for at least 3 months, or for at least 6 months or for at least 12 months. The term "initial mean particle size", as used herein with regard to the particle size of drug nanoparticles, is the mean particle size of the drug incorporated in the composition when measured by a particle size analyzer instrument within 45 days after the completion of manufacture of the composition (date of manufacture), and the initial mean particle size is from 0.1 microns to 1.5 microns (number) or from 0.01 microns to 1.5 microns (number). In various embodiments, the compositions are anhydrous.

Nanoparticles of a drug can be manufactured using various particle size-reduction methods and equipment known in the art. Such methods include, but are not limited to, wet or dry milling, micronizing, disintegrating, pulverizing, and supercritical carbon dioxide particle size reduction methods. Such supercritical carbon dioxide particle size reduction methods (also known as precipitation with compressed anti-solvents or PCA) and are disclosed in U.S. Pat. Nos. 5,874,029, 5,833,891, 6,113,795, 7,744,923, 8,778,181, US publication US 2014/0296140, and international application PCT/US 16/35993, all of which are herein incorporated by reference.

In the supercritical carbon dioxide particle size reduction methods, a drug is dissolved in a solvent, such as an organic solvent, and is exposed to supercritical carbon dioxide (anti-solvent) to precipitate uncoated drug nanoparticles within a well-characterized particle-size distribution. Sonication is often used in the process to facilitate the precipitation. The carbon dioxide (anti-solvent) and solvent are removed during processing, leaving the uncoated drug nanoparticle powder.

The drug nanoparticles can be in a crystalline form or in an amorphous form or a combination of both. The drug nanoparticles can be water soluble or poorly water soluble drugs.

(i) Poorly Water Soluble Drugs

The compositions of the present invention are especially useful for the delivery of poorly water soluble drugs having solubilities of less than or equal to 10 mg/mL in water at room temperature. Non-limiting examples of poorly water soluble drugs are: anticancer agents such as paclitaxel (taxane), cabazitaxel (taxane), camptothecin, docetaxel (taxane), doxorubicin, daunomycin, cisplatin, 5-fluorouracil, mitomycin, methotrexate, and etoposide; anti-inflammatory agents such as indomethacin, ibuprofen, ketoprofen, flurbiprofen, diclofenac, piroxicam, tenoxicam, naproxen, aspirin, and acetaminophen; antifungal agents such as itraconazole, ketoconazole, miconazole, and amphotericin; hormones such as testosterone, estrogen, progesterone, and estradiol; steroids such as desonide, dexamethasone, hydrocortisone, prednisolone, and triamcinolone; antihypertensive agents such as captopril, ramipril, terazosin, minoxidil, and prazosin; antiemetics such as ondansetron and granisetron; antibiotics such as metronidazole, mupirocin, fusidic acid, cyclosporine, and biphenyl dimethyl dicarboxylic acid.

(ii) Taxane Nanoparticles

The drug nanoparticles of the invention can be taxane nanoparticles, which generally are poorly water soluble drugs. Taxanes are widely used as chemotherapy agents. Taxanes include paclitaxel (I), docetaxel (II), cabazitaxel (III), and other taxane derivatives.

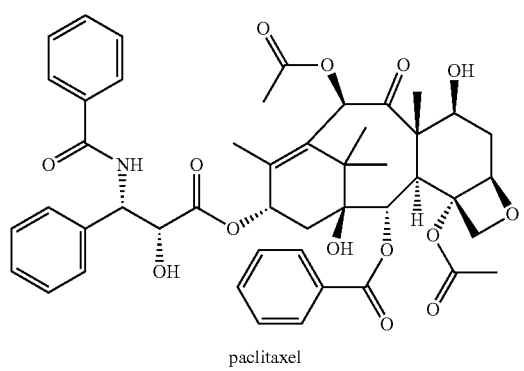

paclitaxel

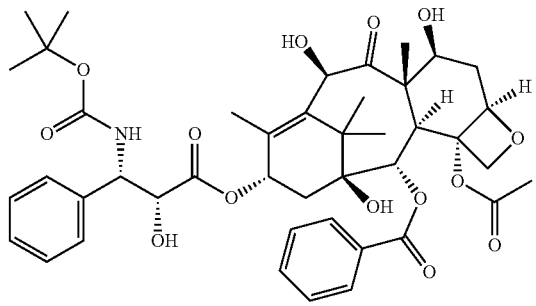

docetaxel

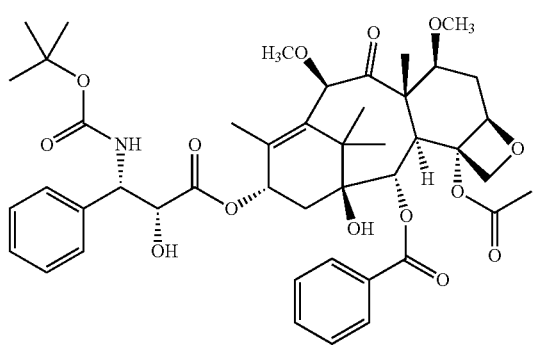

cabazitaxel

The taxane nanoparticles can be paclitaxel nanoparticles, docetaxel nanoparticles, or cabazitaxel nanoparticles, or nanoparticles of other taxane derivatives. Paclitaxel and docetaxel APIs are commercially available from Phyton Biotech LLC, Vancouver, Canada. The docetaxel API and nanoparticles contain not less than 90%, or not less than 95%, or not less than 97.5% docetaxel calculated on the anhydrous, solvent-free basis. The paclitaxel API and nanoparticles contain not less than 90%, or not less than 95%, or not less than 97% paclitaxel calculated on the anhydrous, solvent-free basis. Paclitaxel is also sometimes referred to by the trade name TAXOL. Paclitaxel is a poorly water soluble drug. The solubility of paclitaxel in water is less than 0.05 ppm as determined experimentally by the solubility method described in Example 1. Within the context of the present invention, the taxane or paclitaxel nanoparticles are uncoated (neat) individual particles; the taxane or paclitaxel nanoparticles are not bound to any substance; no substances are absorbed or adsorbed onto the surface of the taxane or paclitaxel nanoparticles; the taxane or paclitaxel nanoparticles are not encapsulated in any substance; the taxane or paclitaxel nanoparticles are not coated with any substance; the taxane or paclitaxel nanoparticles are not microemulsions, nanoemulsions, microspheres, or liposomes of a taxane or paclitaxel; the taxane or paclitaxel particles are not bound to, encapsulated in, or coated with a polymer (or biocompatible polymer), a protein, or albumin; a polymer (or biocompatible polymer), a protein, or albumin is not absorbed or adsorbed onto the surface of the taxane or paclitaxel nanoparticles. In some embodiments, the compositions are free of/do not include or contain a polymer or biocompatible polymer. In some embodiments, the compositions are free of/do not include or contain a protein. In some aspects of the invention, the compositions are free of/do not include or contain albumin.

The taxane nanoparticles, including paclitaxel nanoparticles or docetaxel nanoparticles, can have a mean particle size (number) of from 0.01 microns to 1.5 microns, or from 0.01 microns to less than 1 microns, or from 0.01 microns to 1 micron, or from 0.1 microns to 1.5 microns, or from 0.1 microns to 1.2 microns, or from 0.1 microns to less than 1 micron, or from 0.1 microns to 1 micron, or from 0.2 microns to 1.5 microns, or from 0.2 microns to 1.2 microns, or from 0.2 microns to less than 1 micron, or from 0.2 microns to 1 micron, or from 0.4 microns to 1.5 microns, or from 0.4 microns to 1.2 microns, or from 0.4 microns to less than 1 micron, or from 0.4 microns to 1 micron, or from 0.6 microns to 1.5 microns, or from 0.6 microns to 1.2 microns, or from 0.6 to less than 1 micron, or from 0.6 microns to 1 micron.

In various embodiments, the taxane or paclitaxel nanoparticles are made by a supercritical carbon dioxide particle reduction method (also known as "precipitation with compressed anti-solvents" or "PCA") as disclosed in U.S. Pat. Nos. 5,874,029, 5,833,891, 6,113,795, 7,744,923, 8,778,181, US publication US 2014/0296140, and international patent application PCT/US16/35993 all of which are herein incorporated by reference.

In the supercritical carbon dioxide particle size reduction method, supercritical carbon dioxide (anti-solvent) and solvent, e.g. acetone or ethanol, are employed to generate uncoated taxane nanoparticles within a well-characterized particle-size distribution. The carbon dioxide and acetone are removed during processing (up to 0.5% residual solvent may remain), leaving taxane nanoparticle powder ranging in size from about 200 nm to about 800 nm. Stability studies show that the powder is stable in a vial dose form when stored at controlled room temperature (25° C./60% relative humidity) for up to 59 months and under accelerated conditions (40° C./75% relative humidity) for up to six months.

Taxane nanoparticles produced by various supercritical carbon dioxide particle size reduction methods can have unique physical characteristics as compared to taxane nanoparticles produced by conventional particle size reduction methods using physical impacting or grinding, e.g., wet or dry milling, micronizing, disintegrating, comminuting, microfluidizing, or pulverizing. As disclosed in international patent application PCT/US16/35993 herein incorporated by reference, such unique characteristics include a bulk density (not tapped) between 0.05 g/cm$^3$ and 0.15 g/cm$^3$ and a specific surface area (SSA) of at least 18 m$^2$/g of taxane (paclitaxel and docetaxel) nanoparticles, which are produced by the supercritical carbon dioxide particle size reduction methods described in international patent application PCT/US16/35993 and as described below. This bulk density range is generally lower than the bulk density of taxane particles produced by conventional means, and the SSA is generally higher than the SSA of taxane particles produced by conventional means. These unique characteristics result in significant increases in dissolution rates in water/methanol media as compared to taxanes produced by conventional means. As used herein, the "specific surface area (SSA)" is the total surface area of the taxane nanoparticle per unit of taxane mass as measured by the Brunauer-Emmett-Teller ("BET") isotherm by the following method: a known mass between 200 and 300 mg of the analyte is added to a 30 mL sample tube. The loaded tube is then mounted to a Porous Materials Inc. SORPTOMETER®, model BET-202A. The automated test is then carried out using the BETWIN® software package and the surface area of each sample is subsequently calculated. The bulk density measurement can be conducted by pouring the taxane nanoparticles into a graduated cylinder without tapping at room temperature, measuring the mass and volume, and calculating the bulk density.

As disclosed in international patent application PCT/US16/35993, studies showed a SSA of 15.0 m$^2$/g and a bulk density of 0.31 g/cm$^3$ for paclitaxel nanoparticles produced by milling paclitaxel in a Deco-PBM-V-0.41 ball mill suing a 5 mm ball size, at 600 RPM for 60 minutes at room temperature. Also disclosed in PCT/US16/35993, one lot of paclitaxel nanoparticles had a SSA of 37.7 m$^2$/g and a bulk density of 0.085 g/cm$^3$ when produced by a supercritical carbon dioxide method using the following method: a solution of 65 mg/ml of paclitaxel was prepared in acetone. A BETE MicroWhirl® fog nozzle (BETE Fog Nozzle, Inc.) and a sonic probe (Qsonica, model number Q700) were positioned in the crystallization chamber approximately 8 mm apart. A stainless steel mesh filter with approximately 100 nm holes was attached to the crystallization chamber to collect the precipitated paclitaxel nanoparticles. The supercritical carbon dioxide was placed in the crystallization chamber of the manufacturing equipment and brought to approximately 1200 psi at about 38° C. and a flow rate of 24 kg/hour. The sonic probe was adjusted to 60% of total output power at a frequency of 20 kHz. The acetone solution containing the paclitaxel was pumped through the nozzle at a flow rate of 4.5 mL/minute for approximately 36 hours. Additional lots of paclitaxel nanoparticles produced by the supercritical carbon dioxide method described above had SSA values of: 22.27 m$^2$/g, 23.90 m$^2$/g, 26.19 m$^2$/g, 30.02 m$^2$/g, 21.16 m$^2$/g, 31.70 m$^2$/g, 32.59 m$^2$/g, 33.82 m$^2$/g, 35.90 m$^2$/g, 38.22 m$^2$/g, and 38.52 m$^2$/g.

As disclosed in international patent application PCT/US16/35993, studies showed a SSA of 15.2 m$^2$/g and a bulk density of 0.44 g/cm$^3$ for docetaxel nanoparticles produced by milling docetaxel in a Deco-PBM-V-0.41 ball mill suing a 5 mm ball size, at 600 RPM for 60 minutes at room temperature. Also disclosed in PCT/US16/35993, docetaxel nanoparticles had a SSA of 44.2 m$^2$/g and a bulk density of 0.079 g/cm$^3$ when produced by a supercritical carbon dioxide method using the following method: A solution of 79.32 mg/ml of docetaxel was prepared in ethanol. The nozzle and a sonic probe were positioned in the pressurizable chamber approximately 9 mm apart. A stainless steel mesh filter with approximately 100 nm holes was attached to the pressurizable chamber to collect the precipitated docetaxel nanoparticles. The supercritical carbon dioxide was placed in the pressurizable chamber of the manufacturing equipment and brought to approximately 1200 psi at about 38° C. and a flow rate of 68 slpm. The sonic probe was adjusted to 60% of total output power at a frequency of 20 kHz. The ethanol solution containing the docetaxel was pumped through the nozzle at a flow rate of 2 mL/minute for approximately 95 minutes). The precipitated docetaxel agglomerates and particles were then collected from the supercritical carbon dioxide as the mixture is pumped through the stainless steel mesh filter. The filter containing the nanoparticles of docetaxel was opened and the resulting product was collected from the filter.

As disclosed in international patent application PCT/US16/35993, dissolution studies showed an increased dissolution rate in methanol/water media of paclitaxel and docetaxel nanoparticles made by the supercritical carbon dioxide methods described in international patent application PCT/US16/35993 as compared to paclitaxel and docetaxel nanoparticles made by milling paclitaxel and docetaxel using a Deco-PBM-V-0.41 ball mill suing a 5 mm ball size, at 600 RPM for 60 minutes at room temperature. The procedures used to determine the dissolution rates are as follows. For paclitaxel, approximately 50 mg of material were coated on approximately 1.5 grams of 1 mm glass beads by tumbling the material and beads in a vial for approximately 1 hour. Beads were transferred to a stainless steel mesh container and placed in the dissolution bath containing methanol/water 50/50 (v/v) media at 37° C., pH 7, and a USP Apparatus II (Paddle), operating at 75 rpm. At 10, 20, 30, 60, and 90 minutes, a 5 mL aliquot was removed, filtered through a 0.22 μm filter and analyzed on a UV/VIS spectrophotometer at 227 nm. Absorbance values of the samples were compared to those of standard solutions prepared in dissolution media to determine the amount of material dissolved. For docetaxel, approximately 50 mg of material was placed directly in the dissolution bath containing methanol/water 15/85 (v/v) media at 37° C., pH 7, and a USP Apparatus II (Paddle), operating at 75 rpm. At 5, 15, 30, 60, 120 and 225 minutes, a 5 mL aliquot was removed, filtered through a 0.22 μm filter, and analyzed on a UV/VIS spectrophotometer at 232 nm. Absorbance values of the samples were compared to those of standard solutions prepared in dissolution media to determine the amount of material dissolved. For paclitaxel, the dissolution rate was 47% dissolved in 30 minutes for the nanoparticles made by the supercritical carbon dioxide method versus 32% dissolved in 30 minutes for the nanoparticles made by milling. For docetaxel, the dissolution rate was 27% dissolved in 30 minutes for the nanoparticles made by the supercritical carbon dioxide method versus 9% dissolved in 30 minutes for the nanoparticles made by milling.

In some embodiments, the paclitaxel nanoparticles have an SSA of at least 18, at least 19, at least 20, at least 21, at least 22, at least 23, at least 24, at least 25, at least 26, at least 27, at least 28, at least 29, at least 30, at least 31, at least 32, at least 33, at least 34, or at least 35 $m^2/g$. In other embodiments, the paclitaxel nanoparticles have an SSA of 18 $m^2/g$ to 50 $m^2/g$, or 20 $m^2/g$ to 50 $m^2/g$, or 22 $m^2/g$ to 50 $m^2/g$, or 25 $m^2/$to 50 $m^2/g$, or 30 $m^2/g$ to 50 $m^2/g$, or 18 $m^2/g$ to 45 $m^2/g$, or 20 $m^2/g$ to 45 $m^2/g$, or 22 $m^2/g$ to 45 $m^2/g$, or 25 $m^2/g$ to 45 $m^2/g$, or 30 $m^2/g$ to 45 $m^2/g$, or 18 $m^2/g$ to 40 $m^2/g$, or 20 $m^2/g$ to 40 $m^2/g$, or 22 $m^2/g$ to 40 $m^2/g$, or 25 $m^2/$to 40 $m^2/g$, or 30 $m^2/g$ to 40 $m^2/g$.

In some embodiments, the paclitaxel nanoparticles have a bulk density (not-tapped) of 0.05 $g/cm^3$ to 0.15 $g/cm^3$, or 0.05 $g/cm^3$ to 0.20 $g/cm^3$.

In some embodiments, the paclitaxel nanoparticles have a dissolution rate of at least 40% w/w dissolved in 30 minutes or less in a solution of 50% methanol/50% water (v/v) in a USP II paddle apparatus operating at 75 RPM, at 37° C., and at a pH of 7.

In some embodiments, the docetaxel nanoparticles have an SSA of at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, or at least 42 $m^2/g$. In other embodiments, the docetaxel nanoparticles have an SSA of 18 $m^2/g$ to 60 $m^2/g$, or 22 $m^2/g$ to 60 $m^2/g$, or 25 $m^2/$to 60 $m^2/g$, or 30 $m^2/g$ to 60 $m^2/g$, or 40 $m^2/g$ to 60 $m^2/g$, or 18 $m^2/g$ to 50 $m^2/g$, or 22 $m^2/g$ to 50 $m^2/g$, or 25 $m^2/$to 50 $m^2/g$, or 30 $m^2/g$ to 50 $m^2/g$, or 40 $m^2/g$ to 50 $m^2/g$.

In some embodiments, the docetaxel nanoparticles have a bulk density (not-tapped) of 0.05 $g/cm^3$ to 0.15 $g/cm^3$.

In some embodiments, the docetaxel nanoparticles have a dissolution rate of at least 20% w/w dissolved in 30 minutes or less in a solution of 15% methanol/85% water (v/v) in a USP II paddle apparatus operating at 75 RPM, at 37° C., and at a pH of 7.

It was found that paclitaxel nanoparticle crystals have a tendency to grow in suspensions of water or saline solutions over time forming large needle-like crystals. A crystal growth study was conducted and the results are shown in Table 2 in Example 2 below. It was found that the nanoparticles crystals did not grow in the hydrophobic materials. Also, and surprisingly, the nanoparticle crystals did not grow in aqueous solutions of benzalkonium chloride, CARBOPOL ULTREZ 10, or poloxamer 407.

B. Hydrophobic Carriers

The hydrophobic carriers of the present invention can comprise substances from plant, animal, paraffinic, and/or synthetically derived sources. The hydrophobic carrier is the continuous phase of the compositions. In various embodiments, the hydrophobic carriers are non-polar and/or non-volatile. Non-limiting examples include fats, butters, greases, waxes, solvents, and oils; mineral oils; vegetable oils; petrolatums; water insoluble organic esters and triglycerides; and fluorinated compounds. The hydrophobic carriers can also comprise silicone materials, such as dimethicone.

Plant derived materials include, but are not limited to, arachis (peanut) oil, balsam Peru oil, carnauba wax, candelilla wax, castor oil, hydrogenated castor oil, cocoa butter, coconut oil, corn oil, cotton seed oil, jojoba oil, macadamia seed oil, olive oil, orange oil, orange wax, palm kernel oil, rapeseed oil, safflower oil, sesame seed oil, shea butter, soybean oil, sunflower seed oil, tea tree oil, vegetable oil, and hydrogenated vegetable oil.

Non-limiting examples of animal derived materials include beeswax (yellow wax and white wax), cod liver oil, emu oil, lard, mink oil, shark liver oil, squalane, squalene, and tallow. Non-limiting examples of paraffinic materials include isoparaffin, microcrystalline wax, heavy mineral oil, light mineral oil, ozokerite, petrolatum, white petrolatum, and paraffin wax.

Non-limiting examples of organic esters and triglycerides include C12-15 alkyl benzoate, isopropyl myristate, isopropyl palmitate, medium chain triglycerides, mono- and diglycerides, trilaurin, and trihydroxystearin.

A non-limiting example of a fluorinated compound is perfluoropolyether (PFPE), such as FOMBLIN®HC04 commercially available from Solvay Specialty Polymers.

The hydrophobic carriers of the present invention can comprise pharmaceutical grade hydrophobic substances. In various embodiments of the present invention the hydrophobic carriers comprise petrolatum, mineral oil, or paraffin, or mixtures thereof. In some embodiments, the mineral oil is heavy mineral oil.

In some embodiments, the concentration of the hydrophobic carrier in the compositions is greater than 10% w/w of the total composition weight. In other embodiments, the concentration of the hydrophobic carrier in the compositions is greater than 15%, or greater than 20%, or greater than 25%, or greater than 30%, or greater than 35%, or greater than 40%, or greater than 45%, or greater than 50%, or greater than 55%, or greater than 60%, or greater than 65%, or greater than 70%, or greater than 75%, or greater than 80%, or greater than 82%, or greater than 85%, or greater than 87%, or greater than 90% w/w of the total composition weight. In other embodiments, the concentration of the hydrophobic carrier in the compositions is from greater than 10% w/w to 95% w/w of the total composition weight. In other embodiments, the concentration of the hydrophobic carrier in the compositions is from 11% w/w to 95% w/w, or from 12% w/w to 95% w/w, or from 13% w/w to 95% w/w, or from 14% w/w to 95% w/w, or from 15% w/w to 95% w/w, or from 16% w/w to 95% w/w, or from 17% w/w to 95% w/w, or from 18% w/w to 95% w/w, or from 19% w/w to 95% w/w, or from 20% w/w to 95% w/w of the total composition weight.

(i) Petrolatum

Petrolatum is a purified mixture of semi-solid saturated hydrocarbons obtained from petroleum, and varies from dark amber to light yellow in color. White petrolatum is wholly or nearly decolorized and varies from cream to snow white in color. Petrolatums are available with different melting point, viscosity, and consistency characteristics. Petrolatums may also contain a stabilizer such as an antioxidant. Pharmaceutical grades of petrolatum include Petrolatum USP and White Petrolatum USP.

Various petrolatums are available commercially from the Penreco Corporation under the trade names: ULTIMA, SUPER, SNOW, REGENT, LILY, CREAM, ROYAL, BLOND, and AMBER. Various grades of petrolatum are also available commercially from the Sonneborn Corporation under the trade names: ALBA, SUPER WHITE PROTOPET, SUPER WHITE FONOLINE, WHITE PROTOPET 1S, WHITE PROTOPET 2L, WHITE PROTOPET 3C, WHITE FONOLINE, PERFECTA, YELLOW PROTOPET 2A, YELLOW FONOLINE, PROTOLINE, SONOJELL #4, SONOJELL #9, MINERAL JELLY #10, MINERAL JELLY #14, MINERAL JELLY #17, AND CARNATION TROUGH GREASE. Petrolatums are also available from the Spectrum Chemical Mfg. Corp.

(ii) Mineral oil

Mineral oil is a mixture of liquid hydrocarbons obtained from petroleum. Mineral oil is available in various viscosity grades, such as light mineral oil, heavy mineral oil, and extra heavy mineral oil. Light mineral oil has a kinematic viscosity of not more than 33.5 centistokes at 40° C. Heavy mineral oil has a kinematic viscosity of not less than 34.5 centistokes at 40° C. Mineral oil may contain a suitable stabilizer. Pharmaceutical grades of mineral oil include Mineral Oil USP, which is heavy mineral oil, and Light Mineral Oil NF, which is light mineral oil. Mineral oil is commercially available from the Penreco Corporation under the DRAKEOL trade name, and the Sonneborn Corporation under the trade names BENOL, BLANDOL, BRITOL, CARNATION, ERVOL, GLORIA, KAYDOL, KLEAROL, PROTOL, and RUDOL. Mineral oil is also commercially available from the Spectrum Chemical Mfg. Corp.

(iii) Paraffin Wax

Paraffin wax is a purified mixture of solid hydrocarbons obtained from petroleum. It may also be synthetically derived by the Fischer-Tropsch process from carbon monoxide and hydrogen which are catalytically converted to a mixture of paraffin hydrocarbons. Paraffin wax may contain an antioxidant. Pharmaceutical grades of paraffin wax include Paraffin NF and Synthetic Paraffin NF. Paraffin waxes are commercially available from the Spectrum Chemical Mfg. Corp, Koster Keunen, Inc. and Frank B. Ross, Inc.

C. Volatile Silicone Fluids

Volatile silicone fluids, also known as volatile silicone oils, are volatile liquid polysiloxanes which can by cyclic or linear. They are liquid at room temperature. Linear volatile silicone fluids include polydimethylsiloxane, hexamethyldisiloxane and octamethyltrisiloxane and are commercially available from Dow Corning under the trade names DOW CORNING Q7-9180 Silicone Fluid 0.65 cSt and DOW CORNING Q7-9180 Silicone Fluid 1.0 cSt, respectively. Cyclic volatile silicone fluids are generally known as cyclomethicones.

(i) Cyclomethicone

Cyclomethicone is a fully methylated cyclic siloxane containing repeating units of formula (IV):

$$[-(CH_3)_2SiO-]_n \qquad (IV)$$

in which n is 3, 4, 5, 6, or 7; or mixtures thereof. Cyclomethicone is a clear, colorless volatile liquid silicone fluid. Cyclomethicone has emollient properties and helps to improve the tactile feel of an oil based product by making it feel less greasy on the skin. Pharmaceutical grade cyclomethicone includes Cyclomethicone NF. Cyclomethicone NF is represented by formula (IV) in which n is 4 (cyclotetrasiloxane), 5 (cyclopentasiloxane), or 6 (cyclohexasiloxane); or mixtures thereof. Cyclopentasiloxane, also known as decamethylcylcopentasiloxane, cyclomethicone D5, or cyclomethicone 5, is the cyclomethicone represented by formula (IV) in which n is 5 (pentamer), but it can contain small amounts (generally less than 1%) of one or more of the other cyclic chain length cyclomethicones. Cyclopentasiloxane is available in a pharmaceutical grade as Cyclomethicone NF. Cyclomethicones are commercially available from Dow Corning under the trade names DOW CORNING ST-Cyclomethicone 5-NF, DOW CORNING ST-Cyclomethicone 56-NF, and XIAMETER PMX-0245. It is also commercially available from the Spectrum Chemical Mfg. Corp. Cyclopentasiloxane has a vapor pressure of about 20 to about 27 Pa at 25° C.

In one embodiment, the concentration of cyclomethicone in the composition is less than 25% w/w. In another embodiment, the cyclomethicone in the composition is at a concentration from 5 to 24% w/w. In another embodiment, the concentration of cyclomethicone is from 5 to 20% w/w. In another embodiment, the cyclomethicone is at a concentration of from 5 to 18% w/w. In another embodiment, the concentration of cyclomethicone is 13% w/w. In various embodiment, the concentration of cyclomethicone can be 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, or 24% w/w or any percentage derivable therein of the total composition weight. In one embodiment, the cyclomethicone is cyclopentasiloxane.

D. Aqueous Based Compositions

Aqueous based compositions of the invention comprise poorly water soluble drug nanoparticles and an aqueous carrier. The aqueous formulations are dispersions of the drug nanoparticles in an aqueous carrier. The drug nanoparticles can be completely dispersed, partially dispersed and partially dissolved, but not completely dissolved in the aqueous carrier.

It was observed that poorly water soluble drug nanoparticle crystals, such as paclitaxel nanoparticles, rapidly grew in water and in aqueous based carriers. In many cases, the growth was observed in as little as 3 days at room temperature, and some cases in 24 hours. Many of the crystals were needle-like in shape and were larger than 5 μm in length. A study was conducted and the results are shown in Table 2 in Example 2. Surprisingly, the drug nanoparticle crystal growth was inhibited by the addition of poloxamer 407, a quaternary ammonium compound, or a cross-linked acrylic acid polymer to the aqueous based carrier during processing. The addition of poloxamer 188 did not inhibit the growth of the nanoparticle crystals.

It was also observed that the presence of a quaternary ammonium compound, or a cross-linked acrylic acid polymer, or mixtures thereof in an aqueous carrier comprising drug nanoparticle crystals prevented growth of the nanoparticle crystals over time. A study was conducted and the results are shown in Table 11 in Example 8 revealing that the mean particle size of poorly water soluble drug nanoparticles (paclitaxel) in an aqueous composition comprising poloxamer 407, a quaternary ammonium compound, or a cross-linked acrylic acid polymer, or mixtures thereof does not grow larger than 20% of the initial mean particle size when the aqueous composition is stored at room temperature for 6 months. In some embodiments, there is disclosed an aqueous based composition comprising an aqueous carrier; a plurality of poorly water soluble drug nanoparticles; and a quaternary ammonium compound, or a cross-linked acrylic acid polymer, or mixtures thereof; wherein the mean particle size of the drug nanoparticles is from 0.1 microns to 1.5 microns (number) or from 0.01 microns to 1.5 microns (number), and wherein the mean particle size of the drug nanoparticles does not grow larger than 20% of the initial mean particle size when the composition is stored at room temperature for at least 6 months. In other embodiments, the composition further comprises poloxamer 407.

In one aspect of the invention, disclosed are compositions comprising drug nanoparticles, an aqueous carrier, and poloxamer 407, a quaternary ammonium compound, or a cross-linked acrylic acid polymer, or mixtures thereof. It was surprisingly found that the addition of poloxamer 407, a quaternary ammonium compound, or a cross-linked acrylic acid polymer inhibited the crystal growth of the drug nanoparticles in aqueous carriers. The aqueous based compositions of the invention are suitable for topical, injectable, (IV) infusion, or oral liquid dosage forms. In one embodiment, the additive to inhibit crystal growth is poloxamer 407. In various embodiments, the quaternary ammonium compound is the additive to inhibit crystal growth and is benzalkonium chloride or benzethonium chloride. In other embodiments, the quaternary ammonium compound is benzalkonium chloride. In other embodiments, the cross-linked acrylic acid polymer is the additive to inhibit crystal growth and is Carbomer.

In one aspect of the invention, the composition comprises poloxamer 407 and drug nanoparticles in an aqueous carrier suitable for injection delivery including (IV) infusion. In some embodiments the drug nanoparticles are taxane nanoparticles. In various embodiments, the taxane nanoparticles are docetaxel nanoparticles, paclitaxel nanoparticles, or cabazitaxel nanoparticles.

In another aspect of the invention, the composition comprises a quaternary ammonium compound and drug nanoparticles in an aqueous carrier suitable for injection delivery including (IV) infusion. In some embodiments the drug nanoparticles are taxane nanoparticles. In various embodiments, the taxane nanoparticles are docetaxel nanoparticles, paclitaxel nanoparticles, or cabazitaxel nanoparticles. In other embodiments, the quaternary ammonium compounds are benzalkonium chloride or benzethonium chloride.

In one aspect of the invention, disclosed are methods of inhibiting the growth of a dispersion of poorly water soluble crystalline drug nanoparticles in an aqueous based carrier, the method comprising adding poloxamer 407, a quaternary ammonium compound, or a cross-linked acrylic acid polymer, or mixtures thereof, to the aqueous based carrier during processing, wherein the mean particle size of the drug nanoparticles is from 0.1 microns to 1.5 microns (number) or from 0.01 microns to 1.5 microns (number). In some embodiments, the quaternary ammonium compound is benzalkonium chloride or benzethonium chloride. In some embodiments, the cross-linked acrylic acid polymer is carbomer. In some embodiments, the drug nanoparticles are taxane nanoparticles. In other embodiments, the taxane nanoparticles are paclitaxel nanoparticles, docetaxel nanoparticles, or cabazitaxel nanoparticles. In still other embodiments, the taxane nanoparticle are paclitaxel nanoparticles.

(i) Poloxamer 407

Poloxamer 407 is a solid, hydrophilic, nonionic, synthetic block copolymer of ethylene oxide and propylene oxide conforming to the general formula (V)

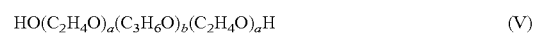

$$HO(C_2H_4O)_a(C_3H_6O)_b(C_2H_4O)_aH \qquad (V)$$

where a is 101 and b is 56. Poloxamer 407 has an average molecular weight of 9840-14600. The term "poloxamer" is the nonproprietary name of the copolymer. Poloxamers are available in several types which have various physical forms and various average molecular weights. Each specific poloxamer type is identified by the nonproprietary name "poloxamer" followed by a three digit number, the first two digits of which when multiplied by 100 correspond to the approximate average molecular weight of the polyoxypropylene portion of the copolymer; and the third digit, when multiplied by 10, corresponds to the percentage by weight of the polyoxyethylene portion. Poloxamers are available in pharmaceutical, cosmetic, and industrial grades. Pharmaceutical grade poloxamers are listed in recognized pharmaceutical compendia such as USP/NF and European Pharmacopeia (PhEur). According to the USP/NF and PhEur, a suitable antioxidant may be added. Poloxamer 407 is commercially available from BASF under the trade name PLURONIC® F127. The addition of poloxamer 188 to an aqueous carrier did not inhibit crystal growth of the drug nanoparticles. Suitable concentrations of Poloxamer 407 are at least 2% w/w, or from 0.1 to 25% w/w, or from 0.1 to 20% w/w, or from 0.1 to 15% w/w, or from 0.1 to 10% w/w, or from 1 to 10% w/w, or from 2 to 10% w/w, or from 2 to 15%% w/w, or from 2 to 20% w/w, or from 2 to 25% w/w.

(ii) Quaternary Ammonium Compounds

Quaternary ammonium compounds (including salts) are positively charged tetra-substituted nitrogen derivatives of formula (VI)

(VI)

In which $R^1$, $R^2$, $R^3$, and $R^4$ may be the same or different, but may not be hydrogen. $X^-$ represents a typical anion such as chloride. Suitable quaternary ammonium compounds include benzalkonium chloride and benzethonium chloride. Benzalkonium chloride is commercially available in a 100% powder or a 50% aqueous solution. Other examples of quaternary ammonium compounds are disclosed in the International Cosmetic Ingredient Dictionary and Handbook, 12h edition, 2008 herein incorporated by reference. Suitable concentrations of quaternary ammonium compounds are at least 0.05% w/w, or at least 0.1% w/w, or at least 1% w/w, or at least 2% w/w, or from 0.05 to 5% w/w, or from 0.1 to 5% w/w, or from 1 to 5% w/w, or from 2 to 5% w/w.

(iii) Cross-Linked Acrylic Acid Polymers

Cross-linked acrylic acid polymers are high molecular weight homo- and co-polymers of acrylic acid cross-linked with a polyalkenyl polyether. Suitable cross-linked acrylic acid polymers include Carbomer (INCI name), Acrylates Copolymer (INCI name), Acrylates/C10-30 Alkyl Acrylate Crosspolymer (INCI name), Acrylates Crosspolymer-4 (INCI name), and Polyacrylate-1 Crosspolymer (INCI name). The above mentioned polymers are all commercially available from the Lubrizol Corporation under the CARBOPOL® trade name. Examples of Carbomer available from the Lubrizol Corporation include CARBOPOL 934, CARBOPOL 934P, CARBOPOL 940, CARBOPOL 980, CARBOPOL 941, CARBOPOL 981, CARBOPOL 2984, CARBOPOL 5984, CARBOPOL SILK 100, CARBOPOL ETD 2050, ULTREZ 10, and ULTREZ 30. Examples of Acrylates Copolymer available from the Lubrizol Corporation include CARBOPOL AQUA SF-1, and CARBOPOL AQUA SF-1 OS. Examples of Acrylates/C10-30 Alkyl Acrylate Crosspolymer available from the Lubrizol Corporation include CARBOPOL ULTREZ 20, CARBOPOL ULTREZ 21, CARBOPOL ETD 2020, CARBOPOL 1342, CARBOPOL1382, and CARBOPOL SC-200. An example of Acrylates Crosspolymer-4 is CARBOPOL AQUA SF-2. An example of Polyacrylate-1 Crosspolymer is CARBOPOL AQUA CC. Suitable concentrations of cross-linked acrylic acid polymers are at least 0.1% w/w, or 0.5% w/w, or from 0.1 to 5% w/w, or from 0.5 to 5% w/w.

E. Additional Ingredients and Adjuvants

The compositions of the invention can further comprise functional ingredients suitable for use in pharmaceutical compositions. Non-limiting examples include absorbents, acidifying agents, antimicrobial agents, antioxidants, binders, biocides, buffering agents, bulking agents, crystal growth inhibitors, chelating agents, colorants, deodorant agents, emulsion stabilizers, film formers, fragrances, humectants, lytic agents, enzymatic agents, opacifying agents, oxidizing agents, pH adjusters, plasticizers, preservatives, reducing agents, emollient skin conditioning agents, humectant skin conditioning agents, moisturizers, surfactants, emulsifying agents, cleansing agents, foaming agents, hydrotopes, solvents, suspending agents, viscosity control agents (rheology modifiers), viscosity increasing agents (thickeners), and propellants. Listings and monographs of the examples of the functional ingredients described herein are disclosed in The International Cosmetic Ingredient Dictionary and Handbook (INCI), $12^{th}$ Edition, 2008, herein incorporated by reference.

The compositions of the invention can further comprise additional pharmaceutically active ingredients, cosmetically active ingredients, and veterinary agents suitable for topical use.

Although, the hydrophobic compositions of the present invention can further comprise additional penetration enhancers, it was found that it was not necessary to include additional penetration enhancers to increase the skin penetration (i.e., into the epidermal and dermal portions of skin) of the drug nanoparticles in hydrophobic compositions comprising a hydrophobic carrier and one or more volatile silicone fluids. In fact, the additions of skin penetration enhancers had little or no effect on the skin penetration of the hydrophobic compositions.

The term "penetration enhancer" has been used to describe compounds or materials or substances that facilitate drug absorption through the skin. These compounds or materials or substances can have a direct effect on the permeability of the skin, or they can augment percutaneous absorption by increasing the thermodynamic activity of the penetrant, thereby increasing the effective escaping tendency and concentration gradient of the diffusing species. The predominant effect of these enhancers is to either increase the stratum corneum's degree of hydration or disrupt its lipoprotein matrix, the net result in either case being a decrease in resistance to drug (penetrant) diffusion (Remington, The Science and Practice of Pharmacy, $22^{nd}$ ed.).

Non-limiting examples of skin penetration enhancers include oleyl alcohol, isopropyl myristate, and Diethylene Glycol Monoethyl Ether (DGME) which is available under the trade name TRANSCUTOL P. Other examples of skin penetration enhancers can be found in "Skin Penetration Enhancers Cited in the Technical Literature", Osborne, David W., and Henke, Jill J., Pharmaceutical Technology, November 1997, herein incorporated by reference. Such examples include: Fatty alcohols such as aliphatic alcohols, Decanol, Lauryl alcohol (dodecanol), Linolenyl alcohol, Nerolidol, 1-Nonanol, n-Octanol, Oleyl alcohol, Fatty acid esters, Butylacetate, Cetyl lactate, Decyl N,N-dimethylamino acetate, Decyl N,N-dimethylamino isopropionate, Diethyleneglycol oleate, Diethyl sebacate, Diethyl succinate, Diisopropyl sebacate, Dodecyl N,N-dimethylamino acetate, Dodecyl (N,N-dimethylamino)-butyrate, Dodecyl N,N-dimethylamino isopropionate, Dodecyl 2-(dimethylamino) propionate, EO-5-oleyl ester, Ethyl acetate, Ethylaceto acetate, Ethyl propionate, Glycerol monoethers, Glycerol monolaurate, Glycerol monooleate, Glycerol monolinoleate, Isopropyl isostearate, Isopropyl linoleate, Isopropyl myristate, Isopropyl myristate/fatty acid monoglyceride combination, Isopropyl myristate/ethanol/L-lactic acid (87:10:3) combination, Isopropyl palmitate, Methyl acetate, Methyl caprate, Methyl laurate, Methyl propionate, Methyl valerate, 1-Monocaproyl glycerol, Monoglycerides (medium chain length), Nicotinic esters (benzyl), Octyl acetate, Octyl N,N-dimethylamino acetate, Oleyl oleate, n-Pentyl N-acetylprolinate, Propylene glycol monolaurate, Sorbitan dilaurate, Sorbitan dioleate, Sorbitan monolaurate, Sorbitan monooleates, Sorbitan trilaurate, Sorbitan trioleate, Sucrose coconut fatty ester mixtures, Sucrose monolaurate, Sucrose monooleate, and Tetradecyl N,N-dimethylamino acetate; Fatty acids such as Alkanoic acids, Capric acid, Diacid, Ethyloctadecanoic acid, Hexanoic acid, Lactic acid, Lauric acid, Linoelaidic acid, Linoleic acid, Linolenic acid, Neodecanoic acid, Oleic acid, Palmitic acid, Pelargonic acid, Propionic acid, and Vaccenic acid; Fatty alcohol ethers such as α-Monoglyceryl ether, EO-2-oleyl ether, EO-5-oleyl ether, EO-10-oleyl ether, and Ether derivatives of polyglycerols and alcohols (1-O-dodecyl-3-O-methyl-2-0-(2', 3'-dihydroxypropyl) glycerol); Biologics such as L-α-aminoacids, Lecithin, Phospholipids, Saponin/phospholipids, Sodium deoxycholate, Sodium taurocholate, and Sodium tauroglycocholate; Enzymes such as Acid phosphatase, Calonase, Orgelase, Papain, Phospholipase A-2, Phospholipase C, and Triacylglycerol hydrolase; Amines and Amides such as Acetamide derivatives, Acyclic amides, N-Adamantyl n-alkanamides, Clofibric acid amides, N,N-Didodecyl acetamide, Di-2-ethylhexylamine, Diethyl methyl benzamide, N,N-Diethyl-m-toluamide, N,N-Dimethyl-m-toluamide, Ethomeen S12 [bis-(2-hydroxyethyl) oleylamine], Hexamethylene lauramide, Lauryl-amine (dodecylamine), Octyl amide, Oleylamine, Unsaturated cyclic ureas, and Urea; Complexing Agents such as, β- and γ-cyclodextrin complexes, Hydroxypropyl methylcellulose, Liposomes, Naphthalene diamide diimide, and Naphthalene diester diimide; Macrocyclics such as Macrocyclic lactones, ketones, and anhydrides (optimum ring-16), and Unsaturated cyclic ureas; Classical surfactants such as Brij 30, Brij 36T, Brij 35, Brij 52, Brij 56, Brij 58, Brij 72, Brij 76, Brij 78, Brij 92, Brij 96, Brij 98, Cetyl trimethyl ammonium bromide, Empicol ML26/F, HCO-60 surfactant, Hydroxypolyethoxydodecane, Ionic surfactants (ROONa, $ROSO_3Na$, $RNH_3Cl$, R=8-16), Lauroyl sarcosine, Nonionic surface active agents, Nonoxynol, Octoxynol, Phenylsulfonate CA, Pluronic F68, Pluronic F 127, Pluronic L62, Polyoleates (nonionic surfactants), Rewopal HV 10, Sodium laurate, Sodium Lauryl sulfate (sodium dodecyl sulfate), Sodium oleate, Sorbitan dilaurate, Sorbitan dioleate, Sorbitan monolaurate, Sorbitan monooleates, Sorbitan trilaurate, Sorbitan trioleate, Span 20, Span 40, Span 85, Synperonic NP, Triton X-100, Tween 20, Tween 40, Tween 60, Tween 80, and Tween 85; N-methyl pyrrolidone and related compounds such as N-Cyclohexyl-2-pyrrolidone, 1-Butyl-3-dodecyl-2-pyrrolidone, 1,3-Dimethyl-2-imidazolikinone, 1,5 Dimethyl-2-pyrrolidone, 4,4-Dimethyl-2-undecyl-2-oxazoline, 1-Ethyl-2-pyrrolidone, 1-Hexyl-4-methyloxycarbonyl-2-pyrrolidone, 1-Hexyl-2-pyrrolidone, 1-(2-Hydroxyethyl) pyrrolidinone, 3-Hydroxy-N-methyl-2-pyrrolidinone, 1-isopropyl-2-undecyl-2-imidazoline, 1-Lauryl-4-melhyloxycarbonyl-2-pyrrolidone, N-Methyl-2-pyrrolidone, Poly(N-vinylpyrrolidone), Pyroglutamic acid esters, and 2-Pyrrolidone (2-pyrrolidinone); Ionic compounds such as Ascorbate, Amphoteric cations and anions, Calcium thioglycolate, Cetyl trimethyl ammonium bromide, 3,5-Diiodosalicylate sodium, Lauroylcholine iodide, 5-Methoxysalicylate sodium, Monoalkyl phosphates, 2-PAM chloride, 4-PAM chloride (derivatives of N-methyl picolinium chloride), Sodium carboxylate, and Sodium hyaluronate; Dimethyl sulfoxide and related compounds such as Cyclic sulfoxides, Decylmethyl sulfoxide, Dimethyl sulfoxide (DMSO), and 2-Hydroxyundecyl methyl sulfoxide; Solvents and related compounds such as Acetone, n-Alkanes (chain length between 7 and 16), Cyclohexyl-1,1-dimethylethanol, Dimethylacetamide, Dimethyl formamide, Ethanol, Ethanol/d-limonene combination, 2-Ethyl-1,3-hexanediol, Ethoxydiglycol (TRANSCUTOL), Glycerol, Glycols, Lauryl chloride, Limonene, N-Methylformamide, 2-Phenylethanol, 3-Phenyl-1-propanol, 3-Phenyl-2-propen-1-ol, Polyethylene glycol, Polyoxyethylene sorbitan monoesters, Polypropylene glycol, Primary alcohols (tridecanol), Propylene glycol, Squalene, Triacetin, Trichloroethanol, Trifluoroethanol, Trimethylene glycol, and Xylene; Azone and related compounds such as N-Acylhexahydro-2-oxo-1H-azepines, N-Alkyl-dihydro-1,4-oxazepine-5,7-diones, N-Alkylmorpholine-2,3-diones, N-Alkylmorpholine-3,5-diones, Azacycloalkane derivatives (-ketone, -thione), Azacycloalkenone derivatives, 1-[2-(Decylthio)ethyl]azacyclopentan-2-one (HPE-101), N-(2,2-Dihydroxyethyl)dodecylamine, 1-Dodecanoylhexahydro-1-H-azepine, 1-Dodecyl azacycloheptan-2-one (azone or laurocapram), N-Dodecyl diethanolamine, N-Dodecyl-hexahydro-2-thio-1H-azepine, N-Dodecyl-N-(2-methoxyethyl)acetamide, N-Dodecyl-N-(2-methoxyethyl) isobutyramide, N-Dodecyl-piperidine-2-thione, N-Dodecyl-2-piperidinone, N-Dodecyl pyrrolidine-3,5-dione, N-Dodecyl pyrrolidine-2-thione, N-Dodecyl-2-pyrrolidone, 1-Famesylazacycloheptan-2-one, 1-F amesylazacyclopentan-2-one, 1-Geranylazacycloheptan-2-one, 1-Geranylazacyclopentan-2-one, Hexahydro-2-oxo-azepine-1-acetic acid esters, N-(2-Hydroxyethyl)-2-pyrrolidone, 1-Laurylazacycloheptane, 2-(1-Nonyl)-1,3-dioxolane, 1-N-Octylazacyclopentan-2-one, N-(1-Oxododecyl)-hexahydro-1H-azepine, N-(1-Oxododecyl)-morpholines, 1-Oxohydrocarbyl-substituted azacyclohexanes, N-(1-Oxotetradecyl)-hexahydro-2-oxo-1H-azepine, and N-(1-Thiododecyl)-morpholines; and others such as Aliphatic thiols, Alkyl N,N-dialkyl-substituted amino acetates, Anise oil, Anticholinergic agent pretreatment, Ascaridole, Biphasic group derivatives, Bisabolol, Cardamom oil, 1-Carvone, Chenopodium (70% ascaridole), Chenopodium oil, 1,8 Cineole (eucalyptol), Cod liver oil (fatty acid extract), 4-Decyloxazolidin-2-one, Dicyclohexylmethylamine oxide, Diethyl hexadecylphosphonate, Diethyl hexadecylphosphoramidate, N,N-Dimethyl dodecylamine-N-oxide, 4, 4-Dimelhyl-2-undecyl-2-oxazoline, N-Dodecanoyl-L-amino acid methyl esters, 1,3-Dioxacycloalkanes (SEPAs), Dithiothreitol, Eucalyptol (cineole), Eucalyptus oil, Eugenol, Herbal extracts, Lactam N-acetic acid esters, N-Hydroxyethalaceamide, 2-Hydroxy-3-oleoyloxy-1-pyroglutamyloxypropane, Menthol, Menthone, Morpholine derivatives, N-Oxide, Nerolidol, Octyl-β-D-(thio) glucopyranosides, Oxazolidinones, Piperazine derivatives, Polar lipids, Polydimelhylsiloxanes, Poly [2-(methylsulfinyl)ethyl acrylate], Polyrotaxanes, Polyvinylbenzyldimethylalkylammonium chloride, Poly(N-vinyl-N-methyl acetamide), Sodium pyroglutaminate, Terpenes and azacyclo ring compounds, Vitamin E (α-tocopherol), and Ylang-ylang oil. Additional examples of penetration enhancers not listed above can be found in "Handbook of Pharmaceutical Excipients", Fifth edition, and include glycofurol, lanolin, light mineral oil, myristic acid, polyoxyethylene alky ethers, and thymol.

Although the hydrophobic compositions of the invention can further comprise alcohols, it is not necessary for the compositions to contain alcohols, or $C_1$-$C_5$ aliphatic alcohols. In some aspects of the invention, the compositions are free of/do not include or contain $C_1$-$C_5$ aliphatic alcohols.

Although the hydrophobic compositions of the invention can further comprise additional volatile solvents, it is not necessary for the hydrophobic compositions to contain additional volatile solvents. Volatile solvents are also known as "fugitive" solvents. Non-limiting examples of volatile solvents include volatile alcohols, such as volatile $C_1$ to $C_4$ aliphatic alcohols; and volatile $C_1$ to $C_4$ aliphatic ketones, such as acetone. In some aspects of the inventions, the compositions are free of/do not include or contain volatile $C_1$ to $C_4$ aliphatic ketones.

Although the hydrophobic compositions of the invention can further comprise surfactants, it is not necessary for the hydrophobic compositions to contain surfactants. The term "surfactant" or "surface active agent" means a compound or material or substance that exhibits the ability to lower the surface tension of water or to reduce the interfacial tension between two immiscible substances and includes anionic, cationic, nonionic, amphoteric, and/or phospholipid surfactants. Non-limiting examples of surfactants can be found in McCutcheon's Emulsifiers & Detergents, 2001 North American Edition herein incorporated by reference and also in the International Cosmetic Ingredient Dictionary and Handbook (INCI), 12th Edition, 2008, herein incorporated by reference. Such examples include, but are not limited to, the following: block polymers, e.g., Poloxamer 124; ethoxylated alcohols e.g., Ceteth-2, Ceteareth-20, Laureth-3; ethoxylated fatty esters and oils, e.g., PEG-40 Hydrogenated Castor Oil, PEG-36 Castor Oil, PEG-150 Distearate; glycerol esters, e.g., Polyglyceryl-3 Diisostearate, Glyceryl Stearate; glycol esters, PEG-12 Dioleate, LEXEMUL P; phosphate esters, e.g., Cetyl Phosphate; polymeric surfactants, e.g., PVM/MA Copolymer, PVM/MA Copolymer, Acrylates/C10-30 Alkyl Acrylate Crosspolymer; quaternary surfactants, e.g., Cetrimonium Chloride; Silicone Based Surfactants, e.g., PEG/PPG-20/6 Dimethicone; Sorbitan Derivatives, e.g., Sorbitan Stearate, Polysorbate 80; sucrose and glucose esters and derivatives, e.g., PEG-20 Methyl Glucose Sesquistearate; and sulfates of alcohols, e.g., Sodium Lauryl Sulfate. More generally, surfactants can be classified by their ionic type such as anionic, cationic, nonionic, or amphoteric. They can also be classified by their chemical structures, such as block polymers, ethoxylated alcohols, ethoxylated fatty esters and oils, glycerol esters, glycol esters, phosphate esters, polymeric surfactants, quaternary surfactants, silicone-based surfactants, sorbitan derivatives, sucrose and glucose esters and derivatives, and sulfates of alcohols.

F. Manufacture

The compositions of the invention may be manufactured by methods and equipment known in the art for manufacture of pharmaceutical products including topical, injectable, and oral liquid products. Such methods include, but are not limited to the use of mechanical mixers, dissolvers, dispersers, homogenizers, and mills. Non-limiting examples include LIGHTNIN propeller mixers, COWLES dissolvers, IKA ULTRA TURRAX dispersers, SILVERSON homogenizers, LEE counter-rotating side-scrapping mixers, in-line and in-tank rotor-stator homogenizers, 3-roll mills, ointment mills, and rotor-stator mills. "All-in-one" vacuum mixing systems that have a rotating side-scrapping mixer plus an in-tank homogenizer may also be used. Such mixers include, but are not limited to OLSA mixers, FRYMA-KORUMA mixers, and LEE TRI-MIX TURBO-SHEAR kettles. The compositions of the invention can be manufactured from small laboratory scale batches using laboratory mixing equipment to full-scale production batches.

II. Enhanced Topical Delivery Methods

In one aspect of the invention, there is disclosed a method for enhancing penetration of drug nanoparticles into the skin, the method comprising applying to the surface of the skin a hydrophobic composition which comprises a continuous hydrophobic carrier, one or more volatile silicone fluids, and a plurality of drug nanoparticles. In various embodiments, the hydrophobic carriers are non-polar and/or non-volatile. In some embodiments, the hydrophobic carriers comprise a hydrocarbon. In other embodiments, the hydrophobic carriers comprise petrolatum, mineral oil, and paraffin. In some embodiments, the mineral oil is heavy mineral oil. In some embodiments, the concentration of the volatile silicone fluid in the composition formulation is at an amount effective to enhance skin penetration of the drug nanoparticles as compared to the formulation without the volatile silicone fluid as determined by an in vitro Franz diffusion cell (FDC) system using human cadaver skin. A suitable in vitro Franz diffusion cell system is described in Example 9 below. In some embodiments, the one or more volatile silicone fluid is at a concentration from 5 to 24% w/w. In other embodiments, the concentration of the one or more volatile silicone fluid is from 5 to 20% w/w. In other embodiments, the one or more volatile silicone fluid is at a concentration of from 5 to 18% w/w. In still other embodiments, the concentration of the one or more volatile silicone fluid is 13% w/w. In various embodiments, the concentration of the one or more volatile silicone fluid can be 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, or 24% w/w or any percentage derivable therein of the total composition weight. In various embodiments, the one or more volatile silicone fluid is cyclomethicone. In other embodiments, the cyclomethicone is cyclopentasiloxane. In some embodiments, the hydrophobic compositions do not contain additional penetration enhancers. In other embodiments, the hydrophobic compositions do not contain additional volatile solvents. In still other embodiments, the hydrophobic compositions do not contain a surfactant. In other embodiments, the hydrophobic compositions are free of/do not include or contain alcohols or $C_1$ to $C_5$ aliphatic alcohols. In some embodiments, the drug is a poorly water soluble drug. In various embodiment, the drug is a taxane and can be paclitaxel, docetaxel, or cabazitaxel. In some embodiments, the skin is diseased skin. In other embodiments, the diseased skin is psoriatic skin. In some embodiments, the hydrophobic compositions are anhydrous. In other embodiments, the hydrophobic compositions are sterile. In other embodiments, the hydrophobic compositions are non-sterile. In other embodiments, the hydrophobic compositions have a low bioburden. In some embodiments, the hydrophobic compositions are semi-solid compositions. In still other embodiments, the hydrophobic compositions are ointments. In some embodiments, the hydrophobic compositions are semi-solid compositions, including ointments, and have a viscosity of from 12,500 cps to 247,500 cps, or from 25,000 cps to 150,000 cps as measured at room temperature by a Brookfield RV viscometer using a small sample adapter with a $SC_4$-14 spindle and a 6R chamber at 5 rpm with an equilibration time of 2 minutes. An alternative method for performing viscosity measurements of the hydrophobic, semi-solid compositions is using a Brookfield RV viscometer on a helipath stand with the helipath on, with a T-E spindle at 10 RPM at room temperature for 45 seconds. In some embodiments, the hydrophobic compositions are semi-solid compositions, including ointments, and have a viscosity of from 25,000 cps to 500,000 cps, or from 25,00 cps to 400,000 cps, or from 25,000 cps to 350,000 cps, or from 25,000 cps to 300,000 cps, or from 50,000 cps to 500,000 cps, or from 50,000 cps to 400,000 cps, or from 50,000 cps to 350,000 cps, or from 50,000 cps to 300,000 cps, or from 75,000 cps to 500,000 cps, or from 75,000 cps to 400,000 cps, or from 75,000 cps to 350,000 cps, or from 75,000 cps to 300,000 cps, or from 100,000 cps to 500,000 cps, or from 100,000 cps to 400,000 cps, or from 100,000 cps to 350,000 cps, or from 100,000 cps to 300,000 cps using a Brookfield RV viscometer on a helipath stand with the helipath on, with a T-E spindle at 10 RPM at room temperature for 45 seconds.

In some embodiments, the hydrophobic compositions are not sprays and are not sprayable. In other embodiments, the drug nanoparticles do not penetrate through human cadaver skin or less than 0.01 $\mu g/cm^2$ penetrate (a negligible amount) through human cadaver skin when the composition is applied to the human cadaver skin as determined by an in vitro Franz diffusion cell system. A suitable in vitro Franz diffusion cell system is described in Example 9 below.

In another aspect of the invention, there is disclosed a method for enhancing penetration of taxane nanoparticles into the skin, the method comprising applying to the surface of the skin a hydrophobic composition which comprises a continuous hydrophobic carrier, one or more volatile silicone fluids, and the taxane nanoparticles. In various embodiments, the hydrophobic carriers are non-polar and/or non-volatile. In various embodiments, the taxane nanoparticles are paclitaxel nanoparticles, docetaxel nanoparticles, or cabazitaxel nanoparticles. In some embodiments, the taxane nanoparticles are paclitaxel nanoparticles. In other embodiments, the hydrophobic carriers comprise a hydrocarbon. In other embodiments, the hydrophobic carriers comprise petrolatum, mineral oil, and paraffin. In some embodiments, the mineral oil is heavy mineral oil. In other embodiments, the concentration of the volatile silicone fluid in the hydrophobic composition formulation is at an amount effective to enhance skin penetration of the taxane nanoparticles as compared to the hydrophobic composition formulation without the volatile silicone fluid as determined by an in vitro Franz diffusion cell system using human cadaver skin. A suitable in vitro Franz diffusion cell system is described in Example 9 below. In some embodiments, the volatile silicone fluid is at a concentration of from 5 to 24% w/w. In other embodiments, the concentration of the volatile silicone fluid is from 5 to 20% w/w. In other embodiments, the volatile silicone fluid is at a concentration of from 5 to 18% w/w. In still other embodiments, the concentration of the volatile silicone fluid is 13% w/w. In various embodiments, the concentration of the volatile silicone fluid can be 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5 or 20% w/w or any percentage derivable therein of the total composition weight. In some embodiments the volatile silicone fluid is cyclomethicone. In other embodiments the cyclomethicone is cyclopentasiloxane. In some embodiments, the hydrophobic compositions do not contain additional penetration enhancers. In other embodiments, the hydrophobic compositions do not contain additional volatile solvents. In other embodiments, the hydrophobic compositions do not contain a surfactant. In other embodiments, the hydrophobic compositions do not contain alcohols or $C_1$ to $C_5$ aliphatic alcohols. In some embodiments, the skin is diseased skin. In other embodiments, the diseased skin is psoriatic skin. In some embodiments, the hydrophobic compositions are anhydrous. In other embodiments, the hydrophobic compositions are sterile. In other embodiments, the hydrophobic compositions are non-sterile. In other embodiments, the hydrophobic compositions have a low bioburden. In some embodiments, the hydrophobic compositions are semi-solid compositions. In still other embodiments, the hydrophobic compositions are ointments. In some embodiments, the hydrophobic compositions are semi-solid compositions, including ointments, and have a viscosity of from 12,500 cps to 247,500 cps, or from 25,000 cps to 150,000 cps as measured at room temperature by a Brookfield RV viscometer using a small sample adapter with a $SC_4$-14 spindle and a 6R chamber at 5 rpm with an equilibration time of 2 minutes. An alternative method for performing viscosity measurements of the hydrophobic, semi-solid compositions is using a Brookfield RV viscometer on a helipath stand with the helipath on, with a T-E spindle at 10 RPM at room temperature for 45 seconds. In some embodiments, the hydrophobic compositions are semi-solid compositions, including ointments, and have a viscosity of from 25,000 cps to 500,000 cps, or from 25,00 cps to 400,000 cps, or from 25,000 cps to 350,000 cps, or from 25,000 cps to 300,000 cps, or from 50,000 cps to 500,000 cps, or from 50,000 cps to 400,000 cps, or from 50,000 cps to 350,000 cps, or from 50,000 cps to 300,000 cps, or from 75,000 cps to 500,000 cps, or from 75,000 cps to 400,000 cps, or from 75,000 cps to 350,000 cps, or from 75,000 cps to 300,000 cps, or from 100,000 cps to 500,000 cps, or from 100,000 cps to 400,000 cps, or from 100,000 cps to 350,000 cps, or from 100,000 cps to 300,000 cps using a Brookfield RV viscometer on a helipath stand with the helipath on, with a T-E spindle at 10 RPM at room temperature for 45 seconds.

In some embodiments, the hydrophobic compositions are not sprays and are not sprayable. In some embodiments, the taxane nanoparticles do not penetrate through/are not transdermally delivered through human cadaver skin or less than 0.01 µg/cm² (a negligible amount) penetrate through human cadaver skin as determined by an in vitro Franz diffusion cell system. A suitable in vitro Franz diffusion cell system is described in Example 9 below.

III. Methods for the Inhibition of Crystal Growth in Formulations

In one aspect of the invention, disclosed are methods of inhibiting the growth of crystalline drug nanoparticles, the method comprising contacting the drug nanoparticles with a hydrophobic carrier. In some embodiments, the drug nanoparticles are water soluble. In other embodiments, the drug nanoparticles are poorly water soluble. In still other embodiments, the drug nanoparticles are taxane nanoparticles. In other embodiments, the taxane nanoparticles are paclitaxel nanoparticles, docetaxel nanoparticles, or cabazitaxel nanoparticles. In some embodiments, the taxane nanoparticles are paclitaxel nanoparticles. In other embodiments the composition is anhydrous. In other embodiments, the hydrophobic carriers comprise a hydrocarbon. In other embodiments, the hydrocarbon is petrolatum, mineral oil, or paraffin wax, or mixtures thereof. In some embodiments, the mineral oil is heavy mineral oil. In some embodiment, the compositions further comprise one or more volatile silicone fluids. In other embodiments, the volatile silicone fluid is cyclomethicone. In other embodiments, the cyclomethicone is cyclopentasiloxane.

In another aspect of the invention, disclosed are methods of inhibiting the growth of a dispersion of crystalline poorly water soluble drug nanoparticles in an aqueous based carrier, the method comprising adding poloxamer 407, a quaternary ammonium compound, or a cross-linked acrylic acid polymer to the aqueous based carrier at the time of manufacture. In some embodiments, the additive is poloxamer 407. In various embodiments, the quaternary ammonium compound is the additive and is benzalkonium chloride or benzethonium chloride. In some embodiments, the quaternary ammonium compound is benzalkonium chloride. In some embodiments, the cross-linked acrylic acid polymer is the additive and is Carbomer. In some embodiments, the drug nanoparticles are taxane nanoparticles. In other embodiments, the taxane nanoparticles are paclitaxel nanoparticles, docetaxel nanoparticles, or cabazitaxel nanoparticles.

IV. Topical Treatment of Psoriasis

In one aspect of the invention, there is disclosed a method for the topical treatment of psoriasis, the method comprising topically administering to the affected area a hydrophobic composition comprising a continuous hydrophobic carrier, one or more volatile silicone fluids, and a plurality of drug nanoparticles, wherein the mean particle size (number) of the drug nanoparticles is from 0.1 microns to 1.5 microns or from 0.01 microns to 1.5 microns, and wherein the concentration of the drug nanoparticles is at an amount effective to provide a therapeutic improvement in the psoriatic condition. In some embodiments, the drug nanoparticles are taxane nanoparticles. In some embodiments, the taxane nanoparticles are paclitaxel nanoparticles, docetaxel nanoparticles, or cabazitaxel nanoparticles. In other embodiments, the taxane nanoparticles are paclitaxel nanoparticles. In various embodiments, the hydrophobic carriers are non-polar and/or non-volatile. In some embodiments, the hydrophobic carriers comprise a hydrocarbon. In other embodiments, the hydrophobic carriers comprise petrolatum, mineral oil, and paraffin. In some embodiments, the mineral oil is heavy mineral oil. In some embodiments, the volatile silicone fluid is at a concentration of from 5 to 24% w/w. In other embodiments, the volatile silicone fluid is at a concentration of from 5 to 20% w/w. In other embodiments, the volatile silicone fluid is at a concentration of from 5 to 18% w/w. In other embodiments, the concentration of the volatile silicone fluid is 13% w/w. In some embodiments, the volatile silicone fluid is cyclomethicone. In other embodiments, the cyclomethicone is cyclopentasiloxane. In various embodiments, the hydrophobic compositions free of/do not include or contain additional penetration enhancers. In other embodiments, the hydrophobic compositions are free of/do not include or contain additional volatile solvents. In other embodiments, the hydrophobic compositions are free of/do not include or contain a surfactant. In other embodiments, the hydrophobic compositions are free of/do not include or contain alcohols or $C_1$ to $C_5$ aliphatic alcohols.

The concentration of the taxane nanoparticles is at an amount effective to provide a therapeutic improvement in the psoriatic condition. This improvement can be indicated by an improvement in Psoriasis Area and Severity Index (PASI) scores. The concentration of the taxane nanoparticles can be from 0.05 to 10% w/w, or the concentration of the taxane nanoparticles can be from 0.05 to 5% w/w, or the concentration of the taxane nanoparticles can be from 0.1 to 5% w/w, or the concentration of the taxane nanoparticles can be 0.05, 0.1, 0.15, 0.2, 0.25, 0.3, 0.4, 0.5, 0.6, 0.7, 0.75, 0.8, 0.9, 1.0, 1.1, 1.2, 1.25, 1.3, 1.4, 1.5, 1.6, 1.7, 1.75, 1.8, 1.9, 2.0, 2.1, 2.2, 2.25, 2.3, 2.4, 2.5, 2.6, 2.7, 2.75, 2.8, 2.9, 3.0, 3.1, 3.2, 3.25, 3.3, 3.4, 3.5, 3.6, 3.7, 3.75, 3.8, 3.9, 4.0, 4.1, 4.2, 4.25, 4.3, 4.4, 4.5, 4.6, 4.7, 4.75, 4.9, 5, 6, 7, 8, 9, or 10% w/w or any percentage derivable therein of the total composition weight. In some embodiments, the taxane nanoparticles are paclitaxel nanoparticles, docetaxel nanoparticles, or cabazitaxel nanoparticles. In other embodiments, the taxane nanoparticles are paclitaxel nanoparticles. In some embodiments, the paclitaxel nanoparticles are at a concentration of about 0.05 to less than 3% w/w, or about 0.05 to about 0.2% w/w, or about 0.05 to about 0.15% w/w, or about 0.1 to about 2% w/w, or about 0.1 to about 0.2% w/w, or about 0.15 to about 2% w/w, or about 0.15 to about 0.2% w/w in the compositions. In other embodiments, the concentration of the paclitaxel nanoparticles is 80 to 120% of 1% w/w (i.e., 0.8 to 1.2% w/w), or 80 to 120% of 0.05% w/w, or 80 to 120% of 0.1% w/w, or 80 to 120% of 0.15% w/w, or 80 to 120% of 0.2% w/w, or 80 to 120% of 0.25% w/w, or 80 to 120% of 0.3% w/w, or 80 to 120% of 0.35% w/w, or 80 to 120% of 0.4% w/w, or 80 to 120% of 0.45% w/w, or 80 to 120% of 0.5% w/w, or 80 to 120% of 0.55% w/w, or 80 to 120% of 0.6% w/w, or 80 to 120% of 0.65% w/w, or 80 to 120% of 0.7% w/w, or 80 to 120% of 0.75% w/w, or 80 to 120% of 0.8% w/w, or 80 to 120% of 0.85% w/w, or 80 to 120% of 0.9% w/w, or 80 to 120° A of 0.95% w/w, or 80 to 120% of 1.5% w/w, or 80 to 120% of 2% w/w, or 80 to 120% of 2.5% w/w.

In some embodiments, the hydrophobic compositions are sterile. In other embodiments, the hydrophobic compositions are non-sterile. In other embodiments, the hydrophobic compositions have a low bioburden. In other embodiments, the hydrophobic compositions are anhydrous. In some embodiments, the hydrophobic compositions are semi-solid compositions. In still other embodiments, the hydrophobic compositions are ointments. In some embodiments, the hydrophobic compositions are semi-solid compositions, including ointments, and have a viscosity of from 12,500 cps to 247,500 cps, or from 25,000 cps to 150,000 cps as measured at room temperature by a Brookfield RV viscometer using a small sample adapter with a $SC_4$-14 spindle and a 6R chamber at 5 rpm with an equilibration time of 2 minutes. An alternative method for performing viscosity measurements of the hydrophobic, semi-solid compositions is using a Brookfield RV viscometer on a helipath stand with the helipath on, with a T-E spindle at 10 RPM at room temperature for 45 seconds. In some embodiments, the hydrophobic compositions are semi-solid compositions, including ointments, and have a viscosity of from 25,000 cps to 500,000 cps, or from 25,00 cps to 400,000 cps, or from 25,000 cps to 350,000 cps, or from 25,000 cps to 300,000 cps, or from 50,000 cps to 500,000 cps, or from 50,000 cps to 400,000 cps, or from 50,000 cps to 350,000 cps, or from 50,000 cps to 300,000 cps, or from 75,000 cps to 500,000 cps, or from 75,000 cps to 400,000 cps, or from 75,000 cps to 350,000 cps, or from 75,000 cps to 300,000 cps, or from 100,000 cps to 500,000 cps, or from 100,000 cps to 400,000 cps, or from 100,000 cps to 350,000 cps, or from 100,000 cps to 300,000 cps using a Brookfield RV viscometer on a helipath stand with the helipath on, with a T-E spindle at 10 RPM at room temperature for 45 seconds.

In some embodiments, the hydrophobic compositions are not sprays and are not sprayable.

V. Keratinous Tissue

In one aspect, the invention relates to compositions for delivery of drug nanoparticles to keratinous tissue, including nails, the nail bed, and hair. In another aspect, the invention relates to compositions for the topical treatment of diseases and conditions of keratinous tissue.

Keratinous tissue, including nails, the nail bed, and hair, is susceptible to various diseases and conditions, including fungal infections. Diseases and conditions of keratinous tissue, without limitation, include nail psoriasis, onychia, onychocryptosis, onychodystrophy, onychogryposis, onycholysis, onychomadesis, onychomycosis, onychophosis, onychoptosis, onychorrhexis, paronychia, koilonychia, subungual hematoma, onychomatricoma, laminitis, nail pemphigus, erythronychia, melanonychia, and dermatophytosis.

The compositions of the invention, including the hydrophobic compositions, are useful for the topical delivery of drug nanoparticles to keratinous tissue and for the treatment of diseases and conditions of keratinous tissue. In some embodiments, the hydrophobic compositions comprise a continuous hydrophobic carrier, 5-24% w/w of one or more volatile silicone fluids, and drug nanoparticles. In various embodiments, the hydrophobic carriers are non-polar and/or non-volatile. In some embodiments, the hydrophobic carriers comprise a hydrocarbon. In other embodiments, the hydrophobic carriers comprise petrolatum, mineral oil, and paraffin. In some embodiments, the mineral oil is heavy mineral oil.

In some embodiments, the hydrophobic compositions do not contain additional penetration enhancers. In other embodiments, the hydrophobic compositions do not contain additional volatile solvents or compounds. In some embodiments, the hydrophobic compositions do not contain alcohol or $C_1$-$C_5$ aliphatic alcohols. In other embodiments, the hydrophobic compositions do not contain surfactants. In various embodiments, the volatile silicone fluid is a cyclomethicone. In other embodiments, the cyclomethicone is cyclopentasiloxane.

In some embodiments, the hydrophobic compositions are sterile. In other embodiments, the hydrophobic compositions are non-sterile. In other embodiments, the hydrophobic compositions have a low bioburden. In other embodiments, the hydrophobic compositions are anhydrous. In some embodiments, the hydrophobic compositions are semi-solid compositions. In still other embodiments, the hydrophobic compositions are ointments. In some embodiments, the hydrophobic compositions are semi-solid compositions, including ointments, and have a viscosity of from 12,500 cps to 247,500 cps, or from 25,000 cps to 150,000 cps as measured at room temperature by a Brookfield RV viscometer using a small sample adapter with a $SC_4$-14 spindle and a 6R chamber at 5 rpm with an equilibration time of 2 minutes. An alternative method for performing viscosity measurements of the hydrophobic, semi-solid compositions is using a Brookfield RV viscometer on a helipath stand with the helipath on, with a T-E spindle at 10 RPM at room temperature for 45 seconds. In some embodiments, the hydrophobic compositions are semi-solid compositions, including ointments, and have a viscosity of from 25,000 cps to 500,000 cps, or from 25,00 cps to 400,000 cps, or from 25,000 cps to 350,000 cps, or from 25,000 cps to 300,000 cps, or from 50,000 cps to 500,000 cps, or from 50,000 cps to 400,000 cps, or from 50,000 cps to 350,000 cps, or from 50,000 cps to 300,000 cps, or from 75,000 cps to 500,000 cps, or from 75,000 cps to 400,000 cps, or from 75,000 cps to 350,000 cps, or from 75,000 cps to 300,000 cps, or from 100,000 cps to 500,000 cps, or from 100,000 cps to 400,000 cps, or from 100,000 cps to 350,000 cps, or from 100,000 cps to 300,000 cps using a Brookfield RV viscometer on a helipath stand with the helipath on, with a T-E spindle at 10 RPM at room temperature for 45 seconds.

In some embodiments, the hydrophobic compositions are not sprays and are not sprayable.

In some embodiments, the concentration of the one or more volatile silicone fluid is from 5 to 20% w/w. In other embodiments, the one or more volatile silicone fluid is at a concentration of from 5 to 18% w/w. In still other embodiments, the concentration of the one or more volatile silicone fluid is 13% w/w. In various embodiment, the concentration of the one or more volatile silicone fluid can be 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, or 24% w/w or any percentage derivable therein of the total composition weight.

In some embodiments, the concentration of the hydrophobic carrier in the compositions is greater than 10% w/w of the total composition weight. In other embodiments, the concentration of the hydrophobic carrier in the compositions is greater than 15%, or greater than 20%, or greater than 25%, or greater than 30%, or greater than 35%, or greater than 40%, or greater than 45%, or greater than 50%, or greater than 55%, or greater than 60%, or greater than 65%, or greater than 70%, or greater than 75%, or greater than 80%, or greater than 82%, or greater than 85%, or greater than 87%, or greater than 90% w/w of the total composition weight. In other embodiments, the concentration of the hydrophobic carrier in the compositions is from greater than 10% w/w to 95% w/w of the total composition weight. In other embodiments, the concentration of the hydrophobic carrier in the compositions is from 11% w/w to 95% w/w, or from 12% w/w to 95% w/w, or from 13% w/w to 95% w/w, or from 14% w/w to 95% w/w, or from 15% w/w to 95% w/w, or from 16% w/w to 95% w/w, or from 17% w/w to 95% w/w, or from 18% w/w to 95% w/w, or from 19% w/w to 95% w/w, or from 20% w/w to 95% w/w of the total composition weight.

In some embodiments, the drug nanoparticles are taxane nanoparticles. In some embodiments, the taxane nanoparticles are paclitaxel nanoparticles, docetaxel nanoparticles, or cabazitaxel nanoparticles. In other embodiments, the taxane nanoparticles are paclitaxel nanoparticles. The concentration of the taxane nanoparticles can be from 0.05 to 10% w/w, or the concentration of the taxane nanoparticles can be from 0.05 to 5% w/w, or the concentration of the taxane nanoparticles can be from 0.1 to 5% w/w, or the concentration of the taxane nanoparticles can be 0.05, 0.1, 0.15, 0.2, 0.25, 0.3, 0.4, 0.5, 0.6, 0.7, 0.75, 0.8, 0.9, 1.0, 1.1, 1.2, 1.25, 1.3, 1.4, 1.5, 1.6, 1.7, 1.75, 1.8, 1.9, 2.0, 2.1, 2.2, 2.25, 2.3, 2.4, 2.5, 2.6, 2.7, 2.75, 2.8, 2.9, 3.0, 3.1, 3.2, 3.25, 3.3, 3.4, 3.5, 3.6, 3.7, 3.75, 3.8, 3.9, 4.0, 4.1, 4.2, 4.25, 4.3, 4.4, 4.5, 4.6, 4.7, 4.75, 4.9, 5, 6, 7, 8, 9, or 10% w/w or any percentage derivable therein of the total composition weight.

In some embodiments, the drug nanoparticles are nanoparticles of antifungal agents. Suitable antifungal agents for treatment of keratinous tissue such as nails, the nail bed, and hair are azole antifungal agents such as imidazoles, triazoles, and thiazoles; polyene antifungal agents; allylamine antifungal agents; echinocandin antifungal agents; benzoic acid, ciclopirox, flucytosine, griseofulvin, haloprogin, tolnaftate, undecylenic acid, crystal violet, and balsam of peru. Non-limiting examples of polyene antifungal agents include amphotericin B, candicidin, filipin, hamycin, natamycin, nystatin, and rimocidin. Non-limiting examples of imidazoles include bifonazole, butoconazole, clotrimazole, econazole, fenticonazole, isoconazole, ketoconazole, luliconazole, miconazole, omoconazole, oxiconazole, sertaconazole, sulconazole, and tioconazole. Non-limiting examples of triazoles include albaconazole, efinaconazole, epoxiconazole, fluconazole, isavuconazole, itraconazole, posaconazole, propiconazole, ravuconazole, terconazole, and voriconazole. A non-limiting example of a thiazole is abafungin. Non-limiting examples of allyamine antifungal agents include amorolfin, butenafine, naftifine, and terbinafine. Non-limiting examples of echinocandin antifungal agents include anidulafungin, caspofungin, and micafungin. Other suitable antifungal agents include antifungal compounds disclosed in U.S. Pat. No. 7,214,506, herein incorporated by reference.

In one aspect of the invention, there are disclosed methods of topically delivering drug nanoparticles to keratinous tissue, the methods comprising topically administering to the keratinous tissue hydrophobic compositions comprising a hydrophobic carrier, 5-24% w/w of one or more volatile silicone fluids, and a plurality of drug nanoparticles. In various embodiments, the hydrophobic carriers are non-polar and/or non-volatile. In some embodiments, the hydrophobic carriers comprise a hydrocarbon. In other embodiments, the hydrophobic carriers comprise petrolatum, mineral oil, and paraffin. In some embodiments, the mineral oil is heavy mineral oil. In some embodiments, the hydrophobic compositions do not contain additional penetration enhancers. In other embodiments, the hydrophobic compositions do not contain additional volatile solvents or compounds. In some embodiments, the hydrophobic compositions do not contain alcohol or C1-C5 aliphatic alcohols. In other embodiments, the hydrophobic compositions do not contain surfactants. In various embodiments, the volatile silicone fluid is a cyclomethicone. In other embodiments, the cyclomethicone is cyclopentasiloxane. In some embodiments, the hydrophobic compositions are sterile. In other embodiments, the hydrophobic compositions are non-sterile. In other embodiments, the hydrophobic compositions have a low bioburden. In other embodiments, the hydrophobic compositions are anhydrous. In some embodiments, the hydrophobic compositions are semi-solid compositions. In still other embodiments, the hydrophobic compositions are ointments. In some embodiments, the hydrophobic compositions are semi-solid compositions, including ointments, and have a viscosity of from 12,500 cps to 247,500 cps, or from 25,000 cps to 150,000 cps as measured at room temperature by a Brookfield RV viscometer using a small sample adapter with a $SC_4$-14 spindle and a 6R chamber at 5 rpm with an equilibration time of 2 minutes. An alternative method for performing viscosity measurements of the hydrophobic, semi-solid compositions is using a Brookfield RV viscometer on a helipath stand with the helipath on, with a T-E spindle at 10 RPM at room temperature for 45 seconds. In some embodiments, the hydrophobic compositions are semi-solid compositions, including ointments, and have a viscosity of from 25,000 cps to 500,000 cps, or from 25,00 cps to 400,000 cps, or from 25,000 cps to 350,000 cps, or from 25,000 cps to 300,000 cps, or from 50,000 cps to 500,000 cps, or from 50,000 cps to 400,000 cps, or from 50,000 cps to 350,000 cps, or from 50,000 cps to 300,000 cps, or from 75,000 cps to 500,000 cps, or from 75,000 cps to 400,000 cps, or from 75,000 cps to 350,000 cps, or from 75,000 cps to 300,000 cps, or from 100,000 cps to 500,000 cps, or from 100,000 cps to 400,000 cps, or from 100,000 cps to 350,000 cps, or from 100,000 cps to 300,000 cps using a Brookfield RV viscometer on a helipath stand with the helipath on, with a T-E spindle at 10 RPM at room temperature for 45 seconds.

In some embodiments, the hydrophobic compositions are not sprays and are not sprayable. In some embodiments, the drug nanoparticles are taxane nanoparticles or nanoparticles of an antifungal agent. In some embodiments, the keratinous tissue is the nail, the nail bed, and/or the hair. In some embodiments, the disease or condition of the keratinous tissue is onychomycosis or psoriasis of the nails.

In another aspect of the invention, disclosed are methods of topically treating a disease or condition of keratinous tissue, the methods comprising topically administering to the keratinous tissue hydrophobic compositions comprising a hydrophobic carrier, 5-24% w/w of one or more volatile silicone fluids, and a plurality of drug nanoparticles, wherein the concentration of the drug nanoparticles is at a concentration effective to provide a therapeutic improvement in the disease or condition. In various embodiments, the hydrophobic carriers are non-polar and/or non-volatile. In some embodiments, the hydrophobic carriers comprise a hydrocarbon. In other embodiments, the hydrophobic carriers comprise petrolatum, mineral oil, and paraffin. In some embodiments, the hydrophobic compositions do not contain additional penetration enhancers. In other embodiments, the hydrophobic compositions do not contain additional volatile solvents or compounds. In some embodiments, the hydrophobic compositions do not contain alcohol or C1-C5 aliphatic alcohols. In other embodiments, the hydrophobic compositions do not contain surfactants. In various embodiments, the volatile silicone fluid is a cyclomethicone. In other embodiments, the cyclomethicone is cyclopentasiloxane. In some embodiments, the hydrophobic compositions are sterile. In other embodiments, the hydrophobic compositions are non-sterile. In other embodiments, the hydrophobic compositions have a low bioburden. In other embodiments, the hydrophobic compositions are anhydrous. In some embodiments, the hydrophobic compositions are semi-solid compositions. In still other embodiments, the hydrophobic compositions are ointments. In some embodiments, the hydrophobic compositions are semi-solid compositions, including ointments, and have a viscosity of from 12,500 cps to 247,500 cps, or from 25,000 cps to 150,000 cps as measured at room temperature by a Brookfield RV viscometer using a small sample adapter with a $SC_4$-14 spindle and a 6R chamber at 5 rpm with an equilibration time of 2 minutes. An alternative method for performing viscosity measurements of the hydrophobic, semi-solid compositions is using a Brookfield RV viscometer on a helipath stand with the helipath on, with a T-E spindle at 10 RPM at room temperature for 45 seconds. In some embodiments, the hydrophobic compositions are semi-solid compositions, including ointments, and have a viscosity of from 25,000 cps to 500,000 cps, or from 25,00 cps to 400,000 cps, or from 25,000 cps to 350,000 cps, or from 25,000 cps to 300,000 cps, or from 50,000 cps to 500,000 cps, or from 50,000 cps to 400,000 cps, or from 50,000 cps to 350,000 cps, or from 50,000 cps to 300,000 cps, or from 75,000 cps to 500,000 cps, or from 75,000 cps to 400,000 cps, or from 75,000 cps to 350,000 cps, or from 75,000 cps to 300,000 cps, or from 100,000 cps to 500,000 cps, or from 100,000 cps to 400,000 cps, or from 100,000 cps to 350,000 cps, or from 100,000 cps to 300,000 cps using a Brookfield RV viscometer on a helipath stand with the helipath on, with a T-E spindle at 10 RPM at room temperature for 45 seconds.

In some embodiments, the hydrophobic compositions are not sprays and are not sprayable. In some embodiments, the drug nanoparticles are taxane nanoparticles or nanoparticles of an antifungal agent. In some embodiments, the keratinous tissue is the nail, the nail bed, and/or the hair. In some embodiments, the disease or condition of the keratinous tissue is onychomycosis or psoriasis of the nails.

EXAMPLES

The present invention will be described in greater detail by way of specific examples. The following examples are offered for illustrative purposes only, and are not intended to limit the invention in any manner. Those of skill in the art will readily recognize a variety of noncritical parameters, which can be changed or modified to yield essentially the same results.

Example 1—Solubility of Paclitaxel in Various Solvents

The solubility of paclitaxel was determined in various solvents by the following method:

For each solvent, about 2 g of the solvent was weighed into a clear glass vial.

Approximately 0.1 g of paclitaxel was added to each vial.

Each vial was mixed with a stir bar on a magnetic stirrer for 2 hours at room temperature.

Each vial was then checked every 1-2 hours to see if the solution became clear. If yes, an additional approximately 0.1 g of paclitaxel was added to the vial and mixing was continued.

Step "d" was continued for each vial for a total of 48 hours.

The solution from each vial was measured for paclitaxel concentration using an HPLC method based on Agilent Technical Application Note for Paclitaxel "Analysis of Taxol by HPLC", 2002, and modified to use a 227 nm detection wavelength, rather than 204 nm (the 227 nm wavelength is used in the USP paclitaxel monograph, and reduces the solvent effects seen at lower wavelengths).

The solubility values are shown in Table 1.

TABLE 1

| Solvent | Paclitaxel Solubility at RT |
|---|---|
| Hexylene Glycol | 4.07% w/w |
| Diethylene Glycol Monoethyl Ether, | 33.10% w/w |

TABLE 1-continued

| Solvent | Paclitaxel Solubility at RT |
|---|---|
| NF (TRANSCUTOL P) | |
| Propylene Carbonate | 4.74% w/w |
| Super Refined Oleic Acid, NF | 0.041% w/w |
| Super Refined Oleyl Alcohol, NF | 0.38% w/w |
| Diisopropyl Adipate (CERAPHYL 230) | 3.51% w/w |
| Medium Chain Triglycerides, NF | 0.32% w/w |
| Propylene Glycol, USP | 0.88% w/w |
| Polyethylene Glycol 400, NF | 22.30% w/w |
| Benzyl Alcohol, NF | 17.02% w/w |
| Isopropyl Myristate, NF | 0.048% w/w |
| Mineral Oil, USP (heavy) | 0.3 ppm |
| Dimethyl Isosorbide | 38.22% w/w |
| Purified Water, USP | <0.05 ppm |

Example 2—Observations of Paclitaxel Nanoparticle Crystals in Various Substances and Solutions of Substances Paclitaxel nanoparticles were dispersed in various substances and aqueous solutions of substances and observed for crystal growth. The results are shown in Table 2.

TABLE 2

| Substance | Concentration | Visual observation by light microscopy - Needle shaped crystals observed? |
|---|---|---|
| Aqueous Based Carriers | | |
| Purified Water | 100% | Yes, >5 μm, @ 5 days, RT & 60 C. |
| Polysorbate 80 | 0.5% in water | Yes, <5 μm @ 22 days, RT & 60 C. |
| PEG 400 | 10% in water | Yes, >5 μm, @ 22 days, RT & 60 C. |
| Benzalkonium chloride (50%) | 2% in water | No, <5 μm @ 7 days & 21 days, RT |
| Magnesium nitrate | 5% in water | Yes, >5 μm @ 3 days, RT |
| Mannitol | 5% in water | Yes, >5 μm, @ 7 days, RT |
| Sorbitol | 5% in water | Yes, >5 μm, @ 7 days, RT |
| Povidone | 1% in water | Yes, <5 μm @ 7 days & 21 days, RT |
| Lecithin | 1% in water | Yes, >10 μm, @ 24 hrs, RT |
| Sodium lauryl sulfate | 2% in water | Yes, >5 μm, @ 7 days, RT |
| Ammonium lauryl sulfate | 2% in water | Yes, >5 μm @ 3 days, RT |
| Aluminum sulfate | 0.1-0.2% in water | Yes, >5 μm, @ 7 days, RT |
| Sodium phosphate monobasic | 0.75% in water | Yes, >5 μm, @ 7 days, RT |
| Zinc acetate | 1.2% in water | Yes, >5 μm, @ 7 days, RT |
| Proline | 3% in water | Yes, >5 μm, @ 7 days, RT |
| Hydroxyethyl cellulose | 1% in water | Yes, >5 μm, @ 7 days, RT |
| CARBOPOL ULTREZ 10 (with Ammonium hydroxide as neutralizer) | 0.5% in water | No, <5 μm, @ 8 days & 21 days, RT |
| Hydroxypropyl methylcellulose | 1% in water | Yes, >5 μm @ 3 days, RT |
| Saline | 0.9% NaCl in water | Yes, >10 μm, @ 7 days, RT & 60 C. |
| Polysorbate 80 | 0.5% in Saline | Yes, >5 μm @ 7 days, RT & 60 C. |
| Poloxamer 407 | 2% in water | No, <5 μm @ 5 & 7 days, RT |
| Poloxamer 188 | 2% in water | Yes, >5 μm @ 7 days, RT |
| Polyoxyl 40 Hydrogenated Castor Oil (KOLLIPHOR RH40) | 1% in water | Yes, <5 μm @ 6 days, RT |
| Vitamin E TPGS | 0.5% in water | Yes, <5 μm @ 6 days, RT |
| Hydrophobic Carriers | | |
| Mineral Oil USP (heavy) | 100% | No, <5 μm @ 3 days, RT & 40 C. |
| Light Mineral Oil NF | 100% | No, <5 μm @ 3 days, RT & 40 C. |
| FOMBLIN HC04 | 100% | No, <5 μm @ 4, 7 & 13 days, RT |
| ST-Cyclomethicone 5 NF | 100% | No, <5 μm @ 24 hrs & 13 days, RT |
| Dimethicone, 1000 cSt | 100% | No, <5 μm @ 24 hrs & 6 days, RT |
| Castor Oil | 100% | No, <5 μm @ 24 hrs & 9 days, RT |

The paclitaxel nanoparticles crystals did not grow in any of the hydrophobic carriers. Also, the nanoparticles did not grow in aqueous solutions of benzalkonium chloride, CARBOPOL ULTREZ 10, or poloxamer 407.

Example 3—Particle Size, SSA, and Bulk Density Analysis of Paclitaxel Nanoparticles The particle size of the paclitaxel nanoparticles lots used in the formulas listed in Table 3 and Tables 16-19 were analyzed by the following particle size method using an ACCUSIZER 780:

Instrument parameters: Max. Concentration: 9000 particles/mL, No. containers: 1, Sensor Range: Summation, Lower Detection Limit: 0.5 μm, Flow Rate: 30 mL/min, No. Analysis pulls: 4, Time between pulls: 1 sec, Pull volume: 10 mL, Tare Volume: 1 mL, Prime volume: 1 mL, Include First Pull: Not Selected.

Sample preparation: Placed a scoop of paclitaxel nanoparticle API into a clean 20 mL vial and added approximately 3 mL of a filtered (0.22 μm) 0.1% w/w solution of SDS to wet the API, then filled the remainder of the vial with the SDS solution. Vortexed for 5-10 minutes and sonicated in a water batch for 1 minute.

Method: Filled a plastic bottle with filtered (0.22 μm) 0.1% w/w SDS solution and analyzed the Background. Pipetted a small amount of the paclitaxel nanoparticles sample suspension, <100 into the bottle of 0.1% w/w SDS solution while stirring; placed the ACCUSIZER inlet tube into the bottle and ran sample through instrument. As necessary, added more SDS solution or paclitaxel sample suspension to reach a desired run concentration of 6000-8000 particle count.

Particles size results (based on number-weighted differential distribution): Paclitaxel nanoparticles lot used in formulas listed in Table 3: Mean: 0.861 μm, Mode: 0.572 μm, Median: 0.710 μm. Paclitaxel nanoparticles lot used in formulas listed in Tables 16-19: Mean: 0.83 μm.

The specific surface area (SSA) of the paclitaxel nanoparticles lots used in the formulas listed in Table 3 and Tables 16-19 were analyzed by the Brunauer-Emmett-Teller ("BET") isotherm method described above. The paclitaxel nanoparticles lot used in the formulas listed in Table 3 had an SSA of 41.24 m²/g. The paclitaxel nanoparticles lot used in the formulas listed in Tables 16-19 had an SSA of 26.72 m²/g.

The bulk density (not-tapped) of the paclitaxel nanoparticles lot used in the formulas listed in Table 3 was 0.05 g/cm³. The bulk density (not-tapped) of the paclitaxel nanoparticles lot used in the formulas listed in Tables 16-19 was 0.09 g/cm³.

Example 4—Anhydrous Hydrophobic Compositions of Paclitaxel Nanoparticles with Hydrophobic Carriers Anhydrous hydrophobic compositions of paclitaxel nanoparticles with hydrophobic carriers are listed in Table 3.

TABLE 3

| Component (% w/w) | F4 | F5 | F6 | F7 | F8 | F9 | F10 | F11 | F12 | F13 | A | B | C |
|---|---|---|---|---|---|---|---|---|---|---|---|---|---|
| Paclitaxel Nanoparticles | 1.0 | 1.0 | 1.0 | 1.0 | 0.5 | 2.0 | 1.0 | 1.0 | 1.0 | 1.0 | 0.5 | 0.5 | 0.5 |
| FOMBLIN HC04 | — | — | — | 15.0 | — | — | — | — | — | — | — | — | — |
| Mineral Oil USP | 10.0 | — | 5.0 | — | 5.0 | 5.0 | — | — | — | — | — | — | — |
| ST-Cyclomethicone 5 NF (Dow Corning) | — | 5.0 | 13.0 | — | 13.0 | 13.0 | 13.0 | 13.0 | 18.0 | 15.0 | qs ad 100 | qs ad 100 | qs ad 100 |
| Oleyl Alcohol | — | 5.0 | — | — | — | — | — | 1.0 | — | — | — | — | 5.0 |
| Isopropyl Myristate NF | — | 5.0 | — | — | — | — | 5.0 | 1.0 | — | 3.0 | — | 35 | 5.0 |
| Dimethicone | — | — | — | — | — | — | — | — | — | — | 5.0 | 5.0 | 5.0 |
| Fumed Silica | — | — | — | — | — | — | — | — | — | — | 5.5 | 5.5 | 2.8 |
| Cetostearyl Alcohol NF | — | — | — | — | — | — | — | — | 0.5 | — | — | — | — |
| Paraffin Wax NF | 5.0 | 5.0 | 5.0 | 5.0 | 5.0 | 5.0 | 5.0 | 5.0 | 5.0 | 5.0 | — | — | — |
| White Petrolatum USP (Spectrum) | qs ad 100 | qs ad 100 | qs ad 100 | qs ad 100 | qs ad 100 | qs ad 100 | qs ad 100 | qs ad 100 | qs ad 100 | qs ad 100 | — | — | — |

Procedure for F4-F13: Prepared a slurry of the paclitaxel nanoparticles with a portion of the cyclomethicone (or mineral oil (F4) or FOMBLIN (F7)). Heated the petrolatum to 52±3° C. and added the remaining ingredients and mixed until melted and homogeneous. Added the paclitaxel slurry and mixed until homogenous. Mixed and allowed the batch to cool to 35° C. or below. An ointment was formed.

Example 5—Physical and Chemical Stability of Anhydrous Compositions of Paclitaxel Nanoparticles with Hydrophobic Carriers The anhydrous hydrophobic composition samples were stored at 25° C. and 30° C. in 20 mL glass scintillation vials. The assay of paclitaxel was conducted using HPLC. The results of the assay and appearance stability studies are shown in Table 4 and Table 5 below. The viscosity was measured at room temperature with a Brookfield RV viscometer using a small sample adapter with a $SC_4$-14 spindle and a 6R chamber at 5 rpm with an equilibration time of 2 minutes. The viscosity results are shown in Table 6 below.

TABLE 4

| | Stability at 25° C. | | | | | | | |
|---|---|---|---|---|---|---|---|---|
| | Assay (% of target) | | | | Appearance | | | |
| Formula | T = 0 | 1 month | 2 month | 3 month | T = 0 | 1 month | 2 month | 3 month |
| F4 | 95.3 | 99.6 | 100.3 | 99.5 | Off-white ointment | Off-white to yellow ointment | Off-white to yellow ointment | Off-white to yellow ointment |
| F5 | 98.2 | 101.7 | 101.0 | 100.9 | Off-white ointment | Off-white to yellow ointment | Off-white to yellow ointment | Off-white to yellow ointment |
| F6 | 97.2 | 100.5 | 97.9 | 98.4 | Off-white ointment | Off-white to yellow ointment | Off-white to yellow ointment | Off-white to yellow ointment |
| F6** | 98.0 | 98.5 | 100.2 | NP | Off-white to yellow ointment | Off-white to yellow ointment | Off-white to yellow ointment | NP |
| F8 | 107.6 | 100.5 | 101.1 | NP | Off-white to yellow ointment | Off-white to yellow ointment | Off-white to yellow ointment | NP |
| F9 | 95.6 | 98.3 | 101.2 | NP | Off-white to yellow ointment | Off-white to yellow ointment | Off-white to yellow ointment | NP |
| F10 | 98.6 | 103.8 | 101.2 | NP | Off-white to yellow ointment | Off-white to yellow ointment | Off-white to yellow ointment | NP |
| F11 | 99.8 | 99.8 | 100.9 | NP | Off-white to yellow ointment | Off-white to yellow ointment | Off-white to yellow ointment | NP |
| F12 | 98.7 | 98.3 | 99.1 | NP | Off-white to yellow ointment | Off-white to yellow ointment | Off-white to yellow ointment | NP |
| F13 | 96.5 | 93.9 | 96.0 | NP | Off-white to yellow ointment | Off-white to yellow ointment | Off-white to yellow ointment | NP |

**repeat batch

TABLE 5

| | Stability at 30° C. | | | | | | | |
|---|---|---|---|---|---|---|---|---|
| | Assay (% of target) | | | | Appearance | | | |
| Formula | T = 0 | 1 month | 2 month | 3 month | T = 0 | 1 month | 2 month | 3 month |
| F4 | 95.3 | 99.4 | 100.1 | 99.7 | Off-white ointment | Off-white to yellow ointment | Off-white to yellow ointment | Off-white to yellow ointment |
| F5 | 98.2 | 103.2 | 101.3 | 99.2 | Off-white ointment | Off-white to yellow ointment | Off-white to yellow ointment | Off-white to yellow ointment |
| F6 | 97.2 | 102.1 | 98.0 | 95.0 | Off-white ointment | Off-white to yellow ointment | Off-white to yellow ointment | Off-white to yellow ointment |
| F6** | 98.0 | 98.7 | 102.0 | NP | Off-white to yellow ointment | Off-white to yellow ointment | Off-white to yellow ointment | NP |
| F8 | 107.6 | 99.9 | 103.0 | NP | Off-white to yellow ointment | Off-white to yellow ointment | Off-white to yellow ointment | NP |

TABLE 5-continued

Stability at 30° C.

| Formula | Assay (% of target) | | | | Appearance | | | |
|---|---|---|---|---|---|---|---|---|
| | T = 0 | 1 month | 2 month | 3 month | T = 0 | 1 month | 2 month | 3 month |
| F9 | 95.6 | 101.4 | 101.9 | NP | Off-white to yellow ointment | Off-white to yellow ointment | Off-white to yellow ointment | NP |
| F10 | 98.6 | 100.9 | 102.9 | NP | Off-white to yellow ointment | Off-white to yellow ointment | Off-white to yellow ointment | NP |
| F11 | 99.8 | 99.8 | 99.1 | NP | Off-white to yellow ointment | Off-white to yellow ointment | Off-white to yellow ointment | NP |
| F12 | 98.7 | 99.8 | 99.5 | NP | Off-white to yellow ointment | Off-white to yellow ointment | Off-white to yellow ointment | NP |
| F13 | 96.5 | 95.6 | 96.5 | NP | Off-white to yellow ointment | Off-white to yellow ointment | Off-white to yellow ointment | NP |

**repeat batch

TABLE 6

Viscosity Stability

| | Viscosity (cps) | | | |
|---|---|---|---|---|
| | F4 | F5 | F6 | F7 |
| T = 0 | 87,500 | 44,300 | 49,500 | 81,800 |
| 1 month @ 25° C. | 90,300 | 68,800 | 57,000 | NP |
| 3 month @ 25° C. | 101,000 | 47,800 | 38,000 | NP |
| 1 month @ 30° C. | 123,300 | 49,300 | 50,800 | NP |
| 2 month @ 30° C. | 112,300 | 53,500 | 38,000 | NP |
| 3 month @ 30° C. | 121,300 | 60,500 | 54,000 | NP |

Example 6—Particle Size Analysis of Paclitaxel Nanoparticles in Anhydrous Compositions with Hydrophobic Carriers Particle Size Method Using an ACCUSIZER Model 770/770A.

Instrument parameters: Sensor: LE 0.5 µm-400 µm, Sensor Range: Summation, Lower Detection Limit: 0.5 µm, Collection time: 60 sec, Number Channels: 128, Vessel Fluid Vol: 100 mL, Flow Rate: 60 mL/min, Max Coincidence: 8000 particles/mL, Sample Vessel: Accusizer Vessel, Sample Calculation: None, Voltage Detector: greater than 10 V, Particle Concentration Calculation: No, Concentration Range: 5000 to 8000 particles/mL, Automatic Data Saving: Selected, Subtract Background: Yes, Number of Autocycles: 1.

Sample Preparation: Added an aliquot of the sample formulation into a scintillation vial. Using a spatula, smeared the sample along the inner walls of the vial. Added about 20 mL of 2% Lecithin in ISOPAR-G™ (C10-11 isoparaffin) solution to the vial. Sonicated the vial for 1 minute. Insured that the sample had adequately dispersed in the solution.

Method: Filled the sample vessel with a filtered (0.22µ) 2% Lecithin in ISOPAR-G solution and analyzed the background. Using a pipette, transferred a portion of the prepared sample to the vessel while stirring. Diluted or added sample to the vessel as necessary to provide a coincidence level between 5000 to 8000 particles/mL. Initiated the analysis through the instrument and verified that the coincidence level was 5000 to 8000 particles/mL for the analysis.

The results of the particle size analysis are shown in Table 7 and Table 8 below.

TABLE 7

Particle size stability at 25° C.

| | Mean particle size, µm (number) | | | | |
|---|---|---|---|---|---|
| Formula | Initial | 1 month | 3 month | 6 month | 12 month |
| F4 | 0.77 | 0.71 | NP | NP | NP |
| F5 | 0.72 | 0.71 | NP | NP | NP |
| F6 | 0.72 | 0.71 | NP | 0.71 | 0.72 |
| F6** | 0.70 | NP | 0.70 | NP | NP |
| F8 | 0.71 | NP | 0.71 | NP | NP |
| F9 | 0.70 | NP | 0.70 | NP | NP |
| F10 | 0.69 | NP | 0.69 | NP | NP |
| F11 | 0.69 | NP | 0.69 | NP | NP |
| F12 | 0.70 | NP | 0.70 | NP | NP |
| F13 | 0.69 | NP | 0.70 | NP | NP |
| A | 0.72 | NP | NP | NP | NP |
| B | 0.77 | NP | NP | NP | NP |
| C | 0.84 | NP | NP | NP | NP |

**repeat batch

TABLE 8

Particle size stability at 30° C.

| | Mean particle size, µm (number) | | | | |
|---|---|---|---|---|---|
| Formula | Initial | 1 month | 3 month | 6 month | 12 month |
| F4 | 0.77 | 0.73 | NP | NP | NP |
| F5 | 0.72 | 0.70 | NP | NP | NP |
| F6 | 0.72 | 0.70 | NP | 0.70 | 0.73 |

TABLE 8-continued

Particle size stability at 30° C.

| | Mean particle size, μm (number) | | | | |
|---|---|---|---|---|---|
| Formula | Initial | 1 month | 3 month | 6 month | 12 month |
| F6** | 0.70 | NP | 0.72 | NP | NP |
| F8 | 0.71 | NP | 0.71 | NP | NP |
| F9 | 0.70 | NP | 0.71 | NP | NP |
| F10 | 0.69 | NP | 0.69 | NP | NP |
| F11 | 0.69 | NP | 0.70 | NP | NP |
| F12 | 0.70 | NP | 0.71 | NP | NP |
| F13 | 0.69 | NP | 0.71 | NP | NP |

**repeat batch

As can be seen by the data, the particle size of paclitaxel nanoparticles in samples F4 through F6 did not grow larger than 20% of the initial mean particle size when stored at room temperature (25° C.) and at 30° C. for 1 month. The particle size of paclitaxel nanoparticles in sample F6 did not grow larger than 20% of the initial mean particle size when stored at room temperature (25° C.) and at 30° C. for 6 months and for 12 months. The particle size of paclitaxel nanoparticles in samples F6** (repeat batch with the same formula as F6) and F8 through F13 did not grow larger than 20% of the initial mean particle size when stored at room temperature (25° C.) and at 30° C. for 3 months.

Example 7—Aqueous Based Compositions of Paclitaxel Nanoparticles

Aqueous based compositions of paclitaxel nanoparticles are shown in Table 9.

TABLE 9

| Component (% w/w) | Formula Number | | | | | | | |
|---|---|---|---|---|---|---|---|---|
| | F1 | F2 | F3 | D | E | F | G | H |
| Paclitaxel Nanoparticles | 1.0 | 1.0 | 1.0 | 0.5 | 0.5 | 0.5 | 0.5 | 0.5 |
| DGME (TRANSCUTOL P) | 5.0 | 5.0 | — | 5.0 | 5.0 | 5.0 | 5.0 | 5.0 |
| PEG 400 | 5.0 | 5.0 | 5.0 | 5.0 | 5.0 | 5.0 | 5.0 | 5.0 |
| Glycerin | 10.0 | 10.0 | 10.0 | 5.0 | 5.0 | 5.0 | 5.0 | 5.0 |
| Polysorbate 80 | 1.0 | 1.0 | 1.0 | 0.1 | 0.1 | 0.1 | 0.1 | 0.1 |
| Poloxamer 407 | 2.0 | 2.0 | 2.0 | — | — | — | — | — |
| Povidone K90 | 0.15 | 0.15 | 0.15 | 0.1 | 0.1 | 0.1 | 0.1 | 0.1 |
| Benzyl Alcohol | 0.5 | 0.5 | 0.5 | — | — | — | — | — |
| Methylparaben | 0.15 | 0.15 | 0.15 | 0.15 | 0.15 | 0.15 | 0.15 | 0.15 |
| Propylparaben | 0.02 | 0.02 | 0.02 | 0.02 | 0.02 | 0.02 | 0.02 | 0.02 |
| Benzalkonium Chloride (50%) | — | 1.0 | 1.0 | — | — | 0.1 | 0.1 | — |
| CARBOPOL 974 P | — | — | — | 0.75 | — | — | — | — |
| CARBOPOL ULTREZ 10 | 0.5 | — | — | — | 0.5 | — | — | — |
| Trolamine Solution (10%) | qs pH 5.5 | — | — | qs pH 5.5 | qs pH 5.5 | — | — | — |
| Hydroxypropyl Methylcellulose (K200M Pharm) | — | 1.0 | 1.0 | — | — | 2.0 | — | — |
| Purified Water | qs ad 100 | qs ad 100 | qs ad 100 | qs ad 100 | qs ad 100 | qs ad 100 | qs ad 100 | qs ad 100 |

Samples were observed for crystal growth of the paclitaxel nanoparticles. The results are shown in Table 10 below.

TABLE 10

| Formula Number | Visual observation by light microscopy - Needle shaped crystals observed? |
|---|---|
| D | No, <5 μm @ 24 hrs & 6 days, RT |
| E | No, <5 μm @ 24 hrs & 6 days, RT |
| F | No, <5 μm @ 24 hrs & 6 days, RT |
| G | No, <5 μm @ 24 hrs & 6 days, RT |
| H | Yes, >5 μm @ 24 hrs & 6 days, RT |

As can be seen by the data, the presence of benzalkonium chloride, CARBOPOL 974P, or CARBOPOL ULTREZ 10 inhibited the growth of crystals in the aqueous based compositions.

Example 8—Particle Size Analysis of Paclitaxel Nanoparticles in Aqueous Based Compositions Particle Size Method Using an ACCUSIZER Model 770/770A.

Instrument parameters: Sensor: LE 0.5 μm-400 μm, Sensor Range: Summation, Lower Detection Limit: 0.5 μm, Collection time: 60 sec, Number Channels: 128, Vessel Fluid Vol: 100 mL, Flow Rate: 60 mL/min, Max Coincidence: 8000 particles/mL, Sample Vessel: Accusizer Vessel, Sample Calculation: None, Voltage Detector: greater than 10 V, Particle Concentration Calculation: No, Concentration Range: 5000 to 8000 particles/mL, Automatic Data Saving: Selected, Subtract Background: Yes, Number of Autocycles: 1.

Sample Preparation: Added an aliquot of the sample formulation into a scintillation vial. Using a spatula, smeared the sample along the inner walls of the vial. Added about 20 mL of 0.2 μm filtered distilled water to the vial.

Sonicated the vial for 1 minute. Insured that the sample had adequately dispersed in the solution.

Method: Filled the sample vessel with 0.2 μm filtered distilled water and analyzed the background. Using a pipette, transferred a portion of the prepared sample to the vessel while stirring. Diluted or added sample to the vessel as necessary to provide a coincidence level between 5000 to 8000 particles/mL. Initiated the analysis through the instrument and verified that the coincidence level was 5000 to 8000 particles/mL for the analysis.

The results of the particle size analysis are shown in Table 11 below.

TABLE 11

Particle size of aqueous based compositions

| Formula | Mean particle size, μm (number) | |
|---|---|---|
| | Initial | 6 month at RT |
| F1 | 1.06 | 0.82 |
| F2 | 0.74 | 0.77 |
| F3 | 0.70 | 0.77 |
| D | 0.80 | NP |
| E | 0.79 | NP |
| F | 0.85 | NP |

As can be seen by the data of formulas F1, F2, and F3 in Table 11, the presence benzalkonium chloride, CARBOPOL 974P, or CARBOPOL ULTREZ 10 inhibited the growth of crystals in the aqueous based compositions such that the mean particle size of the drug nanoparticles did not grow larger than 20% of the initial mean particle size when the composition was stored at room temperature for 6 months.

Example 9—In Vitro Skin Penetration Diffusion Study

A study to determine the rate and extent of in vitro skin permeation of the formulas F1 through F13 into and through intact human cadaver skin using a Franz diffusion cell system was conducted. Concentrations of paclitaxel were measured in the receptor chamber of the diffusion cell at varying time points. Upon conclusion of the diffusion study, the skin was tape stripped and split into epidermal and dermal layers. The paclitaxel in the epidermal and dermal tissue was extracted using an extraction solvent and also analyzed.

Analytical Method: A Mass spectrometry (MS) method was developed for analyzing the paclitaxel. The MS conditions were as follows in Table 12 below.

TABLE 12

| Instrument: | Agilent 1956B MS (TM-EQ-011) |
|---|---|
| Column: | XBridge C18 4.6 × 100 mm, 5 μm |
| Mobile Phase: | A: Acetonitrile |
| | B: 0.1% Formic acid in water |

| | Time (minutes) | % B |
|---|---|---|
| Gradient: | 0 | 50% |
| | 2 | 5% |
| | 5 | 5% |

TABLE 12-continued

| Flow Rate: | 1 mL/min |
|---|---|
| Column Temperature: | 30° C. |
| MS Detection: | SIM 854.4+ Frag 180, Gain 20 |
| Injection Volume: | 20 μL |
| Retention time: | ~2.86 min |

Franz Diffusion Cell (FDC) Study—Methodology

Skin Preparation: Intact human cadaver skin was purchased from New York Firefighters Tissue Bank (NFFTB). The skin was collected from the upper back and dermatomed by the tissue bank to a thickness of ~500 μm. Upon receipt of the skin from the tissue bank, the skin was stored frozen at −20° C. until the morning of the experiment. Prior to use, the skin was removed from the freezer and allowed to fully thaw at room temperature. The skin was then briefly soaked in a PBS bath to remove any residual cryoprotectants and preservatives. Only areas of the skin that were visually intact were used during the experiment. For each study, two separate donors were used, each donor having a corresponding three replicates.

Receptor Fluid Preparation: Based on the results of preliminary solubility data, a receptor fluid of 96 wt % phosphate buffered saline ("PBS") at pH 7.4 and 4 wt % hydroxyl propyl beta cyclodextrin (HPBCD) was chosen. The solubility of the active in the receptor fluid (~0.4 μg/mL) was shown to be adequate to maintain sink conditions during the studies. The receptor fluid was degassed by filtering the receptor fluid through a ZapCap CR 0.2 μm membrane while pulling vacuum. The filtered receptor fluid was stirred for an additional 20 minutes while maintaining vacuum to ensure complete degassing.

Diffusion Cell Assembly: The cadaver skin was removed from the freezer and allowed to defrost in a bio-safety hood for 30 minutes. The skin was thoroughly defrosted prior to opening the package. The cadaver skin was removed from the package and placed on the bio-safety hood countertop with the stratum corneum side up. The skin was patted dry with a Kimwipe, then sprayed with fresh PBS and patted dry again. This process was repeated 3 more times to remove any residues present on the skin. The receptor wells were then filled with the degassed receptor fluid. A Teflon coated stir bar was added to each receptor well. The defrosted cadaver skin was examined and only areas with even thickness and no visible damage to the surface were used. The skin was cut into ~2 cm×2 cm squares. The skin piece was centered on the donor cells, stratum corneum (SC) side up. The skin was centered and the edges flattened out. The donor and receptor wells were then aligned and clamped together with a clamp. Additional receptor fluid was added where necessary. Any air bubbles present were removed by tilting the cell, allowing air to escape along the sample port. Diffusion cells were then placed in to the stirring dry block heaters and allowed to rehydrate for 20 minutes from the receptor fluid. The block heaters were maintained at 32° C. throughout the experiment with continuous stirring. The skin was allowed to hydrate for 20 minutes and the barrier integrity of each skin section was tested. Once the membrane integrity check study was complete, the entire receptor chamber volume was replaced with the receptor fluid.

Formulation Application Procedure: The formulations were applied to the stratum corneum of the skin. A one-time dosing regimen was used for this study. The test articles were applied as 10 μl doses to the skin using a positive displacement Nichiryo pipetter. The formulations were then spread across the surface of the skin using a glass rod. Cells were left uncapped during the experiment. The theoretical dose of paclitaxel per cell is shown in Table 13 below.

TABLE 13

| Formula Number | % w/w Paclitaxel in formula | Nominal formulation dose per cell | Theoretical Paclitaxel dose per cell |
|---|---|---|---|
| F1 | 1.0 wt % | 10 μl | 182 μg/cm$^2$ |
| F2 | 1.0 wt % | 10 μl | 182 μg/cm$^2$ |
| F3 | 1.0 wt % | 10 μl | 182 μg/cm$^2$ |
| F4 | 1.0 wt % | 10 μl | 182 μg/cm$^2$ |
| F5 | 1.0 wt % | 10 μl | 182 μg/cm$^2$ |
| F6 | 1.0 wt % | 10 μl | 182 μg/cm$^2$ |
| F7 | 1.0 wt % | 10 μl | 182 μg/cm$^2$ |
| F6* | 1.0 wt % | 10 μl | 182 μg/cm$^2$ |
| F8 | 0.5 wt % | 10 μl | 91 μg/cm$^2$ |
| F9 | 2.0 wt % | 10 μl | 364 μg/cm$^2$ |
| F10 | 1.0 wt % | 10 μl | 182 μg/cm$^2$ |
| F11 | 1.0 wt % | 10 μl | 182 μg/cm$^2$ |
| F12 | 1.0 wt % | 10 μl | 182 μg/cm$^2$ |
| F13 | 1.0 wt % | 10 μl | 182 μg/cm$^2$ |

*repeat analysis

Sampling of Receptor Fluid: At 3, 6, 12 and 24 hours, 300 μL sample aliquots were drawn from the receptor wells using a graduated Hamilton type injector syringe. Fresh receptor medium was added to replace the 300 μL sample aliquot.

Tape Stripping and Heat Splitting: At 24 hours, the skin was wiped cleaned using PBS/ethanol soaked KimWipes. After the residual formulation was wiped off and the skin dried with KimWipes, the stratum corneum was tape stripped three times—each tape stripping consisting of applying cellophane tape to the skin with uniform pressure and pealing the tape off. The tape strips were collected and frozen for future analysis. The first three tape strips remove the uppermost layer of the stratum corneum and act as an extra skin cleaning step. The active is typically not considered fully absorbed in this area. These tape strips are usually only analyzed for a mass balance assay. After the skin was tape stripped, the epidermis of each piece was then separated from the underlying dermal tissue using tweezers or a spatula. The epidermis and dermal tissue were collected and placed in 4 mL borosilicate glass vials. After all the skin pieces were separated, an aliquot of the extraction solvent was added to the glass vial. This process consisted of adding 2 mL of DMSO to the vial and incubating for 24 hours at 32° C. After the extraction time was over, 300 μL sample aliquots of the extraction fluid were collected and filtered.

Analysis of Samples: Sample aliquots were analyzed for paclitaxel using the analytical method as described above.

Figure 2:
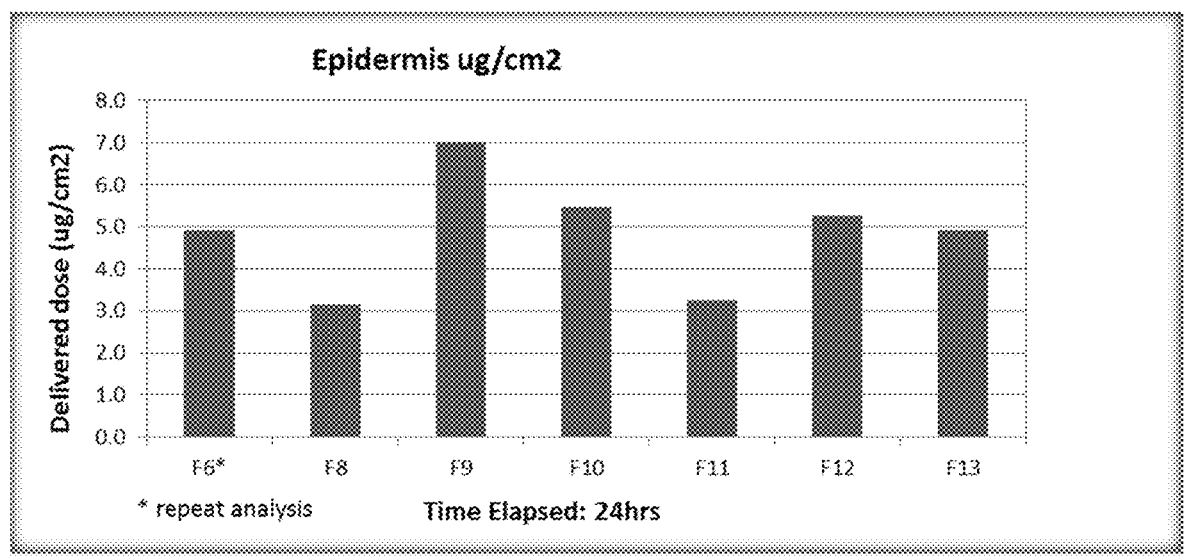
FIG. 2 graphically shows the concentration of paclitaxel (µg/cm2) delivered in vitro into the epidermis for formulas F6* (repeat analysis) and F8 through F13.
Figure 3:
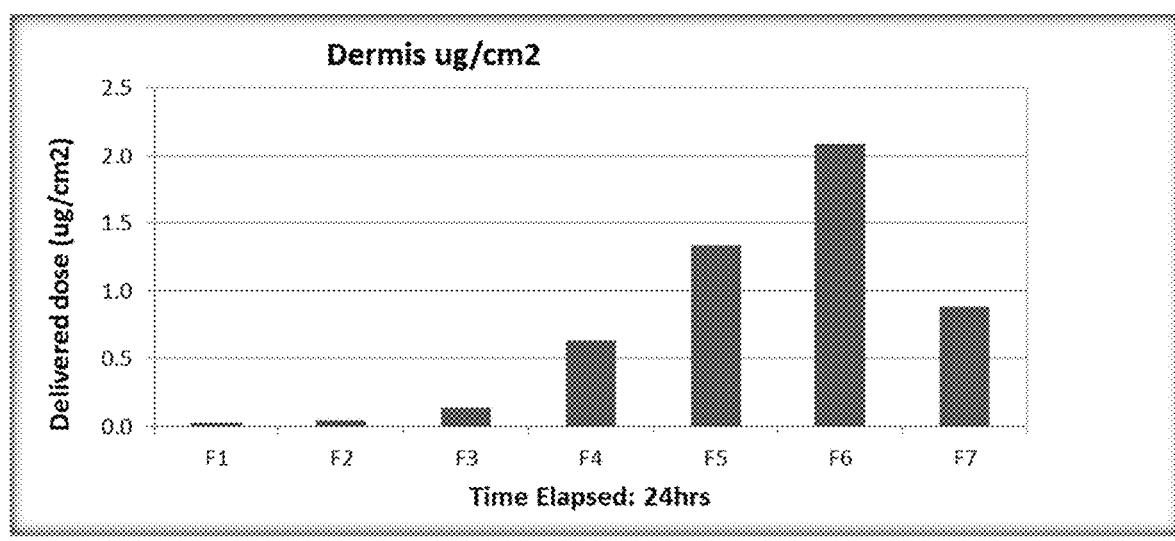
FIG. 3 graphically shows the concentration of paclitaxel (µg/cm2) delivered in vitro into the dermis for formulas F1 through F7.
Figure 4:
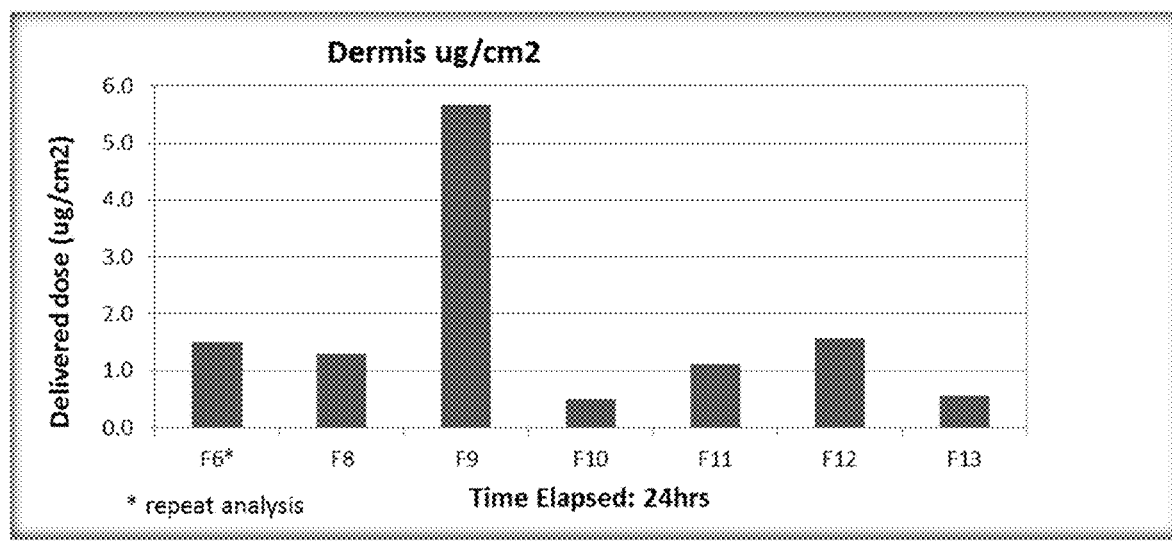
FIG. 4 graphically shows the concentration of paclitaxel (µg/cm2) delivered in vitro into the dermis for formulas F6* (repeat analysis) and F8 through F13.

Results:

The results in Table 14 below show the delivered dose of paclitaxel (μg/cm$^2$) in the receptor fluid at various time points (transdermal flux) and the concentration of paclitaxel (μg/cm$^2$) delivered into the epidermis and dermis (penetration) after 24 hours elapsed time for formulations F1 through F13. FIG. 1 graphically shows the concentration of paclitaxel (μg/cm$^2$) delivered into the epidermis for formulas F1 through F7. FIG. 2 graphically shows the concentration of paclitaxel (μg/cm$^2$) delivered into the epidermis for formulas F6*(repeat analysis) and F8 through F13. FIG. 3 graphically shows the concentration of paclitaxel (μg/cm2) delivered into the dermis for formulas F 1 through F7. FIG. 4 graphically shows the concentration of paclitaxel (μ/cm2) delivered into the dermis for formulas F6* (repeat analysis) and F8 through F13.

Note: Formulas F 1 through F6 were tested in one in vitro study, and formulas F6* and F8 through F13 were tested in a second separate in vitro study, with different cadaver skin lots. Analysis of formula F6 was repeated in the second study (and notated as F6*) so that it could be evaluated and compared with the other formulas in the second study.

TABLE 14

| | Paclitaxel Delivered Dose (μg/cm$^2$) | | | | | |
|---|---|---|---|---|---|---|
| Formula | Receptor Fluid 3 hrs | Receptor Fluid 6 hrs | Receptor Fluid 12 hrs | Receptor Fluid 24 hrs | Epidermis | Dermis |
| F1 | 0.000 | 0.000 | 0.000 | 0.000 | 0.202 | 0.030 |
| F2 | 0.000 | 0.000 | 0.000 | 0.000 | 0.161 | 0.042 |
| F3 | 0.000 | 0.000 | 0.000 | 0.000 | 0.056 | 0.138 |
| F4 | 0.000 | 0.000 | 0.000 | 0.000 | 0.690 | 0.639 |
| F5 | 0.000 | 0.000 | 0.000 | 0.004 | 0.780 | 1.337 |
| F6 | 0.000 | 0.000 | 0.000 | 0.000 | 1.927 | 2.088 |
| F7 | 0.000 | 0.000 | 0.000 | 0.000 | 0.633 | 0.882 |
| F6* | 0.000 | 0.000 | 0.000 | 0.000 | 4.910 | 1.508 |
| F8 | 0.000 | 0.000 | 0.000 | 0.000 | 3.155 | 1.296 |
| F9 | 0.000 | 0.000 | 0.000 | 0.000 | 7.010 | 5.679 |
| F10 | 0.000 | 0.000 | 0.000 | 0.000 | 5.470 | 0.494 |
| F11 | 0.000 | 0.000 | 0.000 | 0.000 | 3.262 | 1.098 |
| F12 | 0.000 | 0.000 | 0.000 | 0.000 | 5.269 | 1.571 |
| F13 | 0.000 | 0.000 | 0.000 | 0.000 | 4.903 | 0.548 |

*repeat analysis

As can be seen by the results in Table 14, the transdermal flux of the paclitaxel through the skin (epidermis and dermis) was none or only a negligible amount, i.e., less than 0.01 μg/cm$^2$. As can be seen by the results in Table 14 and FIGS. 1, 2, 3 & 4, the penetration of paclitaxel into the skin (epidermis and dermis) was far greater with the anhydrous hydrophobic formulations (F4 through F13) than with the aqueous formulations (F1 through F3), even though the aqueous formulations contained the skin penetration enhancer DGME (TRANSCUTOL P). The results also show that the anhydrous hydrophobic formulations with cyclomethicone exhibited greater skin penetration (epidermis and dermis) over the anhydrous hydrophobic formulations without cyclomethicone. Additionally, the results show that the addition of other skin penetration enhancers to the anhydrous hydrophobic formulations containing cyclomethicone had little or no effect on the skin penetration (epidermis and dermis) of these compositions.

Example 10—Human Psoriasis Plaque Study

The following formulations shown in Table 15 were prepared for use in a human psoriasis plaque study.

TABLE 15

| Component (% w/w) | Formula No. | | | | |
|---|---|---|---|---|---|
| | BR16008A (0.15%) | BR16001A (0.3%) | BR16002A (1%) | BR16003A (2%) | BR16005A (placebo) |
| Paclitaxel Nanoparticles | 0.15 | 0.3 | 1.0 | 2.0 | 0.0 |
| Mineral Oil USP | 5.0 | 5.0 | 5.0 | 5.0 | 5.0 |
| ST-Cyclomethicone 5 NF (Dow Corning) | 13.0 | 13.0 | 13.0 | 13.0 | 13.0 |
| Paraffin Wax NF | 5.0 | 5.0 | 5.0 | 5.0 | 5.0 |
| White Petrolatum USP (Spectrum) | qs ad 100 | qs ad 100 | qs ad 100 | qs ad 100 | qs ad 100 |

The formulas listed in Table 15 containing paclitaxel nanoparticles were manufactured each in a 6 Kg batch size. The placebo formula was manufactured in a 12 Kg batch size. The formulas were then packaged in 15 gm laminate tubes.

The manufacturing processes for lots BR16008A, BR16001A, and BR16002A were as follows: The petrolatum, mineral oil, paraffin wax, and a portion of the cyclomethicone were added to a vessel and heated to 52±3° C. while mixing with a propeller mixer until melted and homogeneous. The paclitaxel nanoparticles were added to a vessel containing another portion of cyclomethicone and first mixed with a spatula to wet the nanoparticles, then mixed with an IKA Ultra Turrax Homogenizer with a S25-25G dispersing tool until a homogeneous slurry is obtained while keeping the container in an ice/water batch. The slurry was then added to the petrolatum/paraffin wax container while mixing with the propeller mixer followed by rinsing with the remaining portion of cyclomethicone and mixed until the batch was visually homogeneous while at 52±3° C. The batch was then homogenized using a Silverson homogenizer. Afterward, the batch was mixed with a propeller mixer until a homogeneous ointment was formed and the batch cooled to 35° C. or below.

The manufacturing process for lot BR16003A was as follows: The petrolatum and paraffin wax were added to a vessel and heated to 52±3° C. while mixing with a propeller mixer until melted and homogeneous. The paclitaxel nanoparticles were added to a vessel containing the cyclomethicone and a portion of mineral oil, and first mixed with a spatula to wet the nanoparticles, then mixed with an IKA Ultra Turrax Homogenizer with a S25-25G dispersing tool until a homogeneous slurry is obtained while keeping the container in an ice/water batch. The slurry was then added to the petrolatum/paraffin wax container while mixing with the propeller mixer followed by rinsing with the remaining portion of mineral oil and mixed until the batch was visually homogeneous while at 52±3° C. The batch was then homogenized using a Silverson homogenizer. Afterward, the batch was mixed with a propeller mixer until a homogeneous ointment was formed and the batch cooled to 35° C. or below.

The chemical and physical analytical results for each formula listed in Table 15 are shown in Tables 16-20 for T=0, 1 month, and 3 months at 25° C.

TABLE 16

| | Formula No. BR16008A (0.15%) | | |
|---|---|---|---|
| Test | T = 0 | 1 month | 3 month |
| Appearance (note 1) | conforms | conforms | conforms |
| Assay, % target | 103.4 | 103.2 | 101.1 |
| Viscosity (note 2) | 131000 cps | 147000 cps | 159500 cps |
| Mean Particle Size (number) | 0.71 µm | 0.70 µm | 0.70 µm |

(note 1):
Off-white to yellow ointment (note 2):
Brookfield RV viscometer on a helipath stand with the helipath on, with a T-E spindle at 10 RPM at room temperature for 45 seconds.

TABLE 17

| | Formula No. BR16001A (0.3%) | | |
|---|---|---|---|
| Test | T = 0 | 1 month | 3 month |
| Appearance (note 1) | conforms | conforms | conforms |
| Assay, % target | 101.2 | 101.9 | 102.5 |
| Viscosity (note 2) | 195500 cps | 154000 cps | 153500 cps |
| Mean Particle Size (number) | 0.72 µm | 0.71 µm | 0.70 µm |

(note 1):
Off-white to yellow ointment (note 2):
Brookfield RV viscometer on a helipath stand with the helipath on, with a T-E spindle at 10 RPM at room temperature for 45 seconds.

TABLE 18

| | Formula No. BR16002A (1%) | | |
|---|---|---|---|
| Test | T = 0 | 1 month | 3 month |
| Appearance (note 1) | conforms | conforms | conforms |
| Assay, % target | 102.1 | 102.2 | 102.7 |
| Viscosity (note 2) | 205000 cps | 218000 cps | 180000 cps |
| Mean Particle Size (number) | 0.70 µm | 0.70 µm | 0.70 µm |

(note 1):
Off-white to yellow ointment (note 2):
Brookfield RV viscometer on a helipath stand with the helipath on, with a T-E spindle at 10 RPM at room temperature for 45 seconds.

TABLE 19

| | Formula No. BR16003A (2%) | | |
|---|---|---|---|
| Test | T = 0 | 1 month | 3 month |
| Appearance (note 1) | conforms | conforms | conforms |
| Assay, % target | 101.7 | 101.1 | 105.0 |
| Viscosity (note 2) | 158000 cps | 177000 cps | 162000 cps |
| Mean Particle Size (number) | 0.70 μm | 0.69 μm | 0.69 μm |

(note 1):
Off-white to yellow ointment
(note 2):
Brookfield RV viscometer on a helipath stand with the helipath on, with a T-E spindle at 10 RPM at room temperature for 45 seconds.

TABLE 20

| | Formula No. BR16005A (placebo) | | |
|---|---|---|---|
| Test | T = 0 | 1 month | 3 month |
| Appearance (note 1) | conforms | conforms | conforms |
| Viscosity (note 2) | 256000 cps | 244500 cps | 222000 cps |

(note 1):
Off-white to yellow ointment
(note 2):
Brookfield RV viscometer on a helipath stand with the helipath on, with a T-E spindle at 10 RPM at room temperature for 45 seconds.

The formulas listed in Table 15 were used in a human clinical psoriasis plaque study that is currently on-going, which consisted of a two-center, randomized, placebo trial that was double-blinded for the IPs with intra-individual comparison of treatments. Twelve male and post-menopausal female volunteer subjects, aged 18 years or older, with psoriasis vulgaris and mild or moderate chronic plaque(s) in a stable phase and an area sufficient for 6 treatment fields were enrolled in the study. Each formula that contained paclitaxel nanoparticles in addition to the placebo formula was administered topically, once daily, 10 times over a 12-day trial period. Efficacy was determined by measurement of psoriatic infiltrate using 22-MHz sonography and a clinical scoring on a scale of 0-3 points (0=unchanged, 1=slight improvement, 2=clear improvement but not completely healed, 3=completely healed).

Preliminary results of the plaque study for 2 out of the 12 subjects (one male age 36 and one female age 47) are presently available and are as follows:

TABLE 21

| Average Clinical Assessment of Efficacy | | | | |
|---|---|---|---|---|
| | Baseline | Day 4 | Day 8 | Day 12 |
| BR16005A (placebo) | 0 | 0 | 0.5 | 0.5 |
| BR16008A (0.15%) | 0 | 0.5 | 1 | 1 |
| BR16001A (0.3%) | 0 | 0.5 | 0.5 | 0.5 |
| BR16002A (1%) | 0 | 0.5 | 1 | 0 |
| BR16003A (2%) | 0 | 1.5 | 1 | 0 |

TABLE 22

| Ultrasound Evaluation - Average Change from Baseline (micrometers) | | | | |
|---|---|---|---|---|
| | Baseline | Day 4 | Day 8 | Day 12 |
| BR16005A (placebo) | 0 | 27 | 50.5 | -23.5 |
| BR16008A (0.15%) | 0 | -11.5 | -47 | -39 |
| BR16001A (0.3%) | 0 | 35 | 113.5 | 31 |
| BR16002A (1%) | 0 | 0 | 37.5 | -3.5 |
| BR16003A (2%) | 0 | 82 | 35.5 | 58.5 |

The invention claimed is:

1. A hydrophobic topical skin composition comprising greater than 50% w/w of the composition of a continuous hydrophobic carrier, 5-24% w/w of one or more volatile silicone fluids, and 0.1 to 5% w/w of the composition of a plurality of taxane nanoparticles, wherein the mean particle size (number) of the taxane nanoparticles is from 0.1 microns to 1.5 microns, wherein the taxane from the nanoparticles is capable of penetrating into the epidermal and dermal layers of skin when the composition is applied to the skin, and wherein the taxane nanoparticles are crystalline nanoparticles or a combination of amorphous and crystalline nanoparticles.

2. The composition of claim 1, wherein the volatile silicone fluid is cyclomethicone.

3. The composition of claim 2, wherein the cyclomethicone is cyclopentasiloxane.

4. The composition of claim 1, wherein the composition does not contain an antibiotic and a propellant.

5. The composition of claim 1, wherein the composition is anhydrous.

6. The composition of claim 1, wherein the hydrophobic carrier is non-volatile.

7. The composition of claim 1, wherein the hydrophobic carrier is non-polar.

8. The composition of claim 1, wherein the hydrophobic carrier comprises a hydrocarbon.

9. The composition of claim 8, wherein the hydrocarbon is petrolatum, mineral oil, or paraffin wax; or mixtures thereof.

10. The composition of claim 1, wherein the taxane nanoparticles are crystalline nanoparticles.

11. The composition of claim 1, wherein the taxane nanoparticles are a combination of amorphous and crystalline nanoparticles.

12. The composition of claim 1, wherein the taxane nanoparticles are paclitaxel nanoparticles, docetaxel nanoparticles, or cabazitaxel nanoparticles.

13. The composition of claim 1, wherein the taxane nanoparticles are paclitaxel nanoparticles.

14. The composition of claim 13, wherein the paclitaxel nanoparticles have a specific surface area (SSA) of at least 18 m$^2$/g.

15. The composition of claim 1, wherein the composition does not contain a $C_1$-$C_5$ aliphatic alcohol.

16. The composition of claim 1, wherein the composition does not contain an antibiotic.

17. The composition of claim 1, wherein the composition does not contain a propellant.

18. The composition of claim 1, wherein the composition does not contain an additional skin penetration enhancer.

19. The composition of claim 1, wherein the composition does not contain an additional volatile solvent.

20. The composition of claim 1, wherein the composition does not contain a surfactant.

21. The composition of claim 1, wherein the composition does not contain a protein or albumin.

22. The composition of claim 1, wherein the composition is a semi-solid composition.

23. The composition of claim 22, wherein the semi-solid composition is an ointment.

24. The composition of claim 1, wherein the viscosity of the composition is 25,000 cps to 500,000 cps as measured with a Brookfield RV viscometer on a helipath stand with the helipath on, with a T-E spindle at 10 RPM at room temperature for 45 seconds.

25. A method for delivering taxane nanoparticles to skin, the method comprising topically applying the composition of claim 1 to skin.

* * * * *